US010472634B2

(12) United States Patent
Rigo et al.

(10) Patent No.: US 10,472,634 B2
(45) Date of Patent: Nov. 12, 2019

(54) ANTISENSE COMPOUNDS TARGETING APOLIPOPROTEIN E RECEPTOR 2

(71) Applicants: Ionis Pharmaceuticals, Inc., Carlsbad, CA (US); Rosalind Franklin University of Medicine and Science, North Chicago, IL (US)

(72) Inventors: Frank Rigo, Carlsbad, CA (US); Michelle L. Hastings, North Chicago, IL (US)

(73) Assignees: Ionis Pharmaceuticals, Inc., Carlsbad, CA (US); Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 15/315,828

(22) PCT Filed: Jun. 4, 2015

(86) PCT No.: PCT/US2015/034264

§ 371 (c)(1),
(2) Date: Dec. 2, 2016

(87) PCT Pub. No.: WO2015/187989

PCT Pub. Date: Dec. 10, 2015

(65) Prior Publication Data

US 2017/0191066 A1 Jul. 6, 2017

Related U.S. Application Data

(60) Provisional application No. 62/007,854, filed on Jun. 4, 2014.

(51) Int. Cl.

| | |
|---|---|
| ***C12N 15/113*** | (2010.01) |
| *C12N 5/00* | (2006.01) |

(52) U.S. Cl.

CPC ...... *C12N 15/1138* (2013.01); *C12N 2310/11* (2013.01); *C12N 2310/111* (2013.01); *C12N 2310/315* (2013.01); *C12N 2310/321* (2013.01); *C12N 2310/322* (2013.01); *C12N 2310/3231* (2013.01); *C12N 2310/3233* (2013.01); *C12N 2310/351* (2013.01); *C12N 2310/3521* (2013.01); *C12N 2310/3525* (2013.01); *C12N 2310/3533* (2013.01); *C12N 2320/33* (2013.01)

(58) Field of Classification Search

None

See application file for complete search history.

(56) References Cited

U.S. PATENT DOCUMENTS

| | | | | |
|---|---|---|---|---|
| 2007/0248599 | A1* | 10/2007 | Tang | 424/133.1 |
| 2008/0113351 | A1* | 5/2008 | Naito | A61K 31/713 435/6.11 |
| 2008/0254033 | A1 | 10/2008 | Pierce et al. | |
| 2014/0114057 | A1 | 4/2014 | Hastings et al. | |

FOREIGN PATENT DOCUMENTS

| | | |
|---|---|---|
| WO | WO 2008/049085 | 4/2008 |

OTHER PUBLICATIONS

Singh et al. International Journal of Pharmacology vol. 7(3):294-315, 2011.*

Chishti et al., "Early-onset amyloid deposition and cognitive deficits in transgenic mice expressing a double mutant form of amyloid precursor protein 695." J. Biol. Chem. (2001) 276(24): 21562-21570.

Janus et al. "A beta peptide immunization reduces behavioral impairment and plaques in a model of Alzheimer's disease." Nature (2000) 408(6815): 979-982.

International Search Report for application PCT/US2015/034264 dated Sep. 14, 2015.

* cited by examiner

*Primary Examiner* — Sean McGarry
(74) *Attorney, Agent, or Firm* — McNeill Baur PLLC

(57) ABSTRACT

The present invention provides compounds comprising oligonucleotides complementary to an LRP8 transcript. Certain such compounds are useful for hybridizing to an LRP8 transcript, including but not limited, to an LRP8 transcript in a cell. In certain embodiments, such hybridization results in modulation of splicing of the LRP8 transcript. In certain embodiments, such hybridization results in an increase in inclusion of exon 19 in the LRP8 mRNA transcript. In certain embodiments, such compounds are used to treat Alzheimer's Disease.

19 Claims, No Drawings

Specification includes a Sequence Listing.

SEQUENCE LISTING

```
<160> NUMBER OF SEQ ID NOS: 57

<210> SEQ ID NO 1
<211> LENGTH: 83410
<212> TYPE: DNA
<213> ORGANISM: Homo sapiens

<400> SEQUENCE: 1

ccagccctgc gcccccagct tctccctgct catccacatc ttgggatctc acccctatcc      60

ctccctcccc cgccccacgc gcacactgca caggcctgtt cgtcctgtaa catcatttcc     120

cctcccgccc aggctcactc ctagacatcc ctcagcctct gatccgcctg tcacctcctc     180

caggaagcct ctgctgcttc ctctggacct gctacctccg tggtgagggg ctcgcctggc     240

ccatccctgc gtctgcagag cccagcactc aggcgagccc agagcagggc cgtggagcgc     300

ccgctgagag aagagtggac gaaagacagg agggaggagg gcgaggaggc ggcggcaggg     360

ggagcgtggg gcggaggcgg cagcgggagg gagcgcgcgc gctggcggcg gccgcccagg     420

gccggggccg cgcgcccagc ctgagcccgc cccgccgccg agcgtcaccg aacctgcttg     480

aaatgcagcc gaggagccgg ggcgggcggc agcggcggcg gcggcggcgg cgggggcagc     540

ggcaaccccg gcgccgcggc aaggactcgg agggctgaga cgcggcggcg gcggcgcggg     600

gagcgcgggg cgcggcggcc ggagccccgg gcccgccatg ggcctccccg agccgggccc     660

tctccggctt ctggcgctgc tgctgctgct gctgctgctg ctgctgctgc agctccagca     720

tcttgcggcg gcagcggctg atccgctgct cggcggccaa ggtgcgtgca gccggtctct     780

gactcggctc tgctccgccc tagccaccaa caaagcgcgg ccgggaggcc ggagcgggga     840

ggggtccaga acccggggct atcgggggct cccgggcgga caggctccac gcgaagcggc     900

tattcctgaa tttgccctcg gccccccgcc cccgcgggcc tcggtgttga gggctctgcc     960
```

```
ctctgggcag cggatcttgg gggaggggtg caggggggct tggccagcgg ggaactttgc   1020
cggaggggcg gccattcatg gttccggatg agctgtgtga ttctcgccgt tggggtttat   1080
ttgacacgcg cgctccgcgg cggtaatgag cagagccggg cggcttctcc gcttgacaat   1140
gcgtttccgc agacccctgc gcgcggcgga gagagagggg gctgcctgcc agggtgatgt   1200
gcctgcggct cccactgcgc ctggcgcgcg ggcgcgggga ctccctatgg gctgtatctg   1260
agcagatctc tgactatggg tcgcgtgtgc gggtgagtgc gtctgaatgg agggtatacc   1320
caggtcgtgt gacactttaa gtaggtgcct ggtctcgccg tgccaccgag cggcccgaca   1380
tccacggaac ccctgccatc gtgccctccc tttggatgga gtgtgcctga agcccccggg   1440
gtctccataa tcgcccctt tcctcctccc cagcgggtcc ttccgggtgg cccggactgc   1500
atggtgggga gtggggccga gtccgctgat ccagctcacg ctccctcccc ctcgcagggc   1560
cggccaagga ttgcgaaaag gaccaattcc agtgccggaa cgagcgctgc atcccctctg   1620
tgtggagatg cgacgaggac gatgactgct tagaccacag cgacgaggac gactgccgtg   1680
agtggcgggc cagggagctc agacccgggg agagaaaagg aacggtgggg ggcaccatgc   1740
ttggcgcgca cgtggctgca gccgccgcgc tgccacctgc gcgggacttg ccgccggagc   1800
ctgcgaccgg gaaaccgcct gggcaccgcc tccctcgggg ccgggtggct cttagcgacc   1860
cggagcgggc aggaaagctg gcgtgtcctg gtggggccgg ggcggagccc cgggcagtgt   1920
gccggaggag gaaggcgcac catgctgggg agactgaacc ggagctgtgg gcggggacgc   1980
ggcagtccct gcaaaggtct agcttcccga aacacggccc tctcggactc ttgcctcggc   2040
cccgcgggac gcgcgcgtgt ttcaaagttc cacgcagctc cgggccgcac tgcgctcctt   2100
ttcctgctca gtttttgtga atgaatgggc tccccagggc ccctgattgg ctgggcgagg   2160
accaccccat aggcccccgt ggccggagcg gccaatcgcg gagcagacgg atgtgtagta   2220
ttcgggttcc ctgggcgcgg gggcaccgcc ctgccctgcc ccggccccgc cccggccaca   2280
cccccgcgca tatccttagg gtggtaggtg caggcggggc tcgggcgccg cttttctgcc   2340
gagtcacagt gaagaccttt ttgagccacc ctggttagca gaccgcgctt tcctgctagc   2400
cctgcccggc tctgagtcat gtggcacacc aggaaggagg gtaccaggag ggagagtttg   2460
tttcctggaa ggggcccgag aagcccgagg ccacgcgtga aacggctgcc ggccgccttt   2520
gctgggcgtg cgcgactgat ttagaagttt cttctcagag tgcacagggt ttcagagtgt   2580
ctgcgggacc gggagctagt tagcaggcag ttgtcacggt ggaagaaatg tagctccggg   2640
aacagaaaaa cagggctctc ctagagacat agacccgggc agtcattcat tcatcattcg   2700
ggagcatctg ctgcgtgcca ggcgctgggg cgccctccaa gacaggccag ccctgccagc   2760
cagggagcac tgacggggtc tgagggagga gggcgacagg tggacaggcc cacagcccca   2820
cactgcacag gaagggtcac gggacacttg gacaggcacc ctctctgttg aatcgttttg   2880
gtttttgact gtttgccagt caccctcccg ttcactttca gacctaaccc aaagttggct   2940
ttgtgtcttg tgcgtggcag aactagactg actgagtcta tgtctctagc acatctttcc   3000
ctcctgcctc agtttcctca cctgaccact tgggttcaca taattcctgc cccagcaaca   3060
tcattggact gttttgagga ccagttctag aagcgaaatt ggaagtaatg agactaatgt   3120
gtgctgacca ttaactgtgc caagcactgc agtaagtact tatcttgtat aaactccttt   3180
aatcttcata acagtcctat tttagagatt aaaaaacaaa acaaacaaac caacaaaaac   3240
tgaggcactg aactgtgaag ttacctgctt agcagctact gagttgttaa gtaggagcct   3300
```

```
gaacttaagc atctaactct agagttctta gtctaatcat gaccctggac catttcccag   3360
tgctgttgag gttatgaaaa tggctgtgcc ttggtaaaat attgcagtga gtttcctcac   3420
tgggagttgt tctgtggtct ccttagagtg ggagtactga ggacgaggca aggaatagaa   3480
actgcgtgtc tgggctggtt atgccttatc tccctggctc tttataacaa ctgtccttgt   3540
gaggatggct gtgaaaagca gaaattttct tgtcattcta ctttctagat aaggatgcct   3600
cctcagagaa gttgagtgac ttatgcaagg tcacacagct caggatgaca gaacttggtc   3660
aggatctctg cctgcctcga gttcagggca ctgtctgctg aggtggggag tgtggtgcgg   3720
aaagcaccag gagtgtgatc taggagctgg aaagacgggc tttaaatgtt aggcctggtg   3780
cgtttcagct ccatgtgagg ctttggacga gatggaggag taaagtagct gggtgctgag   3840
tgacgctcag gtgggccaag agagctccaa tggccaagct gggctcctgc atggctctga   3900
gatgcatggg gtagagtcat aggcagggag ttattaaaca aaagtgaatg acgtcaagct   3960
tggagtggaa agggtggcgg cgctgctgat agtaccaagt agtaatcaca catggcttgg   4020
cttttctgag cttgtttcct catctgccaa acaggggcag ctgtccctcc aacgctggct   4080
gtgcacatag acacacaggg ctggcaagaa gggaacggat ggatgagtgt tcccacctcc   4140
acggccttta gaaacggact cctggtagcc ataaagggaa actgaagaaa cggagtgggg   4200
cttacgtggc tgtgttgggg ccaggtgctg gaaaatgttc tttcctcagc ccttcccgca   4260
ttctaggcca cctgcccaga ctgaatttct ttgaactgtt ctccctgcag gagagagagc   4320
tgttggctcg tccctgagga gctctttatt aaacctggga tggaggggtg ataggtgctg   4380
ggataacaaa atctgctcct ccctgagcag tctccgtgcc ttacccctga ccaccctctt   4440
tggcacacca ccctgcaaga gggcttgagc tgccccacct ttgtacatct ctgggcctgc   4500
aaaatggggg ttggaatttg tagatagagt ctgcgtgagg caaaatgagt ccaagttccc   4560
aaaggggcca gaatgcagcc cctgaatacc aagaggctgg aaggagggaa cttttaagga   4620
agccaagaaa ggcttcctgg aggaggagac tgctgaacta ggcctgaaag atggtaacta   4680
atagcattcc cccagagttt accatttaaa aacaggtggt attgttccta tattatagag   4740
gacataggct tggagaggtg aagtgactcc cccaaagtca cagagctcct cagggttgga   4800
gctggaactc aaactgaggc cttctaagtc ccgagcctca tccacagtgg ctgggacttg   4860
gctctttgga gacacagatg gagcttgcgg gatggaagag ggaaaagctc ctggggcttt   4920
agttctcagc tcaaagaacc ttcaaagtgg aggaaggagc tggaagctag agagccaggc   4980
ccaaggaagc ccagccaggg gaagtcgggt gggattcctg gctgtgggcc tgggtcacgt   5040
aggccagctg gcccctgggc ctcagtttcc tgttgctccc tagtgtctgg gggcagaggc   5100
agagattccg gtctctggcc tggcctttac tcccagagtc acaacagtaa ccatagcgcc   5160
gatgaacgct gtctgggcac ttgctgtgga ccgggcatcg tgctgagatt gtccacacat   5220
cgcccctcgt tcctctattc tataaaatgg ggcaacacta tgaagtacct gaaatagtcc   5280
tatctcatcg aggcacagac gggttacgta actggcccaa gggtgtagaa ctgctggggt   5340
gtgaatgcgg gtgaccagct atggaacttg tactgtctca agtactggct ggtgacttag   5400
gtaggtcctt cccaggcctt catttccctg tcttgagatg acatcttaag gctactccac   5460
ctcgcttcct cctctaggaa gttctgtgct tctcgcggaa aggctgggta gacaggtgga   5520
ccagttttgt gctcactgac ctcgactttg ttcaggcttc tttggactct tttgttatcc   5580
cagcacccat cacccctcca tcccaggttt aataaagagt ggccacaggg aggtctccca   5640
tggctgagag ttcattagct gggcaaggcc aggctgcagg agtgctgagt cttgctggga   5700
```

```
aacagcctca taaataatta aagctcggcc acagctccct gcctgtgctg tagcccgcat   5760
ctggccctca gtgtgcggcc tggacgtgtg ctcctgacac tggacccagc ctcatctcct   5820
tcgtggatgg agccatctga cgacagtgtg gctcctttct gaacctcccc gtcttcacct   5880
gaccgggcaa ctccaccatc cagagtcctc ctggggctcc caactatcca gagaataaag   5940
tcagtgtaga ctcctctgta tttggccctc tgtgacctgc tcctgttacc cacttccctg   6000
caacctcttc ccgcctcttc ctgtgagcct gtgacaccaa attagcttct gccacactct   6060
caccctcctg ctgcttctca cctccaggcc tttgtgtgtg ctattcctcc tgccggacac   6120
cctgctccct cactggctgg attcatttta tcatcctaag agatccggtg caggtgtcac   6180
ctcctctagg aagccttccc tgacacccca ttgcctccag gctgagatac aggatttgag   6240
ttacttagag acccatgtca aagtcacaac tcagacacac ctggttttta catcccagct   6300
gtcgcctcct ggatgaatgg ttgtgaggat gatactaggc cctccttttc ggagattaaa   6360
tgtgaggatt aaatgaggtc acatgcctgg taagcaggag gtgttcagtg aatggcagtg   6420
ggtgaggttg ttcttggtgg gaggggtttc actgaggtct ctaggtacct gacgtctggt   6480
ctttgcaggc caacccggac cccttgcttc ccctgctcct gtctgcttag ccagatgtcg   6540
aggttcctgc agctggtgct cgcctcagcc agggagttgc ccagccaccg tagaggtgac   6600
agaaagctgc ttggaaagga gctgggggaa gaaatgagtc aaacaggcct agggccctag   6660
gaggggcagc ggatggcttc cctctggctg tgtgctggtc ctagaggctg gcttctgtcc   6720
tgtctgctcc tttcctcttg gctgtgcctg gggaggagag gagggcctgc atcccccatg   6780
gcactgccca gcaggcccta gcaggccttg ggagtgtttg ctgaagactt tcccttgggc   6840
cctcccaggt cagcattccc cggtgtgagt cccttgggcc tcagggatgg ttggcttctt   6900
cctccccagt tgtctgctgg tggccgactt gacaactttc ctccttgggg aaatgctggt   6960
agcaggtgaa gccagagaga gagagacccc cagggggcag tgaggagcga gagcccagag   7020
ggcggatgga acaggcacgc ccttgaagga agtaaatgca tgcatgctct cccagcacca   7080
ggttagtggt ctactcccag gcccatgctg tcccaggggg ccagcactgg ggtctgtggg   7140
agggtgtggg gttgtgtcct tagggttgtg gagccaggcc ttgcagcccc aggcctaagt   7200
aacgttggta gcacctgccc cccaaatgcc cacacatcca gatcacccag gctctgaagg   7260
cctggcaggg atgccacttc ctccagagat gcctttctag acccctgtcc tccagcccct   7320
caggccctga gctcccacaa cgtgtccttt ttcttcccgc agttgcagat ccttctcaac   7380
attgtgcact ccgccagcct tgtgctgggc agtaggaatt ccaaagtcgt ttcctcaagg   7440
ggtagctaat aacagctatt ggctgcctat atcccatgcc tgggaccacg ttggacaatt   7500
cacatccttt aacttcacta ctcacaaccc tgggagggct agtttttcgt tctcatttcg   7560
aagatgatga aactgaggct cagaaaggag acggaacttg gccaatgtca tgaccattaa   7620
gtggtggagc caggagctga cccaggtctg tctggtctgg agcccagact cttcttaagc   7680
cgttccccgc tgagcgctgt ctaccctggt ggggtcagag gctggtgctt ggagggtgtg   7740
ggaggaagta gggagcagct gcaggactca gcagtgcctc cctgagctac cagtttctga   7800
cctggggagt gggactgggg agggaccctg ttctctggag accccgcaga gccctcacat   7860
aggccttttc cagctcccat ggggatgaca ttccagtttt cataggcttc tctcagcctt   7920
tgcctgttag atgctgattc ttcttctgac tgtatggaag ggaaaactga gaacctgatg   7980
atagtgatgc acatgacctc agggagtgtc agcccagggt catctctttt actctctgta   8040
```

-continued

```
gtaacacggg gcctggctgc ctcctcgcac ccaggcttag aaaggtgaaa ctaaggccct   8100
gatggtcgaa ttggctccat cgtcagtagg gcaccattct cagaactcag gtgtcctcaa   8160
ttctgggtgg gactggagtc agaactgtat gtgcttcccc ctcccacccc caccctcttt   8220
gttccctgct ggatccggga acagggtgct ctcaggctga ggggtggaca caagcctttt   8280
gcagtaccga agggctttgg gctcctgact ggggacctca ggtgcaccac tggccccact   8340
gggccctgct tgcccacttc tggattgcca agaagtcatc taaaatactc acgttaacac   8400
taagaagagt tagggagcga gctagtgagg ggctttctca tgcaagacct ccttcagccg   8460
gtgccttgag gtatcatgac tgcatttcgc agaggagaga accaagactc tgagagatga   8520
agtcacttgc cccgggtggc cccgctggtc agtggcagga ctgggccatg cctgtctggc   8580
tgcaggtctg aggcagctga aaggagatat gcattcacac atcccagtca cgatgacagt   8640
aaagtgtggc ttgcaggctg tgctggggcc tctcttcctt tccaggcgtc cctctttgcc   8700
agcacctgct agtgggtgtg ccaactccct cctgagcagc ccagcccctt gggcgccctc   8760
cagcatgagc tgggtccccc ggcagcggtt ttaattatca gccctgctca ccccagctcc   8820
tctcacaagc tgccatatgt catagactcc agtaatcacc ccgcagccgg agtggcaggg   8880
gaggggctga gggccttcag gggaatcctg ctcagtcttg accgagttcc tcactgactg   8940
tacccgctct gacctctttg tctctggtgg ggcccagcct aggtacccac aatgggagag   9000
ccgggcctag ctgctttggg ggcatagaat gcggcatgct ctcaggcgcc atggagtgtc   9060
cttgggaaac tgagagtcac ccagcgagcc cagggctgtg ggctcatgt ggtgcacaca    9120
gttcccatga cccctcatgg cctctacacg cctgcccctt ggaacgtggc atgtggcagg   9180
acagacaccc caaagctgtc tgccagtctg tctaggagtc cacgggagtg gtcatttggc   9240
ccccatcctc ccctggtcac tggccttgag gtaccacagg ggacttcatc ccagccactc   9300
tggagggcat cttagtttcc agccctctca acctgccgta atccttggat ggcttttcca   9360
gttggtgcct cacaggtgtg ctcctgggag gcaggcggtg caggagttca ttatgatccc   9420
cattccttga tgaggaaaac gaggctcaga gaggataaga gactcaccca gttattggta   9480
gttctggagc taaaactcac ttcaactgat tttacttatt tagttttcca gggtaagtaa   9540
cttctggtta gctgaaagta actttacact tgtaatgaaa aacatagtta ataaagaaca   9600
ggaaacgaag gttgcagtga gccgagatca caccactgca ctccagcttg gacgaaggta   9660
gttctcaccc ttgctagtac cactatgtaa gcagcatagc cttctagaga tttttctctg   9720
catgtgagct cttgggcatg aacatatgta tttttttttt ttaacaaaaa tgaggccatg   9780
ttatgccggt tgttttcaca tatggctttc tatggcaata acagtagttc acatccttgt   9840
tttaaagggc tagatagtat tgtattgtgt ggatcttcca taatttaatg acattttctc   9900
ccgttgatag atgtgtgttt ggttgcttcc atgtttttcc ctgctctgtg caatgctagg   9960
atggacatcc ttgaactcca tccttgtgca tttgcttggt cctttcttta agataagttc  10020
ttaggaaagg agctgctgag tgtgtgcatt ttcatcattg ccgttctgct ctctagaggg  10080
gagaatcttt cccatctcac aactctctcc ctctatggcc ccatggctct cctttccagc  10140
gaggcaggca gctgaaggac ttccctcttc tctgagcaca gggccacctc attctggtcc  10200
catgggacaa agcagccata tccaggccac agaaagcaaa gccaggagag agaacaacga  10260
gcggtgttct ggccccaagg gctttcaccc ccaccaaaaa aaaaaaaaag cagaagagta  10320
caaaactgtt ccttcattct tctcaggata ttggtagaag gcatctcctc cgcagcgttc  10380
taattcttct atctatgccc ctaacttgct gtgtgacctt gggtgaatgg ctctccctct  10440
```

```
ctgaacttca ttttcctttc actcattggt ccttattcca cctgcactgc cccagcact  10500
tggagcagac tcctgtgcct ggagctgggt tcagggctgg agctggccag tccttgccta  10560
gggcagggat ctgtgcctta ctacctggtg acagtgcggg gagtatagct ggcttggtgg  10620
gctggattct gggcagggaa acagggcagc tggactcctt agctccactt ccagagctcc  10680
accctgaggc ccaggttcct tgggtgactt tcccttctgc cttcttcctg cactcacaat  10740
tgggccggat gcagtgcagt gatggagaaa aatggagtga ggcccaccag cttcatgaga  10800
ctttccgaaa gcgggaaaat gagcccatat tccggaggtg tgcgggctga ggaaagtact  10860
ttgcccagag cctggccctg aaaatgagcg tttcccttcc cttcctgagc ctgtgattcc  10920
tgcacaggga atggctgagt aaaaggaacc gtcctcagct ttcctcctcc tccaccaagg  10980
acacaacaag agggcagcag caaaatagca gcaggagaga tttaggtcaa ctggccagtt  11040
gggaggactt ggctgcctga gagaacagca gctcctcggg ctgggaggga ctgtcggagc  11100
catctcatcc caccccatct gcgctggggc cccagggtgg ctgcttcctg agtggcccag  11160
tggggctggt tagccagccg ggcctgccac ggtagttagc cacgtggggc cttggttccc  11220
cagtgggtcc aggctaacat cagagacttg gcagctgatg agaggcagga aggtcccatc  11280
aggcccaggt taagctgccc gactgaatag ctggaggcca agggtgggct ttcctggtgg  11340
cctgaatcca gggacattca agccagcact cctcccctcc ctccctcccc cacttcctgg  11400
accctgagcc gccatctgct gccctacact ctcagagccc tttctcggcc atgggcatgg  11460
gcacatgtgc gtgtgcttgg ggtgtgtgct tcagaggagg ggctgtgtac caggagggag  11520
gtgactattc tggacccgtg gaggctatgg ggccaagatg acactcttct cccatacccg  11580
ctaagtctgc ccaaaccaag ccagagctcc ccgcctcccc accaggccgt cgtggtgggg  11640
aatgatttgt agctggagag gcgccagcag tctctcttcc tggcctgccc cctgccacag  11700
cagcctctcc tccccaggcc atgtgtgctc tggtcccacc cggagagggc tgcttgttat  11760
aaacagcagc cttcctcctc tgctcccacc ttgccgagtg gccatttggc agatgcttgc  11820
ccctcttggg gtctctgccc cttgggagta gggcatctcc agcccctctc aatcccattc  11880
tgtggaattc ttttgttttc ccctaagagt cagggattca catggtggga gtctgccatg  11940
gccaggcccc aggtacaggg tgctccaagg agctggccct gttctctgag gcccagggct  12000
ggaagcatgg gggcaggggc tgtgaaatcc aaccccatgg ggccccaaca ggagacatgg  12060
cctaaaccac acaactgttt attagcagag cctacatcta ctggaggctt tttacaccta  12120
cttatttttg tgctgagctc tgacggggct gattttttaa tacctatgag ccagtgagag  12180
cagactctac atcagctgcc tatgcaacac tcttttgtct ccctcccctc cccattccca  12240
gcctgcctct actgcctact gtaggggcca agtggtacat caggccagcg tggcctctcc  12300
agcagcagcc agacctggct tccagctgca gctctcccac ttcctggttg ggaggccccg  12360
gggcaagtcc cttgaatgga accccagact cccgctctga acaacatggg taataaataa  12420
ttcctggcct atgtaaagta gcagaaacct ccttggccct cagtgtgtga gttccatgag  12480
ccagtcggtt cttcttacac cactgaattg gaccaagcaa accagggcag agtggtctgg  12540
cagcccatgt ggcttgagcc cctgttctct ctgccacctc ccccaccatg ccttgccctc  12600
ccctctggcc cttggtctct cccacccttg aagatcctgt gctgatgtct cccctctgtg  12660
acagaggcct gatcccttgt tgctgctggc taactgacct acctggctgg ctgccctcca  12720
ggctgtcagc ctcaccttgt ccccaacatg ccatgtgatc tgggtgtatt cctgctctgg  12780
```

```
ggctctgaga gactgaggat tagatcagtg gtttgtgtca cttggggcag ctttttaaat  12840
tctgccccag ccccttccag gcccatttgg tgcgaagcca gctgggaggt gtagatgtgc  12900
aagtccccag gacgggcccc tacctcatcc aggagaggat ctatcacgac atggataaca  12960
gcagggccct accaggccgc ctggggtcaa gtccacacct caccacttcc cagatgtggg  13020
gccctaagca aatgacttca cctctctgag cacctgcctc atctggagga tggagccgcc  13080
cctcaaggtg gttgtgggat tgacaggtga gttaacttct gaggcacact aagagcagtg  13140
catggtgcat gcgcagtgct caattcaaga ttgcctgggc ttcttttgac ctccttctct  13200
gaacctccct ctcccatctg tccttcagga atccccatcc ttactgggct gctgcactgc  13260
ggggtggagt aggaggagcc agggagcccc cagaaagact cctttatctc cctttctccc  13320
ctgccgctcc aggctgtcac ttgctggccc agtttaatta gggagaggcc ttctagggac  13380
ctcattagga aatgagccca gagccttagg gaccttcagg aggggtgggg tgcagaagga  13440
gattacatta tggttggccc tgcctggccc ctggctttgt gccctaaata tgcctaggaa  13500
gttatggaca cttggtcctt tagtggccag gacacaggcc tgtgacatgg tgcatggtca  13560
gccagggctg aagggaccca tgcttctatc tcctactccc cctgggctct ggcctcacct  13620
cccagatcag gatggagaag ggtgacagag gaggcttatc tggttctgct ccacccagcc  13680
caggtgccca ctgtccccag cgtggctcag agcaggccct ggtgaaggtg ttgagtgaat  13740
ggatgtgtga gctgtgggca gcatcttcat taggccaaag cggcctcccc cttccatccc  13800
agtgcaggag tttcctcagc agcctagtgg ggtggaggtc agggggtcca atgcgtccgg  13860
ggactgggcg ctcacccact gacgaagcag ctccccgccc ctggactgct cttcctgtta  13920
gaaaacctgc tcttctgtca atcccagatc tgtctcctgc agctctcctg ccctctctga  13980
tcccagctct gttaatgggg cctctgctta cagagtctgc ccccaccttc acggcaagcc  14040
tgccccatgt cccttcctac ctgcattctt gccacagccc ccatgcttag ggaagtccag  14100
cctgtgacag ctgacttgtg gtgtgggctc agataaggac catcctctct ggggccattg  14160
ctgctttggc tcccctagca tggggcctgg tggcgtgcac attcgcaggc tctataaatg  14220
ttagctgcat cctgtgactt gcctcccagg gctttgagaa gtggagggtg aggacagaaa  14280
tgccgtgcct ggaggcaaag gtatcgttat ggacagcttg ctctcctggg tagcagggca  14340
gcagcgccca gatcctgcaa tgactgtggc acagcacata gcactggggg gctgtggctg  14400
aacgtcttct gcctcttgga ctaggccgga gtgcaggcat tgcctgggcc ttgggcagga  14460
acctgggagt catcacaacc cctctcttcc ttcccccaag gcctcacctt gaatagggga  14520
aggaagaagg tcccgacact caccctgcct acctgccagc ctgggcctcc cccgcccctg  14580
ccacccactg ccatgccctt cctggatctc agcagcagcc cctgcctagt ttctgttctg  14640
tcctccaaac ccatcttcgc tctgcagctg agtgctctga gagatgcaaa gctacaccct  14700
ttcctcgctc agcttctgca gtgacgccca cccctcatag gaccaagtct tcttaactga  14760
cattcagagc ccttcaagac cagacatgta cctgtctcct ctccaggtct cacctggcac  14820
tgaccccaag ccccaggcgt ctcctgtcca gccacacctc caagagaagc ctcaggccct  14880
tttgcatgca ggcccctagc ctggaaggct ccatctctgc ttgtccggcc tcacctgacc  14940
tctggagtca ccatttccag ggtgcttcct cccctaggtg ggtcagagtc tcctctgggc  15000
tctctcatcc ttgtgtttcc ccacactcta taccatgatg tcctgattta gagtctgtgg  15060
ttcacaatgc agtccacaag cctcaggggg acagggacct gtggaggacg gtggaggaag  15120
gaggggtgga gggtgcctct gggctccgag tgtgcactgt gcccctgacc ccttgctagg  15180
```

```
tttccagccc ctcttgccgc acatgactgg gtgtggtttt ctgtgagtcc ctgggaagcg  15240
cctgctgtgg actggagcct ttgggtccca gctccaacat tcactgaggg tttgttctgt  15300
gccaggtgcc ctgccagaac ctggggagga tctacagatg ggaaagcagg ccacgccctg  15360
ggggcaccag cccctaactt aatgtgtgac cttttctgaa cctcagcttc ctctgctgtg  15420
aaggggatga ggacccaaga cccttccctg ttaccttggg tacatctatg ctgtggctgg  15480
gatcagacat ggccccgcat gaccctgagg ctgcagctag accagaactt gccctccact  15540
gggcctctgg aacactggtc caagcttcac aggagcaagg ggtgagcaga ggttttgctc  15600
tcttttcagc gaaaacgccc acttcatttg cccagcacgt cagcattgcc atgtgcttgc  15660
catgcataaa ttgaacacgg ctcctcggct gctcagaact atcccagttt taaaactcaa  15720
catcctgcat ctcaggaacc ccttcagttg tgagcaaact gggacacttg accagtctag  15780
ctgagccccc aagccctggc cactgctctc tcaggtcccc aggaggtcct ccccatccct  15840
tgtggaatct gctagctggg cacggctcac ttaattaaaa acaaagaaaa aggccaggca  15900
cagtggctca cacctataat cccagaattt tcgggaggct gagatgggag gatcacttaa  15960
ggccgggagt tcaaggccag cctgggcaac atagtgagac tccgtctctc aaaaaaaaaa  16020
aaaattagcc aggtgtcatg gtccatgcct atagctactt gggaggctga agcaggagga  16080
ttgcttgagc ccaggagttt gaggttgcag tgggctatag tcatgccgct gcactctggc  16140
ctgggtaagg aagccagacc ctgtctcaac ccctgcctgc caaaagaaaa gactgatttc  16200
ttcctcacct tttgggagaa ctcaagaaag aaacagagga tcttggaagg tctggaagag  16260
cagggccaaa cattctgagt agggagctgt gtggataggg ccaggaggcc tggccgctgt  16320
tacagactgc ctctagccca gctgtgtgac ctccctccct ggcctgtttc cccatctctg  16380
ccctgctcac ctcgtatgac tgtggtgaga atcataacat tcatgggcct gcctgtgtta  16440
ccaccgccat ttctattctt ccaggcatgt ggctgtctgt ctgtgtccca tgttggcctc  16500
actcctccca agtggagggc agcactgaga tcgttgttct catgatgaat agaaagaagc  16560
tggaggcgct ggccacgtgc cttgtatgag tctctgcagt cgacaaggcc cttcccacat  16620
gttgcctcca ggctcatggt ggcccttggg aggtgggcca gcaggaatga ctccacccat  16680
tgtacagatg gggacactga gcccatagtc ccacagcatc tgactcctta atggtgggga  16740
gaagggaagc cacatgggtg gctgggctgt ggccgtggcg tgtggtggtt acgagtgggg  16800
tcactggttg gctggtcctc ttcccctccc tatgcccact ctgtcgatgt cttcatcagt  16860
agggagagat ggagacagat ggaagagaag gcagagacag aggagtaggg agagagagat  16920
ggggtgggct ggggagcaca ctggggaggc tgggggcagg gagggtccac gcagtatcgc  16980
tccttcctct gtggttctca cagtctgtct gcaccgattc ctgacagatg gagggaggag  17040
agagctagtg ccaagaggct gtcaccacag gcgggcagag ttgggggagg gcgctttgtg  17100
gccagggctt gtgtggggag gggaagcagc tggtggtctg gctgctgggc ctccttggag  17160
cccacacccc aggaactgcc aggggacaag aaagtgggca aagggtaagc ccgccacctg  17220
cctgggactg gccgtgccca tgcccctgtc caggcagaga cagctacccc tccccgctcc  17280
tcacaccctg ctgccagcag ggccctccct gtaaactatg gattcctcct gcgcacccct  17340
cactcggtgt tgggggtggg caggggcctg gggactggcc ctgagctgtg atgggggtgg  17400
accagggcag ggaggccccc gggataccgg agggcatggc agctcagagc aggctggggt  17460
ctgggtcttg catctgctgg ctggagctca gccctcactg tgctaccctg gatgtttccc  17520
```

aagccccttt tcatggcata gggcctcctg catttcctcc gggctctgaa gcatgtgcag 17580
ggctgggcag gcatgacccg gggtcgattt ggcacctttg tcatctcctg tgtctttata 17640
gtatggcttt cttcaggcag gactggcttt catgcactct ttcccaaccc cccagtgccc 17700
atcacagggc ccagcacaga ggaggggccc attgtatgct tgttgaatga atgaatggat 17760
ccccctgctt gcatacctcc tgggatggag gcctcactcc tttatacaac aattggttcc 17820
aagattttca gaaacgaagt tctttctggt tcttcccgag aggctccatg gctcccaggc 17880
ttgccacagg ggccacacag acaccctggc tgatcctgcg tcctcagagc agcgcagaaa 17940
agaccagaga cctctgagcc agcccagctc ctcacaggct cctgcacggc tgggtctcca 18000
ctgcactaac ctctgggttg tcagtaatca taggtgtcac atatggagcc ctcactgtgc 18060
caggcagcat ctcattccat tcacatcagc ctgtaaggca ggtagttctc atcccccatt 18120
tacagaggag aaaaatgact tcctccaggt cacacggctt agcaggagac agaacatctg 18180
agtcaggagg gtgggaggtg ggctggggtg ggctggagga agacctcctg gagcatggga 18240
ttgtggcagg gcttggggat actgggggct tggcaggagg gggcaaggct gaggaggggc 18300
ccaagggctt ttctggaggt ggaatctgcc cctgcccctg ccccagcccg tctcttccct 18360
ctccccatgc tgtctccaaa tggatccctg acaccaagac tccaactggg gtagtcccag 18420
aggtgagacc tgtgaacctg gggcccagag cccttcctgt ccccctgaag gccagggtgt 18480
gggtatgctc cggggcagag ctcaaggccg ctaaactgac aggaaaggtc agtccagtga 18540
tccgagacgt gcagggttat ggctgggggc gtggggactc ccatctctgg tgaagcgtcg 18600
gggtaggtgg gtggggctgg gcttcctttc tgctgctgct caaagttggt tctgctcaga 18660
agcatcctcc cattcatatg aataacggcg atcactgatg ataaatgaag gtgtgcctgc 18720
cccgtgccag ggctgggctg ggtgccctgg ggacagctga gaggagtcgg aggtggaatc 18780
catcctgaga gcaggggcac agctttcacc acctttatct catccccgga gcctgacaca 18840
ggctgggccc tcagggggca gcttagtaat gccttagtca ttgaaaaaca gggacctggc 18900
ctctctgacg agatgcccac tgtccaaggg tacactggtc cacagcatgg ccccgcagcc 18960
tgacctctcc cctcaccgtg gctctctgga tccttcaagg ggctcctgcc agtgactgta 19020
gtgggtgact ggagcctctt cccccaacgt cacacagcat gtgggctgga tgagccacct 19080
cccctctcag tgtcttggtt tcctcttctg cacaggggcg tcttggcagg ccctacctca 19140
aagggctgtt ggctgggaag attaaatgag atgatgagcc ccacgcacta tcatcaatga 19200
cgcttatgct tatggggagt ggggtgggaa gcacctctgc tctccatgca tgacttcatg 19260
aattcttttt ttttaaagat ggagtctcac tctgtcgccc agcctggagt gcaatggcat 19320
ggtctcggct cactgcaacc tccgcctcct gagttcaagt gattctcttg ccttagactc 19380
ccaagtagct ggcattacag gcgcctgcga ccatgcccag ctaatttttg tatttttagt 19440
agagatggag tttcatcatg ttggccagac tggtctcgaa ctcctgacct caggtgatct 19500
gcccgtctca gcctcccaaa gtgctgggat tacaggtgtg agccaccgtg cccggcccat 19560
ggatccttta acagccctct gaggggggat ctgtcctgtc tctttactga tagagatggt 19620
gaggcacaga gaggtgggga aacacccagg gtcacgtagc ataggagtgg cagcagcagg 19680
atttaaaagc gggtctcttg cactccaagg tccacgtgtt agccagtgca ccaggcaagg 19740
gataaaggac ttagtgtgag agctcctttg gaattggagt tgcagaggct ctggcttcct 19800
gtgctgatct cctgcaagcc tccagccccc agtcacgtct gtcagcagct ctgagagccc 19860
tccttgggcc tctcacctcc cacatgagca gggaatcagc aggcaaggtc cgggcggtga 19920

```
ggatgggggga tttcccgact cacttgagat ccgtcacatt aatgttaatt aagccttgtt  19980
aattcagccc tctgcttaca catggctcct gacagcaaat tgctcataag tgaggcagta  20040
aatttattgc tgctttttcc aaacatttag cagcaaagac ggtgccccag gaaaggcaga  20100
ggagagacct ggagggccag tgatgcttgg ttcctgctag cctgaacccc ccaggatcct  20160
catggcctag agaataaggt ggggctcccc aggagacctg ggtgagaatg aaattctggc  20220
ctgctcggag catactgcct ggagatgcgg tgagcactgt ctcagcacta actctctggt  20280
agctctgtgc tctgtgaaca tcccgttccc tgcgctgtcc tcccacagtg ccttgaagtg  20340
tgccctgcac agtagggctc agcaaaggtg tgtttggatt tggatgtgca gccccgagcc  20400
cacctccatg tcaggaaagc ctcgctgcag tgcagtctga taggagagcc agcagcctcc  20460
gcagggactg agcgccctgc atcctgaggt gtgcacctgg ggccagacca ctccgccagg  20520
gctgctggga aggggtctct ccctgtcctg ggtcatagga gcactgttgg aaccaggatc  20580
aggctcagat tctgggcctg tgaccccagc cccttgctag gctaggtatc tactcaccag  20640
gtgaggggga agcctctcct gggtatagtg ggacaccctc gtcctaggtc ctgcttcccg  20700
ccttggcctc agactgggtc gtgcctggac caattgaaca aacccaggct ttgggtacct  20760
agaattttaa aaaattaatt agagcattaa atggcagccc tctgggagaa tcccaccatc  20820
tggctgtcat gggagaggca agaaaatcta tgcatatttg tctgcagtgt gtgagcatca  20880
tatgaagcca actgtgcatg tgtgggtatg cggtctgtgt gctgcagtgt gtgtccagca  20940
tgacatgcgt gtctgagtat gttcagtatg tggcgcacac ctgagtgtgc aagtgggtgg  21000
tgtgtgcctt gctgtatgca cgggtgccca tctgcaagta catgcgctgt gtgcatgtgc  21060
ctgagtgtct gcacgtctgt ctgaacatac ctctgtgtgt ggtccatgct caggcctgcc  21120
tttttggtgc agtgagccag gctgagctgt gtgcagatag ggaaggggct cgtgactcct  21180
cctggctgag gtggtgggca cagacagctg tgtagaaggt gggacggggt aagtgtggca  21240
agtgcacagc tggccttcag tgggtgaggc agggcaggca tccttgccct catttgacag  21300
atgggaaaac ccaaaactgg agcctgggct ctggggctcc ctgcgtggtg ctctttctgt  21360
tccagcgggc tgctgccctg gctggcacct atgcttttgg catctttatg ctgttagatt  21420
ttcatggtgg ctcaaagtgg ttctgagaga gtaccacccc ccctactcag tattgctcag  21480
ggggcaaggt caggattccc actgcacatc ctgtgttctt cctgtttcaa ggaggagata  21540
tcagggctgc tggagaatgc tgggcctgat agtcctctga ctgctgtgtg acctgggccc  21600
atcctgtccc tctctgaacc tcaggggtga ttgtaagaac taaatgagga gacatataca  21660
aagggcttcg taaaccagga gatgaggtga ggtgatgtag acagatgagg gcctggccca  21720
gagatggcat cacaatacga tcagagccaa agctgaggcc caagttcatg tgtcccaggg  21780
tttcctgagg agcaggccag gaggtgggac ccaggacaga ggcaggtgcc ctcccagcct  21840
tgcagactct gaacctgtcc tcagaaccat ctgcctggtg ccagcactct cctccaactc  21900
cagccccaga cacatggctc atggcagtga agtaaagcag gaacagaccc agggagcagt  21960
gggatccaac ccctcaactg gtgttgacgc tgaggcccag agagggggag tggcttactc  22020
aaagccacgc agcagctcgg ggggtagagc tgggaccaaa acccaggcct cctggcccct  22080
ggctctgttc tccttggtac cataccactg tctttggcaa gagaaagagg acacaagagc  22140
tagttcacat gcctggagaa aaggatgtgg gagtgccacc cagctagaca gcactagaac  22200
agaccagagc cccacttcct gcatgaatgg aggatctgaa gcaaggcttc aatgattact  22260
```

```
gcttttccta ggtatgcaga atgctggagg gtaaataggg tttgtgtcct gggctgtaca  22320
ttctgtatag atggaaaagc cccaggcttc cagattgcct gcatgcgatg ccttcagcac  22380
acgcttcctc agtgcctgcc tccaccgagc tgctagtctg gtagagaaag atggttgagt  22440
gccaccaaca caggatgatg aggctgtgga tcagaagagg tctctgatcc cacatggggt  22500
cgtggaaagc ttcccaatag aatagagaag gggaggaggg tcctccactc ccaactccca  22560
gagagtgagg aatgtgtgcg cctcagacac cctggccccc tggcagtctg ggcctcataa  22620
gagctcatgc ttgggcaggc tcaccgttca ccctggagtg ggtggctggg tgccttccag  22680
cttcctcctc agcgcctctc ctgtgccagg gcccatgcac gtgggtggag gagaggccat  22740
tctagaggcc cctggctccc tgtggggctg aggagagact agtgtggggg caggggtgga  22800
ggtgcaggga agctggtggc cagacctcct gtgacctcca ctcattgcct gtgtgtccag  22860
gtgggccagt ctcagctgcc ccgcttggcg ttataaccat tgtggtgtta gccagggacg  22920
aggcttctga agtagcctgc actgtgagcc ccgctggctg ccaggtaata attccacccg  22980
ccttgacctt tttctccaag gaacaggcct tctactttat acatggagaa aacaagtcac  23040
agaagaacca ggtggcccag gatgacagag gctaggcctc cagatgccct ttaaaaattg  23100
caacaaaaac ctcttaagga ctcactgtgt acaaagcctg gtggtggggc tgccacagcg  23160
gctgggataa agggaggagg aacttcggtc actgaatatt ttctgtgtgc catcccttat  23220
gtcgggcact gatagacgtg atctagcaac caactgccct ccgagtcagg atctaccacc  23280
acatttttaa atgaggaaac atgggctcag agcggtcagg tagcctgcct gaggtcgctt  23340
agctagtaag ggacaaaggc gtgatttgag tcctgcgttc cttcacctgt ttttgtggga  23400
gaatggccat gtcaggcagc agactgggat cttccaaacc ttagttctgg gaggaaggtt  23460
cacttgcagg aaaaaccaag gtgagtggaa tcatcttcag gcagccagca gtgctcactg  23520
ggcaggctgt ttaaaagtgg cttcctcttc aagctgtagt gggacctgtc ttactggggg  23580
agccatgctg gctcagaacc cctaggctga tgggcacccc tctgtaaggg gctctgagaa  23640
gtggccggtg tggctgaggt ctgggccagg atgccagtgg gcggtgaggg tttgctgggc  23700
acatgacccc acacctttcc tcttcttgcc tcccacagcc atgtctgtcc ccttctgccc  23760
agctctggtt ggaggtgctg agctggggct tgtggccatg aaccatcccc atactgctgg  23820
ccctggggct ggcctcagat gggtgggtgg tcccggccag agccctgaac cccggccctg  23880
ccagaaccaa cacctggaga catggccacc tccgaaggtc ttacctaact gcagggcgtg  23940
ccagcatcta gcagggtccc tcacgcacag ttggcctgct gcttgattat tttggcttcc  24000
agcagcagag acctgagact ttcccggtag cataggagtc agcagaagct tggccttccc  24060
agaacatggg accagaggag gtgtcctgga cagggccagg tgaggggagg ctgctggtgg  24120
cccctcactg agcctttctg cagtgggcct ggggaccccc tctgccctga gcatttgcca  24180
agcagtccag tggctgcgcg tgggcctgcc tttcctcccc cactttggca tggctgtctc  24240
ccaggaaacg gggaattttc cctcattccc atcattaggg tgccagggca aacaaacagt  24300
ctaatccaga tgagccctgg gccacaatca cactctcttt gggggttttc tcttcacttg  24360
gagcaatgtt gagaaggctg gagtaattgg tattccaccc aggttaatag aactgctgcc  24420
tcctcggtat tatgccttaa tttcctttat cgctcagcaa gttggaattc atcgcccctt  24480
tcctttcttt ttcccaccga aacctatcac cagcctgtct gctgggtaaa gtcatttcat  24540
ggcagctctt ggctcctttc cacttccctg ggagtctttc tgaccgagcc aaagaacaag  24600
gaggggtgaa aaatccattt gtacaaagtg ggatctcct gttgagagct tatttccctc  24660
```

```
cccgttcaag aggaaggaac gtgttcagcc tccagccagc acggctgact gagtcccctg  24720
tcgctgagag cattcaagag ggcgaatggc catatgtcag cggtgggaac agaggattcc  24780
agcactggtg gggttgggg gaaaggggca ggcctttgcc actcctggtg cctggattag  24840
attagaagct tctagggttt tgttctgttt gtgagtctaa gatttgtgat ttaaaactgg  24900
aaagattctg tggctccttg gtcctaacgt tcaacggaat gagcctaagt acttgtaaat  24960
tgtgtgtttt acgattctca gatcctgaga cagggagatt ctgttctgtg attcgaagac  25020
tatcttatga ttcctccagt ctcttcagcg gcagttttgt tcctgactgg gtcttgggag  25080
gagtgcaatt gctttgctga ggttgccatg ggagcgcgag gctgctgtgg cccctttttct  25140
catgtatgaa atccaagggc tgggccacat ggccctgggg cccaggtgtg ttcagcctgc  25200
agccccttg gctccaccag agcctcccac aggccctgtg aggactggct gctccccacc  25260
acctcactgg acccagatgc ttttccagct aagccatgcc ccttgcctgt ctgcccccgg  25320
ccctctccca ttcgaacggg gaggcaaccc agctctcccc aaagtccctg taggaaagct  25380
ggagcagtgg gggagtggtg gtggtaagaa ataagccgca tgattgacaa gagctctacc  25440
tgcttttgtg gtgatgtgca atttcaccat gaatttcaac attacaacct ctcttaattc  25500
ccaccctctg aggtggttag ccccatttta ttgttgagga agctgaggct ctgagaggtt  25560
aagtcactca cctataatca tacaggttgt tcccaggccc tgactctgga tcacctgctg  25620
tagtacggct ctaggccgcc tgggcagcat gatgaaactg tctctacaac aaaaatccaa  25680
aaaaaaaaaa aaattagctg ggtgtggtgg tgcacgcctg cagtcccagc tacttgggaa  25740
gctggggtgt gaggatggct tgagcctgca aggttgaggc tgcagtgagc tgaaatacta  25800
ctgcactcca gcctggccaa cagggaaacc ctgtctccaa aaaaaaaaaa aaggcattga  25860
ttggcccaag gtcatatggc ttgaggcagg accagaaccc aggtcatctc attcctaatg  25920
cagtgcaagc aaaggaaaaa gcgagaggtg gacattcatc atagagtcta tagccaaact  25980
gaggaacaaa aaccctgggt gtaacagcca caacccagaa caaaaggaga tgggtcttgg  26040
ttagactccg ggtggtgac gtcactcatc tcccctctct gggcctcagt gccccggctg  26100
taaaacaagg acaccgacct tggtggtctc caagcccaca tcatgttagg ttccggtcta  26160
acgtgagccc gaggctggga atctgcttgt tgggtggggg ttgtggacca cacgcttaca  26220
cctccctgtt ggaaccaatc ctggggcggt taaagagctt cagagaatgg accccatttc  26280
cttccaaacg cactgagaag ccagaagcag ccttctccat ctgctttcag aatccacctt  26340
ttccttctgg atcaaacata gttcctcggg gcaggcttcc tcagccccta ctactgccag  26400
ccaaaatcac cccctttctt tgaggaccag cttaaaatgt ctctcttcca ggcagtgagc  26460
cctccccagg cctgcctcct ctccctccag cagaccttac tcacaggcaa gggagatgca  26520
ggcttggaga ccaccaaggt cagtgtcctt gttttacagc tgaggcactg gggtccagag  26580
aggggagatg agtgacgtca ccaccccaga gtctaaccaa gacgcatctc cttttgttct  26640
gggttgtggc tgttacacct ggggttctcc tttcctcagt ttggctatag actctctgaa  26700
ggaaggtcca cctctcactt tttcctttgc ttgcacagca ttcgggatga aacaacctgc  26760
gttctggtcc tgcctcaagc tacatgacct tgggacaatc aatgcctttt ttttttttta  26820
agacagggtt tccctctgtt gcccaggctg gagtgcagta gcatgatcat ggctcactgc  26880
agcctcaacc tcccgggctc aagccagccg accaccccag cctcccaagt agctgggact  26940
gcagatgtgt accaccatgc ccagctaatt tttttggta tttttgttgt tgtagagatg  27000
```

```
gggtttcacc atgttgtcca ggctggtatt gaactcctgg gctcaagtaa tctgcctgcc  27060
ttggcctccc aaatttctgg cattacaggc gtgcgccacc atgcctggcc agttcatgcc  27120
ttttaaggtc tttgcttcct aatctcttaa agtgggtggt ggcttctgcc tcacacccac  27180
ctcacagctg ccctgaggag ccaggccgag ggactgggga tggagtctca aacctgtcac  27240
tcaactccat acccgctaag gacccagggc cagtctgcta gatttctctt gggctcaggg  27300
agtatcccaa tcagacaatt cccttgttcc ccaatgcccc catgatcccc acctctgagc  27360
cgaaggttct caggagcccc tggcttcagg gcccttccac tctctccatt gagcacctgc  27420
cctgagccac gtgctctgct gtccgcatca cccagcagca cacctgtctc ccctcccgga  27480
gcgggtgctg actacactgg cccacaccac tccaccccac cccccacacc tcgagcaccc  27540
tccttctgtc cctttcactc tcaccttgtg aggtaaccca ggcaggcctt tgaatggtac  27600
acatgaaaac ctgactcctc caatgtctag gtgaggaggc tgaggcacca gagggtaagg  27660
ggcatgtcca atgtcacccc agaggtcaag ggcagcctgg aggggtagcc agggctcccg  27720
aggcccaaac tactgagacg gtctggaacc caggcagggc tttgtggaac tccccagaga  27780
agccctgtga agggctttct cacaccgagg gcccagcttt cactaggaga ctgggaaggg  27840
tttgcatctc cctgagccct gctttatgac agtggccgag ccacgtgtca ctggcttact  27900
gagctgctgg gatgacttct gagcctagtc cggtctggtg gatggctcct gaggtctccc  27960
ctggccagtg gggccgcaga tcttcatctc agcactgacg gccagggtgg gcacagcctg  28020
gaaggggctt cccgtaggca ctgcctgggt cggtctgcca aaatacagca gcaaaataag  28080
caccccatgg agactcgagc ttgctaacgt cctacctttg gtgttgtggg ccctggctgg  28140
ccctgggctg ggatccactc atttctgctc tgtcagaggt gggggcattt ggatgggggc  28200
attgtcagac accatgaaca gctgatgctt gagctggcca tcaggggtgg gagagttttg  28260
cccatggagg tggaagaagg gcttctggcc tgggggagct gcgtgagcaa aagcacctgg  28320
tatgaaggcc aatggcttgt ccataaccat tgagtggtta ctggaggcag gtgatggcca  28380
gggatgggcc agagcagtag cagggcaggt tgaactgttc ctgagtgccc tgctaaggca  28440
gttggtcata ttcaagggga gatgggaagc cagcaggcaa ggaaagatgg ctctttgatt  28500
acggagagga ctttggtagg acagtgacta ctggctctgg atttgtagcc cctggagcca  28560
caggagtgga ctgtaaggga ctggggacca agccacagtt ccctccctct gtcagcccac  28620
tctgggcctg gtggtgggta aaaccatacc taaaaaggag aggaacttag agcttatctc  28680
atccaactca ccatgccatg aaagaagaga gcaaggcaca gagaaggcca gagacttaca  28740
tcaaggccac agagcagagc caggccctcc aggccaggag tggcagacgg cccattgcta  28800
actccattct cagtgagata ttcttaacct ctctccagaa aagccagcag actccctgca  28860
caggcctcag cgatatcaca gagtgatact ttaacctgca gaccttctgc tgggcacaca  28920
ggtgggcaca ggtgggcaga ggctccctgg atgaccaatg tgaggctggg ggtggcagag  28980
agctcacacc agcctcctgg gcacagcctg ccacacactc cctggtgagg agcccagagc  29040
ccagcacaga ggagcactcc agagaggcag cagtcccaca ccaggagatg gatttcccaa  29100
taacaggtgc tgcccattta tcaccgggat gggccagtga ggctcctgct aggaaatgct  29160
tctcctacca gcctaattgg tgaaagcatt tgcgtttttc actagccagg gctgcttcct  29220
agtgtgtgca gtctctacct ggtgggcaga ggagagggtg ctgcagcgac ccactgctga  29280
catcagaggc ctgagtgccc tgcctgcctg tgggtagcag ccagggaccc gccacccctc  29340
cccacacagg caggggtcat cactgaatca tttgctccac acaggcagag gtcatcactc  29400
```

```
aatcattcgc tccacacagg caggggtcat cactcaatca ttcgctccac cagaggagtg  29460
tctgcgcctc gtgggttctt gaatccctcg ggcctggcct ccttggccct ggctgcagag  29520
ttctgctctg ggagccctga gcttcccact tacagttagt gggggccgag agcccagaga  29580
ggcctgcccc ttgtcacaca gcgtgttggt ggcagagcag ggctggaatg agatctagaa  29640
ccttctcctc aactgcaaaa gaagaagcgg aagagctgcc cctccttccc tcagagggct  29700
ggtggcaaga acagggcctg gaatgcaggg gtccttggca agctccaagg tcagcctgcc  29760
caagggaggc ggagctgtgg acccatcagc cccagggggc ctggctgggg ttagccagga  29820
aggtgccctg gtcagaggag gccacgtttc cactggggta ggagtggaag gggaatgtga  29880
ggctgggagc ctggcaatga ctctggctgg agggcctaaa gggtctcctg gccttgcctt  29940
ctggcctctg gaagcttcta ctttaagaat gtcatgagtt ttcttctagc tgtttctctg  30000
gaacccacaa tcccagtgcc aaaacccagg gtggggctgg ctggagcctg ggagagggca  30060
ggaacgtggt catcttctca gcgtgctgcc tgctctcagc agcacccctt gcgtaatgct  30120
tggtcccttt gcaggcgcca gccagggact cctgctgatc ccatcctgcc cacctctccc  30180
ccatacccac ctcctcccag cccctcagct gtcactcgtt caatacctcc tgcaaccaca  30240
aatcactggg acaggaagac gcctttgtcg gtctgtccct cggagacgct cttcttccct  30300
gtggtgacag ggaggcctac ataccccagc aagggcttgg gcctcccttg gtgacagtgg  30360
ggccagggtc cggcagtatc tgagagcagc tgggatgtac tggggcctgg aggaggtgct  30420
tggttgtggg aagccccaga tgacctcttt ggaaggactt ggaacagcac caagatccac  30480
aacccctccg tgtgacgggg tcactaatcc agaaggtcag ctggaggggg cccttagaga  30540
tgtgttcacc tgaggaaact gaggcccaga atgggaaggg gtgacactcc ttccaccgct  30600
gggggccctg ctgctgcctc ccattttgtc tttcctcggg cctcctgatc tttgcaacct  30660
cattttcatg ccttggtgtt ttggggcaaa ggtggaccac ttgtttcatg tttggaccac  30720
ttgtttcttg ggaaataaat agatttatgg tcttaggatc tggcttggtt agaattgtgt  30780
aactccttag tggaatgggt tggaggagag aacccagaaa attttgaggg aaactcttcc  30840
cgatttgaaa gcaaagccgc cctcaccaaa aagtgctcct tccgctgcag cctcttcatt  30900
ccgaatgggg tgaatccttt ggctggagcc cttcgtgtgt ctccctcctc ctcagcacct  30960
gcagcttctc agtctcccca ggtgggatgg gaaggtgggg gagagggcga atttagatgt  31020
cgcctgctga tggatgatgg tggcttgagc cccagagccc gctgggcagt acaaagccac  31080
gcaccgagtc ccgcccacca cacgcgggtg ctggctcctg caccctactg tcaggacact  31140
gtgggaaccg ttcgccttct gggaaccgcc gagccttgag tagtcagaga ctgtccgcat  31200
gtggacttct ggactcagat aaacagttcc tttcagggaa ggcatcagag gctgccatcc  31260
gcagcttatc gacatctccg actctggcgg tagctgtcat ggagtcttgt cacaggggct  31320
tagggtgcaa atcagagtgt tacagcctta gaaccgtagg tccctagagt gtcagaagca  31380
gagccatgtg gaagctgttt gcaatgttat aatggaccca cgggatcttt aaactgaggg  31440
ctttaggaac atcacatgtc cagggagggg ttaggatttg aatccattgc tgctggaccc  31500
cagatctgct ggcgatggag gatttgaatc cagtgctgct ggaccccaga tctgctggcg  31560
atgggctctg ggcatcaccc ccaccaccac ttccaaccgt gcagctccat tttaatctgt  31620
cttatatgtt gggggttcac ttgggaaaag ggttcctctg cttaaaaata gttttccagg  31680
ccctgtgctg agccccagct ccatgccagg acccgccaca gcctgagagg gtggctctgg  31740
```

```
tagtgggacg gccgtcaggc cagggccccc gggtggggtg caggttgctc tgggccacgg  31800
tctcctcccc ctctcattac tgctctgtcg ttgctgcagc cagagaacac tctgggtctg  31860
tcatcctgtt gactggggtg acagtttaat agtagcttcc tggactgtca tttaaatctg  31920
cctgccaggt tagtaggcca ggggcgggct ggcacgcccc ctgcccccac cccggatctg  31980
cattctgctg gaagcggtcg tcttggcaac gctggggcat ggcgagctct gtcgaagggt  32040
aactgttggt gggagcagcc ctttcatctc cccgacccgg gtacaagtgg cccaactgcc  32100
ttagggccag agccaggcca ccctgtgctg gcccaggcct gggagaggaa gtgggaacat  32160
ccaagtccct tctgtgcacc cagctctcca agttaggggc tttacctttg ctctcagcct  32220
ctcaactgcc ctaggagggg aaagaacctg ccccagcttg ctgaacaaca atgttgagct  32280
ggaatccacc tttcttaggg gtcgctgctc tgccttcaga gaacattctc tagagcccaa  32340
gacctgtcca cagaaaccag agatcagtca gagcctgtaa ggctgacagc tccctcatct  32400
ccctgtccta ggtggctggg tatcaattct ctctgttctt tccagggcct ttctctagac  32460
gtgtccctgc tctgaggatt ggggtctcca gtggggtccc tgcagcttca ctctgggctc  32520
catgctctgt gaacactttg ttctattttt tatggcctag tggggctggc ccagagacag  32580
acggctaagt acaactacca ggctgctgtg tcaacacggg ctagtccctc ccttctctgc  32640
acctcatcta atcatctgta ggatgagagg cttgtgcccc agcagtgttt tcctaggtgt  32700
ggttcattgg accacttgtt tcttgggaaa taaacagatg tggcatctga aaaaggagtt  32760
ccttggttaa acaagcttgg aaggctggag gaaaccgtca atcagatatc tttactgcag  32820
tccttcccag ggcctttata aaccgtgggc atcatgcatc tccaaggggg aaaataataa  32880
gtgtctatcc caaatatcct ggtgcatggc cacccctggg ctctgtcctg ccccctaccc  32940
ctcccctcct ctgctaaggg ccgattttct gtcttgcatg gcctcacgaa atcccaaagg  33000
aagctctggc agcctggagc cctgggtttt tttggctgct ggagagcagc cctgtgttta  33060
gcaagaggct ggatgggtcc ctgggcaagc tcaaggaaag ccaggcccct gtgctgggcc  33120
tctgcagggc agctttgtgc acaacttggt gaacaactcc accagggtca attgttccct  33180
ggcctggtgg agctccaggt cccttgccac ttgccttgtc cccagcccct aatggtcact  33240
ctgctcgctc ctccatgccc ctaagcccca ttatccttcc tcctggaatg ctcttccctg  33300
ctctcttcac tcccacagct tggctgactc ctcttccttg aacacagtgc ccctcctctg  33360
ggaagccttc cctgacccct gggccaggtc aggtggccct cgcctggctt gctggctaca  33420
aagtgggatt gggagtcatt acctgggttc aagtgcagcc ctcccacaga catgtgctgt  33480
ggctttgagc agtcacttct cactaggcct tggcttccag gcatgtaaca tgggagaccc  33540
acgtaggggg cctcaagacc ctggagtcca acacggcagg acattcggat tgccaagagg  33600
aagctgcaca gagcagtgcc cctgggcagc ccggactaat ctttattttg gagccttctc  33660
tctgcaccgg ggctccacga tgcgtgtggg tggggagcag catgggaagg atgtatactg  33720
tctcagggaa ggatgtctct ggaggcgggg gaagccaaga agtgctgagt gattctaaca  33780
gtttcacagg atcacagaca ctgagtgtgg agagggcctt aagacttagt cagcgccaca  33840
cctccatttc ctgatgagga ggaggcaagc tcagaaggtt tgacggatgg gcccagtgtt  33900
acacacacgg cagctggggc cagggctgtg acttcacaca cctctaactt gcaccttttt  33960
gcttctcagt tcataaagcc ctggggccat ccttagctta tttgcttctc acaatgaccc  34020
tgtgtgtccc gtgaagcaga cgaagaaagt gcggctcaca ggagtcctgt aacttgtgta  34080
aggtcacata gcctacaagt ggcagggcgc agtttgatag accatggact gtctggcact  34140
```

ttccttggcc cgtgttcttg ttataaatag catttcccac ttcctttgtc ctggatttcc 34200
cactctcccc tactctaccc tggggtcagc ccctcctcac tgcccctaga atcccctagt 34260
cctttgtggc agcccatctg ttgccatggc accagattat gatgtcgcag accctggttg 34320
actatgtatc actcctgggc tgagggactc acagaggtgg gcattgtcca aggggcagac 34380
tggcatgggg ggacataaat ccctggaaac agggagccat ggccttgagc ccagctgggg 34440
aatcaccctg ggaaccagag ccaaggccag cagagtaggg gtctggcatg gctttctctg 34500
acagccttag aatggcggca cagccctcat ctcatggcag ggctgatatg gtctcttcac 34560
gagggactat tgggctcatt gcactgaacg gcctgacact gggtgttcac caggatcccc 34620
cagaagagtc tttttgcctt ttgtccttgt gacaaagctg catgggaaag ccacatcccc 34680
acttgcccag gttcaccccg aggtggctat gccaggagtc agtctccact ctgactccag 34740
atccttccat atggtcacac ttccaatggg gccctccagc gtgctttagt ctagtcccca 34800
ccctgaaagt gctgtccatt agcagagcaa aagccgtccc aggcctgggt ttattctgct 34860
gcacacttct gggcacattc caggagacct gagagatgtt tcagtacatt tgaggactct 34920
ctggggtcct cattcttagc ctggtaacac tgaggtggct gagggtctga gtggaaagag 34980
atcaagcttt ggcagctgcc acacacagtt gaaatcacac ttctgccacc taacaccctt 35040
acctctaagc cttaatttcc tcttctgtac aatgggatta ataacaacag ctaccaagat 35100
agctgtgagg agtcactggg atattgggtg aaaggtgcca ggccagagcc agagtggaaa 35160
atctccaagc tggtccagcc agtgaacaaa tctgttccca aaaacaccac cgaatctgtt 35220
gccaaaaaca ccactctccc tgcagctgcc atttcctggg cggggctgac ctcaaagctg 35280
ccctttggga cagcagtggt gtttttggct gctctggcct ccttgcccag tgcctgccag 35340
ggcttggcac atggaggagg acaagatcac ccccaggctt tcagaatccc agggagggca 35400
gggtttttgg ggggtatctg gttgtcctgt gcccagcaac agagccccat catcaccttc 35460
ttcaagcctg ccctgctgtt ttgggcactg tctgaccaca catccttgcc agacttgcct 35520
acttgctctt aattcccaga gactgggctg ggctgattct gtgttctcag tgcagaacgt 35580
agaacagaag caaggttcat tgaatgtgga actgaagctt gcacagggct ttcccacctg 35640
ctgtaaggtt tttcttccac atttggtact gctgaatgtt tgactgggga gccgtggtgg 35700
agatgagcag gcatctgact gtgggttcag actgtgaccc tgctccccccc agctgtgacc 35760 ttggacatgt aacttaacat ctctgggtct ggatttcctc atatgtcaaa tgagtacata 35820
gcaggccccc tgccatgagg tttcttgggt aaaaacacct ggcagagact ggcacagagg 35880
aagcacctag tgagtgttag aacgagaaaa agagaaaact aggatatacg tttctttttt 35940
tggatgctga gcttcttgtg gggggaaaac cactggtgtt cacattagga aattccccag 36000
gtgctgtggt tcatattggt acttacttta agatgattat ggactatgat ttaccaatag 36060
gtggtattcg catctatcat tgacgatgac ctctcagtgc aggaaacagg gagggcctct 36120
ccagagccct gggctgagag gcaggagagc tgttcttatc cctgccatgc tgtatttccc 36180
tcagccagcc cctttccctt tctgggcctc aatctaccca tctgaaggtg gactctgatt 36240
cctcaggttt cttctagttc tgcacgtaca gaggcattct tctaagcaaa gtgtgaagaa 36300
aactcatctt agaatgcaga tgtactgcaa agattccact gagaaggaca gacatggaac 36360
agattcagag acacagtctc tctcaccaaa tccttgccag gctccccaga ggagggggag 36420
caggcctgca gccccagaag cacccagagg gcctgtgggt agatttgaat aaaggtggtc 36480

```
catgggagtg gcttcccagg gagaaggcaa gccccagaac tgtaagtatg gagcagaggc  36540
tggggggctg tgctcgcatt tagctcagtg tcccgcactg agacctaccc caagctggat  36600
tcttgctgaa tttgacagtc tctgtgctgc agggacaggg aagaaagcaa accatgttgg  36660
actcgcaatc agtgatgatc tagagcagag gtcatcaaaa tacaggccac aggcctggcc  36720
tgtcaccagt tttttgtaaa taaagtttta ttgaaacata accatgctca ctcatttatc  36780
taatgtctct gactgcttct gccccatagt ggcaggattg agtggtgtga ccgagaccat  36840
ttggccctca aagcctaaat agctactatc tggcccttca cagaaaaagt ttgccaacct  36900
ctgccctaga aggacattca ggggattgta ggagctcagg agaggctact gatcaagact  36960
ggaggtgata cttaagccca gtgtgtaatg gaaagaaggt gagaggtggg ggaaggggct  37020
ttcagactaa agacagcttg ggcaaggtat gatggtataa aaagcatgga gtatatgagg  37080
acccaccggc agttgaggtg gggctagatt gggaagtatg aggaggggaa gatgagggag  37140
cggggcaggc tggggccacg ggacttctaa gcccctgggg agaggccaca tcctagtggc  37200
ccctgatgtt aaatccatcc caagctcatt ccaggggagg actttggtgg tctgagcgcc  37260
ccaaggcctg ggtaagtca ctgctgtgct gaggtatcct cttttaggct gaaaagagac  37320
ccccctgccg tcttcatttc tggcctcct ggtctcgaac taccacacct gaaagcttat  37380
ctctcaccag atcaccctct cttttcctga tgaagaagct gtaggccaga aaagggccat  37440
gatgtgcttg aggatacaga gcaaaatagc acagcagtgt ctcaaatcca gacctccgga  37500
ctccctgccc agtgctctct tcctcacctt gttctgtagc gggtcctgga tgcttggtcc  37560
agcaggaaca gggcatgtgt gagttcaatg cagatttgat gcagatgagc cccaataat  37620
tcagaggcct agggctgcta cagagggtgc aggatgtcag ggtggagcg ctcaaggccc  37680
cttcccggtc tccaacaccc ccgcaccccc accacctact gggggtagcc aggcagcctc  37740
agttccccca tggaagtcct gacagggcaa ctgctctccc ccgggcctgc taggtgcgcc  37800
cagtgctgtg ctgctgcttg ggaagaagct ggggcacctt atgacatggg catccatctc  37860
tgtttcctct cattgatctg gaaactctag ttcctcgtag gacaagacac agaaggcagt  37920
aaagaaccgg gctggggatg gtacctgcat tcttatctca gctccgtaac cagctgtgag  37980
ctctcagcct gctacatccc ctgtgtggac acagaacccc attccttcag cttctaatta  38040
agactcaaac cctgaaaaca acagtagctg ccacttctcc agcatctgcc atgtgcctga  38100
gtctgctgca ggttcttcat acattacgac ttcttgttgc tcctcctcac cgccttttgt  38160
cttcttctcc ctattatata gataagaaaa tgtaggctca gagattaagg aacatcctca  38220
aggtcacaca gataggagga ggaggaggag gaggaagtgg gattgagatc cccagagcag  38280
tgtggaggtc accctgcagg ctgtaggcac cggggggcag ggactgattt gggtgtcttg  38340
cccagtagat cctcttccga ctgctctgaa cacaaaatac gtcattcatc ttgccacaaa  38400
ggaatcatct atgtgtagga ttcatgatca caaactcccc tggcgcctgc agaagggact  38460
ttgacttcca gtccagttgg ggaaagtggg acaggcaggt aaagagactg agaactggct  38520
gaaggagcta aggcagctgc tgtagggtat cagggaaggc ttcctgggga cagtggcagt  38580
ggaactagac attgagggga agcaggagtg tggtggggta tgataaatct tgtcatgctt  38640
gctgggtttg agctcttgga cttggagggc agagcagaat gtcacctgtc ttcacgcagt  38700
gttcagatgc ctaaggaatg aagaagcttg tctctcctgt cctctgccct tggtcagcaa  38760
ggcagtccat ggcctggttt gcagaccaag cacatcctgg tcggcccacc accctcctga  38820
ctgctcccag gctcaccacg ctctcttcct tgccctgcag ccaagaagac ctgtgcagac  38880
```

```
agtgacttca cctgtgacaa cggccactgc atccacgaac ggtggaagtg tgacggcgag  38940
gaggagtgtc ctgatggctc cgatgagtcc gaggccactt gcagtgagtc ctgcccctca  39000
gtctgggtgg gggtgggcct cagtttcctc ctcagatctt ccttgagagg ctgtgaggct  39060
caggagaggt aaccagttga acattctgtg ccacgcactc agggcgctcc tggtaaacag  39120
atatatttag ttgctggttt ctactgacct gtttctggac tttcttcaca gccctcttgt  39180
aggttggacc ctgtttctgt ggcagcagga gctagaaaca gccctgtcaa gcccttctgc  39240
ccagaaggag ccctagcgtg tcctccaggc ctccctgctg ctgttcttga ggaccccgac  39300
cataattcca ggagtgccag tggcagctgg tgcttcttaa gcctttatcg tgtgctaagc  39360
tctctgtgtg cattaatgcc tttgataacc acagcagcct catgaagcag atactgtcat  39420
tttctgagtt ttgtaacgga gaacactgaa gctcaaagag gttgagtgac ttgcccaagg  39480
ctacccagcc aagactttga ggctctggcc cgttcctcta ccctgggtgg gctgagccta  39540
ggagctcctg cctccatggc cagctgggtg gtagcagagg caggcagggg gaggtagagg  39600
ccagagctga gccccaggcc tgccccctac actcagggct ttgtctctcc atgatttatt  39660
ttccaggccc taatcctcaa agcaaactta cacccggcag gtcattctgt gacatttgtt  39720
aaattaaaaa ggagatgaga agggggcggg gaaggaccca gcagtccaga ggcagagctt  39780
cagcagcgtg agcccgagac aaaaggctca ggcaaaagca tgtggaggat agtggggctg  39840
gcggggaccc aggagcccct gtttaggggt aacagtcgtc ccagaggcag aggtggggac  39900
aatggagacc ggagtcccat ctaacgccgt ggctggtgat aactgggttt ccttgtctcc  39960
tagcaacaga gctaccagtc tccacataag agaaagagaa agggagagag agagaacaga  40020
gcaagagcgg cccccacccg agacaaggag ccctcatttc ctcgtacagc tgctcctggc  40080
ctccccagcc atgccgcagg ccccatcctt tccttaccca ccacgtggcc aaactccatg  40140
ccgtcctgaa ggctcccagg caggagggaa gcccagtgct ttgtcctgag cttcagaagg  40200
aacaaagccc tgccacgccc acttgtgact ttcatcctct tggcaaccta aggaaggagg  40260
aggatcccca tgtagagaga aagaaactga ggctggagtc agttctcccc cttgcccaag  40320
gctgcccagc taacaagagg cagagtcgtg tgcagcctgg agtgtgtgct tggggagggt  40380
ttgtggccac agggagcttt tccctcactg cagtcagcca gctcctccat ccgtacctca  40440
ctccagcaga tactccgaca atgggggcag aaagggaagg gagaggagcc tcatcgtggt  40500
tatcagaggg ggctgccttg ctacctgagg gctaggctcc ccttctcccc ctgccccacc  40560
cccacccccg tctctatctc tttgtgtgga tgtccctttt catcttccat tctgtcccct  40620
tcggggtccc gcccacccct gccctcttgg gctgcctccc ttccctgctc atctcctatc  40680
ctcaccctcc ctctcaccat ctcttctcac tgccctactc atgtgtccct ctgtcttttt  40740
ccctcttgcc catcccagca cctgctgcct tcccatcccc tgggctgggc aggggccctc  40800
ctgcctcatt cctcctgcct cccaggcccg cttttcacag ttgagggaca acaggaggcc  40860
cagagaagtt gatagacttc cttcaaaaac acacagctta tccatggcag gtctcccttt  40920
tatgaaaaaa ggctcttcga gctctctgag gtttcataag gcgtctatgg gagcagtagc  40980
caaggcagca ccccaggaga cagaagccca gctctcctgt gggctcttcc agctactcac  41040
tgtgaagccc tgcatatctt cccacctccc tctgggccct gatcagtaac actccggaat  41100
tccagaatct tctccattcc tagattccta aactcttagt attctgagac cccctttccc  41160
ccttgcttgt gctagctggg gtgcaagagc catgataccc acttcctgtg ttacattggt  41220
```

```
cggtgtaggc aaggcggaag actgcctgga ggaagttggc tagagtggga gctctggtca  41280
gggtcaggca gaatttgggg cagcaggacc tgatagcagg cttgctcact gcttcccaac  41340
tgaatgagaa cctagcagcc aacctgctat ccatttaatt ggtgttgcca tagcaacctc  41400
cacggcccac caggttcctg gggctatgcc agctcccagg atggagcccc attccctacc  41460
cctaaaagaa agattatagg cagtaaagtg tagtgagttt gggattggat atagttgggt  41520
tcaggtcttt taacctgtta gacctcgggc aagctgccca gtcatcctga acctcagttt  41580
actcatctgt aaaatgtggt aatggtacct gccttagagg gattgtgaga atcaaatgaa  41640
agaatgcaag tatcatcgct ggagtaaatg gcagtgttat ttgtattatt atattttggc  41700
tgcaagcccc ctctccccaa cacaacagtg tgttagatat taagatgtta gattcttaca  41760
gtgttaaaat agtgtcagtg aagggagttg cattgagcgg gaaagggatt tgagagaagg  41820
tcccaattct tgtgttttcc ccgattatgt tgtctgtccc tagctggctg gggtttctcc  41880
cagctctgtt tccctctggt tctgtgttct gtacctatca aatgtagcca ggagtcacaa  41940
tggaaaagcc cagaacattt gcctaatggc aatagcattt cagctctaat tatagctcac  42000
ttgattgggg acggcttctg acccaccttc aggcttctgt tgggaggggt gagggtgggg  42060
gaggggagga tggttcaagg tgagttatag ttctggatgc tatttatttg aatatggagg  42120
ctttttcatg catcttagaa cctttccacc tgggaggggg gcctctctga ttaaccaggc  42180
tcatcttgct attatagatc agaaaatgga ggcccagaga ttttctgagc tcactcagta  42240
agttagggac tgacccagct agcagcattt tgcctggcct tgactgaagg aacttggtgt  42300
aactccccct tctgcacctt gggtggcccc atgctgtgct tcctgtggat tgagtgacac  42360
tggcagttct caccaccgga gcctctggtc ccttagagct ggcagtcccc atttggaggt  42420
tatctgcccc tgaaactcac gtgggttgac actgtagatg cgttccctca atgggcagcc  42480
gccaagtact ttcattcttt aacagacatt gcccttttcg ttaatttgtg aatttatgaa  42540
ttggagaaag taccaatgga tttgaatttc tggggcagga ttctctggga atttaaatgc  42600
ctttaaatgc cgtgagccac tccaggatac agagtttcat gaaaagcccc cttgccagct  42660
ttggagggtt cctgttgtct gagagacagt gggattcttc actcctgcct ctcagaacct  42720
agggtacttg gagagcaggc caaaggcata tggtcccctc cgggggcatc tgtcacagag  42780
ggagtggctg tcctgggatg gggtctgcat cgcggtggac catgtggact tataatgtgc  42840
attccccagt ggtgacaaca ggcacgtccc cagccattgg catttgcact tcatgaaata  42900
aaacaagggc aagtgttttc tgagctccta gtttgttcca ggctctgagt gtagggattt  42960
ccatatggtt ccccttttaa gccatccacc aaccctagga gattattcaa ccccattttc  43020
agatgagggg agccagagtg cagagaggtt cagtagttgc ctaaggacct tagttttagt  43080
aaatgaaact tggatccagg tctgtctgac tctaaaaccc aggctctttc tcctacatca  43140
tgctgctggg ggcccttggg cttcagttat cctgagagtg gacatcagat ggccatcgtg  43200
cagaacctgc ccaaaggctc agtgagtccc cttcctccag tgacctctct ctgggccagt  43260
ggtgccaggg agaccaacag ggtctgcttg attctcttgt gcagtggtta ggtgcagtaa  43320
gttaagcact gtgtttggac ctgggatgga agtccagatc tgcctctcac cactagcctt  43380
tgaacaaaca acttactctt tctgggcttt actttcttca ttcataaaat ggaggtaaga  43440
atatccactt catagggtga taccatgtgt cagtcattac ccagaccaac ttcccaggac  43500
tgtggagtag agaggcctga cctgggaccc tgcgagccag gctcaagtcc tacctttggg  43560
ggaaagctac atcacaggag agacagtgag gttccaggag agacaggaat tggaataccc  43620
```

aactgccagt agctgtgtga ccctaggcag gtccctttttg ctctctgggc cttggtctcc 43680
tgccactcca agggatgttc atcagtgtga cctctgagat ctctcaagtc ctggcattcc 43740
aagagccttg gctctttgag ggtggagggc tgttatcagg cactgctgaa tccttgagaa 43800
cctataatta gagctgtcta tttagggaca cagcaaatgt cttattaatt ataaagaaag 43860
gaagcagaca gattgtttaa tcattgtcct tgctgaaagg ttatgcaatt aactatataa 43920
atattcatta aaagttcaag cagccgcttg ctgcactggg gtctgtagaa cctggaggtc 43980
caccctggag gtggagcgta cagccaaggg ccctttctgt cacctgggct tttgtgagga 44040
gagtttgggg atggttctgg agcatgcagg atttgatgga agggcaaggc tctagtcata 44100
ggaacccagg ctcggtctct cgcctgctgt gcatctttgg gctagttact tggtctctct 44160
gagcctcagt ttcctcatct ataaaatgga gtgcttacgt gcaggactgc tgccctgctg 44220
tagtgcagta agtggcccag gtatgtagta agtaagtggc ccaggtatgt agtaagtaag 44280
tggcccgggt atgtagtaag taagtggccc gggtatgtag taggtaagtg gcccgggtat 44340
gtagtaggta agtaagcggc ccgggtatgt agtaggtaag taagcggccc gggtatgtag 44400
taggtaagta agcggcccgg gtatgtagta ggtaagtaag cggcccgggt atgtagtagg 44460
taagtaagcg gcccgggtat gtagtaggta agtaagcggc ccgggtatgt agtaggtaag 44520
taagcggccc gggtatgtag taggtaagta agcggcccgg gtatgtagta ggtaagtaag 44580
cggcccgggt atgtagtagg taagtaagcg gcccgggtat gtagtaggta agtaagcggc 44640
ccgggtatgt agtaggtaag taagcggccc gggtatgtag taggtaagta agcggcccgg 44700
gtatgtagta ggtaagtaag cggcccgggt atgtagtagg taagtaagcg gcccgggtat 44760
gtagtaggta agtaagcggc ccgggtatgt agtaggtaag gcccgggtat gtagtaagta 44820
agtggcccgg gtatgtagta agtaagtaag tggcccgggt atgtagtaag taagtggccc 44880
gggtatgtag taagtaagtg gcccgggtat gtagtaagta agtaagtggc ccgggtatgt 44940
agtaagtaag tggcccgggt atgtagtaag taagtggccc gggtatgtag taagtaagta 45000
agtggcccgg gtatgtagta agtaagtggc ccgggtatgt agtaagtaag taagtggccc 45060
gggtatgtag taagtaagtg gcccgggtat gtagtaagta agtggcccgg gtatgtagta 45120
agtaagtggc ccgggtatgc cacttatgtg atgacctttg tgaatggcac ccccggaatt 45180
tgcactggca gcccgcaagg cctgcttacc ttacaacaga catttgttgc tcacagttct 45240
ggagggtagg aagtccaaga tcaaggcacc ggcagtttcc gtgtctggtg agggcccgtt 45300
cctcatagac tgcacctcct tgcttcatcc tcacgtggtg gaaggggcaa ggaggctccc 45360
cctgacctct tttgtaagag tactgatctc attaaagaga gctgtactgt tatggcttaa 45420
tcacctccta aaggcctcac ctcttaatgc tatcacattg aggattaagt tccaacatgg 45480
attttcaggg gataccaacg ttcagaccat ggcagaatga aatgaaaaaa tataaaattt 45540
tcagcacaga gcagcctgac acaacttagg tgttcaaaaa ctgggactcc cctccccctc 45600
ccttgagagg ttctgtttcc tgaggcctgg cttagggata agtagttgct ttgaccttcc 45660
atcccattgc tctcttaggg gcttgcaagt gtatggaaca tctgtatcac ttttatcgta 45720
gtgaattgaa aagagatgaa acatcccttg tcttctatgc ttgcagaatg ttaaccaacc 45780
caggggttcc caaatagagg tgcatgggaa tcccctgggt tttggtgggg agttactaaa 45840
atgcagatcc ctaggctctg ccctagaagt ctagattcag tcagtatgag ctgaggctca 45900
ggaacctgca ctttgagtag ctccctcacc ccccaccctt tgatgagagg accccagcaa 45960

```
agcactggtc agcttcagct tcctgtgttc cagtggggcc cagaggggag gtgcttacct  46020
ggggtcctgc agtgttggtg atagaggtac cctggaagga ccccatctcc caactcccag  46080
tttcccttca ccaccctgca ctgcagcccc aaggtggcct tatataaaag gcctttgagg  46140
gttagtactt tccagagctc aacctgacag ttatttgctc atccatccca caagtctgcc  46200
aatcctcgag caagggaaat ttctgtgaaa tgaataccag gaatcctgta ttcccaaggg  46260
attgccctgt actcatgaaa tgcattccta gggataacgt tggggacctc actttcaggg  46320
gcctaagatg ctcttctccc atggcagtag tggtgtccag ggaccttgac tcagatacct  46380
gctcccctcc ccaactcatc tgtgcccttt tctgtatccc ttgtggtctc tcatcccagc  46440
tatagaaatg ggaagaggag aaactggtct gagatcagag agcaaaatgg agggcgaagc  46500
atgagtagcc cactgcctcc ggggagaaat ggattgtgct gagtctccgg catcagacac  46560
agctgacttt cagtcaatcc taacactgct ctttatcagc tctgtgacca gaacttagtg  46620
cctaccacca tgtttgtcac acagcagtgc tcaaatactc agtgaataag caaaattcag  46680
agtcatctgg tatgtgtgga taatcatagt aggtaacatt tagtgagcac tgggctgggt  46740
gttcttctag gtgcttgctt tacagacatt aacttagtca tcataacaat cctatgagag  46800
atagtattat ccccacttta ttggcacaga gataaggatt gttggccaag gtcacatagt  46860
cagtgagtga ttgaagtagg atttgaaccc aggcagccag gctccagagc ccatgttctc  46920
cgcctctatg ctggaggcca gcacataatc ctctcaccct gctggcttat tgtgaaaatt  46980
agatggaagt gtctagcacc atgcctggca catcctagag accacggagg tcgggcctcc  47040
tgcacaccct ggaaggctga agggagccaa ccacggaggt ctgagatgca tctgccttgg  47100
ctgagcctgt cacatgggtc cagcagaaac tcatgataag agctgtcccc agccttgaat  47160
agggttctca ttcttccttc caaattgaga ttcaaccctg gggcttcagg cccctgattg  47220
agtcagcctc tgattgcggc tgcagtaatt atagctatgc agtcccgctg ggccctgcca  47280
tgcagcagct gctctcagca gcaggatcag caccatcact cggggagggg gcttagaggc  47340
gggccgattg gagccgttgg ggccttggtg agccctccaa atttacaggt tccaatcatg  47400
gagtcactga tctggaaggc aaactgaggc ccagctgggg catatctcac ctaagggcac  47460
acagctggga aatggcagag aagagtgcag ggcatggtgg ctccatgttg ccagaactta  47520
aagtggaggt ttggagggat gggaggtgtg gccaggaggg gcaggcagaa gtcaatggat  47580
caaagggact tgagggccag ggaccagggg gccatgaaag atgttatgta gagaagggtc  47640
agatttagga tttgaaaatt cctggcacag acagaggctt cttctcagct gatgaaactg  47700
agacatgggc cagaagagcc ctgatggact cctagggcct tggaccagat ggctggaaca  47760
gggtggtagg actggttggc accatgccct gtgtccccct tggctaagct atgcatggac  47820
gtctgtctcc acagccaagc aggtgtgtcc tgcagagaag ctgagctgtg gacccaccag  47880
ccacaagtgt gtacctgcct cgtggcgctg cgacggggag aaggactgcg agggtggagc  47940
ggatgaggcc ggctgtgcta cctgtgagtc tggggtcaga tctccagggt ctgccaagca  48000
tggtcaggca gcctcaggga gtggcagcca cttctgggga gggggcccag ttccccgtgg  48060
ggcttggtgg tggagaggaa aggataacga tcaggacact agtaatggct agattctatg  48120
gagacatggt cttctttcat cttcacaagc acctcatgag cagccattat catccccatt  48180
ttataggtga ggaaactgag gctcagacaa gggaggaaaa gtacccaagg ctgagtgatg  48240
aaaccaagat tcagattcag gactggacag caaagcccat gagcttttgt taccatgtct  48300
gacatctgct catccatccc acaagtctgc caatcttgga gcaagggcag gggaccagg  48360
```

```
gagggtgctg cgtggagaaa tggcggtggt ctgagccagg gcgccagcaa tgctgggggg  48420
agggggacgg attcctgagg tgtcaaggac gactgttgct gaaatctcag attcaagcac  48480
agacgtcaca gggcagagaa gacattctca gcagcctcgg cagggacaga tggaagtggt  48540
cactgggaca gttccacatc actgagcttc aaacacagga ttatctcctt cccagggagc  48600
aggccagcag ggcctgggcc attggggagc atggccaggc ctcacttttt caattcgagg  48660
ggcacctact gtgtgccagg cctgaagcca ggctctgaaa gggacagtga ggtgaatcct  48720
acacagtctt ccctctggga acacatgatt agtgggggag acagactggc tgtcgctact  48780
aggctgtgcg gctgggctga aatacgggcg gtcaccctgg agggcttgcc aggcacttgc  48840
ccatcactgc tgcctactcc cctctgccag cctctatatt tgcatcctat ccatctttcc  48900
tggcccaggg aaaatgccat ctcctccaga ggtgtctgag tcgtcacact ttaagattct  48960
aagtctggaa tttgatgtgt ctgaagcagg aagcatctgg gtatggaggg agatcctggc  49020
tgggaacagc agtttcaaag tcccagtgat ggcactggct cacttcctca gctgtgataa  49080
ttttgctggg actcactggc caatgagaat cctctttcct ctttaccaag ccccataatc  49140
agatgattcc tccaatatga aggccgctac tgcaagggat gggagtctct ccaactaggg  49200
catgttggaa taggaacatt ccccattaat tatgggagag agaggtgtca gaaggtctta  49260
ctgggcttct atgctatagc ttccaccctc ctaggcagag gaaagagtcc tcccacccct  49320
catctctcag agcttcttcc gtttgtgagt gctaggagta gggtctctcg gcctacgtag  49380
gcctgagaat atggatctta aagttactgt tggctccaaa acctcagaga aaactcagta  49440
tgaagaagca cttccttgcc atccaagtct tcaagtaaaa ttaaaaatta aggcggggcg  49500
cggtggctca tgcctgtaat cccagcactt tgggaggccg aggcaggagg atcacgaggt  49560
caggagattg agaccatcct ggctaacatg gtgaaacccc acctctacta aaaatacaaa  49620
aaaaaaaaaa aaaattagcc gggcgtggtg gctactcagg aggctgaggc aggagaatca  49680
ctggaacgca ggaggtgggg ttgcagtgag ctgagagcac accactgctc tccagcctgg  49740
gcgacagagc gagactccat ctcaaaaaag aaaattaaaa aaaaaaaaaa aaaagcactt  49800
cccatcagaa ctcccagaaa gcagtgagtc caccctccct gcacatgcac aagttgggtg  49860
gggacaggca ggaagggagc tcatctaggt gtcagcgtaa tattgagggg cagtggcagt  49920
ggcagcatgt gctttttcca ccaatgcccc agtgtctcaa aagcccagga ggggaaaaaa  49980
attcaactgt cagacacttg gtagagctgt cagaaacgca tgacacgagc tacctacctg  50040
gtgaaactga agacatcact ctattttatc ttcaataaca atgaaaattc acatttttcc  50100
atcagaaagt gaaaacacag actctgggcg cccccacgtg gaaagatctg gtgctgccac  50160
caccacctca cctttggcca cagccactgc atcagtgccc caccggggcc tacccccatc  50220
ccggggccag gtcttggcct gtgtgtggac gcacaggagg gagggaagtg aggaggtcac  50280
tgccctgaaa aacagctgga aaaactccag gaagggagga gaaaaccaga aaagccaaga  50340
ggaggagtca gagtaggaaa gaaaagcccc aaatgtgagt tctggttctc ttgttgtcat  50400
ggactgtgtg accctgggca agctgctcct ctctctgggc ctcagtttcc ccatctataa  50460
actggcaata gggctggctg gcctctaagt tcctcccggc cactgaactc agactagcct  50520
accagagaga agcccagagc cccaagcaga gccatgacgt gtgtccttaa ttactgcaca  50580
tcccataatt atacctcata cctgggccag accagttcca tccactccac acccactcac  50640
tacagggagc tctgtaccag gccctcagga caaaggaggg acacccccag gcagtgtgga  50700
```

```
ttcttggggc agattgaaaa ggacatgaaa ctcagacgcc tgcgcgactg aggggctcag  50760
aaacgagggc agaggcagag atttcccaag cggggaaacg ccagggtgtc atggaagagg  50820
tggaatttgg gcccttggaa gatgagagct catcattgca aaatgtagtg gtgggcaaga  50880
agtaggttcc cagcagatgg agcaacttga gtaaaggctt ggaggtggga gcctgtgcac  50940
tgggcccagc aaatggtcta gcatggcggg agctgcgaac attcaggagt gaggtgatgg  51000
agccacagga ctgacccaag agacgccttg gataccaggc caggggactc aggtggaaca  51060
gtgcaggtta tgctatgcat cgctatgcta tgaggagcca accccagacc ctggtccctg  51120
ggaagggtca gtgtcattta acagatcatg tcctgggacc atagcagggt ccttcaagac  51180
aggcagtgct ctaaggtttc ggaatccccc tcctagtccc accatgctca tgctcattta  51240
cccagtgagg cctggggggc tcacaaaggg caggtgtgtt gccagtcacc tagcatgtcc  51300
gtgttggaag cccgccttcg ctatgcctaa ctgcacgtcc accattcagc cccaaaggg  51360
cacttgttct ggcccccggg tgagggtcgg agcccctgta gccggaccag cggggcccca  51420
ggtcggccgg ggaggggggtc ggcgggccga ccggctctct gtcccgcgca gtgtgcgccc  51480
cgcacgagtt ccagtgcggc aaccgctcgt gcctggccgc cgtgttcgtg tgcgacggcg  51540
acgacgactg tggtgacggc agcgatgagc gcggctgtgc agacccggcc tgcgggcccc  51600
gcgagttccg ctgcggcggc gatggcggcg gcgcctgcat cccggagcgc tgggtctgcg  51660
accgccagtt tgactgcgag gaccgctcgg acgaggcagc cgagctctgc ggccgtccgg  51720
gccccggggc cacgtccgcg cccgccgcct gcgccaccgc ctcccagttc gcctgccgca  51780
gcggcgagtg cgtgcacctg ggctggcgct gcgacggcga ccgcgactgc aaagacaaat  51840
cggacgaggc cgactgccgt aagccccctc cataccgccc agccccgccc agggattgcg  51900
gatccgctat ccgatccgga tccgccaggt gcaggcttcc tttcattgcc ttacctgaat  51960
acattacccg ggtttactac agaggagacc gaggctggga gaagtgaggt gacttatttg  52020
aattcacgca gctgccgggc tgcggagctc aggtctaact ccagaagcct ccactggtat  52080
ctgtgtccct gctgtgagcc ctcccagtcg tacttcccac ccccatcccc cgaacccctc  52140
cacccagaaa cctggcaggc tcaggagctc cccccatctc tttacccgct aggcctgctc  52200
attcctcaag gcctggccta gactcctctg accttcccag ctgggctggg tccctctgct  52260
gggcaggtcc ccagcagctt tctcttatag ctcatctcac actgatgtcc ccatctgagc  52320
attcctcacc cttgctctgc accctgagct cctagaggat gaggaggctc ttaggagtct  52380
ctgggctccc acccccacct ccacctctcc cagcacagca cctggcacag gaaggtttgc  52440
caaatggatg aagtcattaa gtaatgagca ccaagactca aaagaaggcc gtgtgtctgt  52500
tctgaggagt ggccctggag agaggcaggg acagggaaac aggagatctg ggtttagtcc  52560
tgaatctgcc agccagagtg ctgtgtgacc ctgggcaagg ccttcccccct ctctgagctt  52620
cagtctcccc atctgtacac tgaggtgcct tggccaggtg tcctttgagg actcctgagt  52680
tcagccactg gttctgtttt tgctgggggt ggctatggca tggggattgg ggtggtgggg  52740
aaattgtcct agcaccacac tgactctgat cctctcccct tgccctctcc tggcagcact  52800
gggcacctgc cgtggggacg agttccagtg tggggatggg acatgtgtcc ttgcaatcaa  52860
gcactgcaac caggagcagg actgtccaga tgggagtgat gaagctggct gcctacaggg  52920
tgcgtgtggt cagggcacag aacacatcct ctgtgaggat gccctaggct ctggtaactc  52980
tccagagggc agagttggga ggagtttccc cttggtcccc aagatgcatt ttcccccaga  53040
gcatcacttg cccctaaatc acctggctcc ctttccatgg ggtcctagta gcaccagaac  53100
```

tggatttgta aggactttgc caaagctgaa agacacctag ggggacatga cagagcactt 53160
gggaagtcca gcccccacca cttgtccagg tcccagctgg tgagtggctt ccctcactag 53220
ttcccaggct gagcagaggc tgagtcttgc tccccaggga gcccctttag ttctcagatg 53280
gttcttctgg tcaccacctg ccctctgcag gagcagggac cctcattcac tagtcatctt 53340
ggggaatgga taacaggctg ggcagtgtag caacttcccc tatccggggt ccatggggca 53400
aagtcccccc aggagatgat cagtccagcc tctaaggtct ctctagagct gctgcctggt 53460
cctcctagga cctgagtcct gcaagatgag acgcagatcc ccacagccct gcccagctac 53520
atgaggctta gcctcctaat catccctggg atcctgtcct gtgagcagag cttcctcagt 53580
tcctggattt acctgtctgt cctgggccac cctccaggga cctgtgaggg actggaactg 53640
gagctctgct tgcctcctgt gggccccagc ccagcccttc ttgtccaagg tctcacaggc 53700
actgtccact ctcttgtccg gcccaacaga gtcaccctgt gagggtcccc gcagatttca 53760
gtgtaagagt ggcaagcgcg tggacggcgg gaaagtgtgt gatgtgcaga gggactgccg 53820
ggactggtcg gatgagcttc tgaaagtgtg gtgcggtgcc tgtctacgcc cactggctgg 53880
actcagtctc ctaccatccc cctcctggta tctaggctca aggccctcca gtgcccccctg 53940
ccctgacact ttctgctctg accctctctt tggattcatg tgccgtccta tggcttcaca 54000
tggggctttt cgcccccagg cctctggtct acatctctac aaagtgctaa gagcttgtcc 54060
atcccaggta ctaaaaaatt atgtttctc tcacaaactt ggcctttcct cattccttcc 54120
ccgttcagac ctctgagacc ttctggaact ttctctcttc ctcggtgttc ctcccctgct 54180
gacccagcca aggccctggg ctctgaggtc ttctagcccc ttgcagaaga cccagcagag 54240
ggagaagtgg gcacagcagg caggcagcca ggtgaagcac atcccagggc cactgctcag 54300
gccatacctg tgtgggagta aggcaggcct tgcagcagga ggtggcacca tcctaagccc 54360
tgaggagttc ggacctgatg gggagaccag acttggaggc cagactaaag cgagacctgg 54420
atggaagtgg ctgccctgat gtcggctaca gctgtcaggg tgggttccag gctagaaaga 54480
acagaggctc caggctgtag gtagggtggg catcccagag aacatgctag aaacccagtg 54540
tggactccag gaaggttcat gagtttttt ttgtttttg tttttactgt tcccaggtta 54600
gggcttgagg gagatttgac agagaagccc tgggaggaca gaggctaggt cagtccctcc 54660
ctttcctgcc ttctggcaga ctgtttcccc agcacctacc tcctgggtgc ttagaggagg 54720
ttcatcctcc tgagcttccc aggaagagca tatttccttc cccttttgaa gattaaaaaa 54780
ctgattgtga aaggaagagt agttgagtga aagtgactca gcttctacct gagctggcag 54840
gagatagaca ctccctctgc ctccaggccc tgccaagaga agtcccagaa gaaggaactt 54900
gtggaaaaag agacagggaa gccagaacta ctgagcctag ctcccccaac acccagattt 54960
ggagtagcca gggactactg tcctactaat ccctctcttc tctctcgtcg tttgcatgac 55020
acaccaaaga ggagtacgta cacacgtgct tgtgtctgtg tgtggcctct gtctctgtgt 55080
tggtgagagg ccggtgtctg tatccatgtc ttcttctctg agtaaagcag gggaactgca 55140
ttcatgcatc tatgtgtgtg accccatgta tgtgtgaatg tatctatgga gtccatggga 55200
ctgtttgtgc tctgcacata agctggtatg tgtgcatgta gttgtgggca tgctggtgtg 55260
tgcatgtagg tgtgtgcagt gacaccactt cttccttcca tggaaggaag ccgcaaatac 55320
tactctggcc tctctgcacc actctacccc atccccctcc tctcctggct ccccagcgga 55380
atcacaccca ggctaggtag aattaagaag gactgaagac ttccctgcag gcatttgggg 55440

```
aaaggttaca gggacagaca ggtgcagacc tgctctcctt tctcttcccc tcacccacct  55500
gagccctgga ggactctgtg ccttccttca tcagaagcca gtcactttga gttctctcct  55560
ttccccttcc ccctttcagg gccatcccac ctacacatgc cacttcatca agtgctcagt  55620
aaatagaatt gttgagttgt tgctagctgc aaaaggagag gaaggaggcg agtggatgca  55680
tgatgggggc agtgggtgag tgggaggaca gatgaatgaa cggtgctcag ggaataacac  55740
aggaaaggag aggtcaggga gggctccgag cgactgaaag attcctagag gtgggagctg  55800
ccgtggctca gcccacctcc aagggtctga ggcttcccag ggctgggcct ggctgagtca  55860
tccctgggtc ccccagtcat ggagttgctg tggtcttgtt ctttcagttc cgccaacatt  55920
cctgggaaac aggaggaggc ccaggggtaa aggggttatt ccctaagcat ggctcaggct  55980
ggaagtgggg gcaccccata gctgtgcatg gcctggggtg ggcagctcag accagctata  56040
tgcatggcca tggctggctc agctcagcac tgcttggctt ggctggagtg gcagtgcatg  56100
agcctggggg gcagaggggg agaggggcgc ggcacctctc cttggcttgt ggaattaacc  56160
ttctgtgact ctaaagctca ggagaggctg taagagcatt ggtcctggat tccctgacct  56220
cccctaagac cctgccagaa ggtagtgagg gagtggagga tggggaacca gaaccagatg  56280
acctctgggc atcccttcac ctcttgcagc aggtggtaat cctggaaccg ggcccatgac  56340
aagataggag gaacagggac aggtgctgag aggagaggag ttaaaaaacc catcatatta  56400
gttcatgata ggagagaatt gatttagcaa tggctccatg ttaaaaaagg cccaggagtc  56460
ttaaataacc acaagcacat tagggggggc atcctgtgtt gttcaggttc cttctgggtg  56520
gcaaactagc tctgggccct gtccagacag ggacatggac agatggagtg agtccagaga  56580
aaggcaccca aatggcagga gaccagatat cagtgcttta agggagcctg tgcaccctgg  56640
ccaaccccac acagcagagc tgggagcaca agcagaagcc tcagcaggca gtgctggtcc  56700
acagtggagc cagctgcccc aggagggaag tgggctccct gaggctggag atatttaagc  56760
aggggcattt tggaagggat tcttagggta tcctgagggt tggatgtgac acacacagga  56820
cccttcaact ctgaggtcac gaggaaggag gcgctgtgag aaacatgttt gtgaaaggaa  56880
agaccttggg ccactgggga aggcctagct gcctccagct tggtggtgga cagagcccca  56940
gccgggaggc cggggaccta agttctggtt ccactctacc ctgtctctgt gtctggcctg  57000
gagtaggaac ctgccctctc tgtgccgcct gctgcccaga acacctggta gatgaggctg  57060
aggctcagtg aggttgtgga gccctcctgc ctctatggga gtcccactgc cctgaggctc  57120
tgcttctgct ctaggtccta cccctgccct gccccccactc ctcctgggct cctggacctt  57180
caggagccca tgtccctccc cagggctgaa cgagtgtctg cacaacaatg gcggctgctc  57240
acacatctgc actgacctca agattggctt tgaatgcacg tgcccagcag gcttccagct  57300
cctggaccag aagacctgtg gcggtgagac cttctcccac acccccaagc agaagcagat  57360
cctcctgctg gttctgactc ctgctcctcc ccacagacat tgatgagtgc aaggacccag  57420
atgcctgcag ccagatctgt gtcaattaca agggctattt taagtgtgag tgctaccctg  57480
gctacgagat ggacctactg accaagaact gcaaggctgc tggtatgaac accccaaggg  57540
cagaggggca gctctgaaag gcatacagga agcagcgtgc ttccacttgt gaggagtggg  57600
cgtgtacatg tgcgcacaca caagaaggca ggttgtgtta ctgagaggta cgggaatcct  57660
cggtcccttg tctagcttgg gagaaagaat tcagccaaga gacaattagt aacataagcc  57720
gaaggtttat taaggagata agagtacaat ctaagacagg agcaggctga cccagctggg  57780
agcagcagca atagctgtgt ttctttaaag ggacagtgca ctctgaaagg tgacgcagag  57840
```

```
tgggggcagc ctgctaaaag agaatgaacc agcggcagcc ctaagagttc tgcattgggt  57900
tttttcttg aagttcctgt ctctgtccta aatctctgcc attttctttg tctagttttc  57960
ccattcctgc tttaagtccc tgcctgttcc tcacctagtt cccacccagg cttgtgggac  58020
ctccccttac tattagcttg tgtgcatgcc cagctctggg cacaaatact acctaatggt  58080
gccatcactc gttaccacca ccctaggaag gttgtatagc agtcaaatct gattgggcct  58140
gcatatttct tagggatttc ccctttgccc ttcccctcct cctcaacatg cagctagcta  58200
cattctgatg ggagaactgc agagtgagca gtttctgggc atcttaaggg gcattccttt  58260
ctgcagaggc atttcccctc ctctctgctc atatctagca tgaatgtttt gggtggtctc  58320
taggtgtgag attttctaga cttccctttt ctcagggact ccccttctg ctcatgtcca  58380
gctgtctgcc tactctagca gttgcacaca cagtgctcaa aagtgtacat acacatcaca  58440
cacacaacgc actgcacact aacacccaca cagacactgt atagagccac ccaatatagc  58500
ccacagagat gacactcata caacagaata tgaaccacac agagactaca cacacagcat  58560
atggagtcca cacaaagagc acgacctggg cagacctaca cattgatcaa ttcagccagc  58620
agaattaatt cattgtattc agttgtttat attgaacacc taacattgta gtagacactg  58680
gggattcagc agtaagcaaa acagatgcaa atccctgtct gccctcaagg gactcatatt  58740
ctaatgggtg agccaggcta gaaatcagat aaatacataa aatatagtgc atggcagatg  58800
gcgataaggg ctaaggaaaa atagaaagta gagaatggga atagggaagt ccaggtgagc  58860
agggggttct agttttaaat ggaatggtca gggaagccct cactgagaag gtatttgagt  58920
aaagaaggtg aagggggggtg ggtgtggtgg ctcacgcttg taatcccaac actttgggag  58980
gcctaggcag gaagatcact tgaggccagg agttcaagac tagtctgggc aatgtagtaa  59040
gaccctatat ctaaaaaaaa atttaaaaac tagccaggta tagtaccatg cacctatagt  59100
cccaagctac tcaggagact gaggcaggaa gatcccttga gcctgggagt ttgaggtcac  59160
agtgagttat gatgccactg cactccagcc tgggtgacag agtgagacct tttctaaaaa  59220
aaaaaataat aataataata aataaaaagg gagtgaggga ggtgagacag taagctacca  59280
tgcaattatc tataggaaca agcatttcag gctgaagaga cagaaaccgc aaaagcccta  59340
atgcaggagc atgcctagta tgttcaagga atagcaagga agctggtaca gttggagcaa  59400
ggaaactagg aagagatgaa gccagagagg tggcttgggg cagcccaaag ggccttctag  59460
accattgtaa gagccagctc tggatttcac tctaactggg gggaaaccat tgagggctct  59520
gagtagggaa gggacatggt gtgacatttt attctgactg cagtattgag aacagactgt  59580
agaggacaag ggagaaggca gggaaaccac ttaagaggtc attgcaataa tccagaagcg  59640
aggtgatggt ggctgaaccc ttattcccac attattactg tgggaataat gaaaagtgga  59700
cagactgcag atatagtgca aaggccagcc aacaggattt gcttatgaat tgaatgtgga  59760
atgtggaaaa aaaagttaca gcaactgaaa aaataagatt gctacgtatg ggcttgggaa  59820
agatggtgag ggaagcaggt ttggaggaat cttaggctgt tttggacatg ttatgtttaa  59880
gaaaactggt taggtatcca agtagagata ttgagaaggc agctggatat atgagtctgg  59940
agttcatatg caagttaaat acaatataca acagataaat tataacaata cagcagccat  60000
aatactgaca tgtagcccat aaacccaaaa actgtaacac ccaaactgta caatatgtaa  60060
ctcatacatt agtatatcac atataacgtg taacctgttc ttgcccccat atagaacaca  60120
tgtaatacat gacacagatt atgtacatgc actggagaca acatgcaact acccatgcat  60180
```

```
atacaaaatc cacacacatg aatatttcaa gtgcagttac ataaaatctc aaatcataaa  60240
cacagggggt tcctgtcaca gtcacagctg tcatttaaga tcactccaac atgccccttt  60300
aacctggctc ctgccttcag ggaggtgaag tgtcattact gtcattttgg ggtgagggaa  60360
atcacagctt gtcagtggca gagctggcct gtaactcagc tttcatcctt gccccttcct  60420
gcaccttgag cccattctcc atgctatttg taccacactt ctgtctcact cccaccctgc  60480
tttgaattag tctccatcac tacacacagg tcacacaccc agccccaggc cctacctgac  60540
tctgtgctgg tcccatcctc cagggagcac attagcttgg caaagatgca cagtgacagg  60600
gactggtggc tggcagaagt gtcagctgga aaacaagaga aggaggcaca gggagcttga  60660
ggggcaggtg ttactaggag cagcccctca gacagtgttg gtgcctgaga gtggcccaat  60720
acatctagaa acagcctgtg ggagctggtg ctaggccctc agaggcccat gggacagtgt  60780
cctcccatat ggagtagcca ggaaagtcta ggtcacttat ttatcatctt aaaatctaac  60840
cctaaatcta agaaaaatac aggttttgtg tatacatgag cagtttatgt tgtctctact  60900
gcatatatat aatctgtgtt gtatatcata tatgtcccat ctctgccatt ggctcaggat  60960
agagaacaaa ctcacccagc tcataggacc ttttgtgatc tggcccctgc caatctctga  61020
agctcatctc ttgctatgtc cccaatactt tctatcctga atcatctttt tttttttcct  61080
ttgagacaga gtctctgtca ctcaggctgg agtgcagtgg cacaatcatg gctcactgca  61140
gccttaacct cccgggctca aatgattctc ccacttcagc ctcctgagta gctgggacta  61200
caggcatgtg ccaccatgcc cagctaattt tttttttatt tttattttta gagatgggat  61260
tttgccatat tacccaggct agtctcaaac tcctggcctc aagcgatgtg ccagcctcag  61320
cctcctaaag tgctgggatt acaggtgtga gccactgtgc ctggccccta gttatctttc  61380
taagacactt acttgctcag gtagttcctt cttgaaccac agcagtaggg cccaagcaga  61440
gaagatgata gttgctggaa agaaatacat agtaggtgga agggacaacc tgagcaaagg  61500
ctctgaggca ggaagcccat ccatggctag gtaatggtat ctggtaggtg gaatcaagct  61560
atgttggaga ggcgagtaat gaggctggac agggaacttg ggtcacact gtggaaggct  61620
ttcagtgcag gcctaaggag aaaatgggga gccataaaag attttggaga agtttgtatc  61680
taataaaaag aataagaatc ttcctgctat gcgtggtgct ctgcatcttc tgctttctgt  61740
actcattatt tcatctgctc ctgcaacctg taaagtagga attgtcacta ctattttaag  61800
gaaaatggat gtgtcagcca gcaagccagt ggcagagtct tggtctccag gctccctgcc  61860
tcttgcactg actctttctc tttcaacctc cctgcatgac agctggcaag agcccatccc  61920
taatcttcac caaccggcac gaggtgcgga ggatcgacct ggtgaagcgg aactattcac  61980
gcctcatccc catgctcaag aatgtcgtgg cactagatgt ggaagttgcc accaatcgca  62040
tctactggtg tgacctctcc taccgtaaga tctataggtg agcggccata tcctctgcag  62100
caaggcatga agagtggggg tgaggggtgg tgacaggtga ggaggggagg agtggtgtct  62160
gcctctagag ctcctcagga cagagttggg acttgggaag agatgcagga tcacagtgga  62220
tatggaactt ctgggacttt actggggctg gagtagtctg agggctccct tgggttagca  62280
gctttgagcc ccaaacacct gggatttgtc tgacctctgg aggcctaata tggaagcaca  62340
agacacagga actgtttggc cagggcagaa aggaagaaat cctggctttg gggaggactt  62400
tccaagcagc tcacatccct gtgtgttgga acctggggac ttagacctgg tccctgccca  62460
gaggatccca ctcacaacac agtgacatcc atttgtgatg atcatgagaa agtacagagg  62520
aggcctccga acccacctgg gcatctgatc tggcatgcct tcctggatgg catcacccca  62580
```

```
aggccagctt ttcactgtct ttgacgccac agtcagtgga cctggtgctt gggaagctct  62640
tcacacactg gaggaggttc tctcctagga ctttctcaga tgccagcacc tgccccactg  62700
catgtctggg ccctcttcag gcagtcatgt cctttctttg tcctgagatc cacttggcag  62760
gaatgccgat gaccaggcgc tgggtagaca ctgagtcact gatgaaagaa tgatgggaca  62820
gatgggtgga agagtggatg gaagcaaata tagcaagtgc tactcactga caactagatt  62880
cctgcctccc tgcaacatac agacactccg ttcacacaca cccaaaaaca taactagaac  62940
aatgcctgtc caagagatgt aactgaaaga ggcaggattt ggtgacagac tagatatggg  63000
gctgatggaa gaaatttact ccttcatagt gaattttggg agtttcaggt ttttggcttg  63060
ggaggtttca tgaatggtgg tgctgttctc tgatgtgtga agcagtagag gaggatcagg  63120
gctcagggtt tgggccgtct ggttggccga ggggaaggga atggggatga acagttttgg  63180
acatattgag ttcaaggtgt ccatgggaca tccaagggga gctagttagc tttgcagtct  63240
ggatcgtaag agagctgttg ggattggaga cttagttatt gatggcagtg gacactaagg  63300
aactaatcac ccagagagag ggcaagaaga agaaaacctc tggggaaaca gcatttgcta  63360
ttttgctaat gttgcctcct gagtgtctac tgtattctta gcccttcttt ccattctcac  63420
tggcacggtc attcttcaga ctctcttaat ctcccaccca gatgctgtaa cgtcctccta  63480
accagtttcc ctgcttcatt ccctctcctt ccaacccatc cactccatag atgccacagt  63540
gaactaacat gcttattgga ctatatcctc tggcctgtct agttatcact ggggagaaat  63600
cctaattcct tggcgtggta ctcaaagccc atcaagatgg ggttcctgcc tacacctgct  63660
tgcagtctga cacccacata agcagctccc ctaagtatct cactgttcca gagcagactc  63720
acctctggcc atttgcacaa gcctttcttg ttccctaatg gctttctgtc ctggtgactt  63780
catgctcctg gtgaactcgt ccttcaggac tcaactataa agccttctcc cgccctctcg  63840
gatgaggcag tctccatgcc tctgctgcca tagcctctaa tgctttccat aatcacattg  63900
tattatatct ggctcaccct aatgggcaga gctgtggagc agccccacct tagaaagcca  63960
gagaccgtgg cccatgtaag tctgtacccc taccctggta ccccagggaa tgtgtagagt  64020
ggaaattatc cacgttcctc taaaaatcta ttgccatggc ccagatggaa gagaggggaa  64080
gggtgcacag gtagctccag atgggcccat gggtggaaca tctgccccat ggtcatctct  64140
gttttctctt aagcgcctac atggacaagg ccagtgaccc gaaagagcag gaggtcctca  64200
ttgacgagca gttgcactct ccagagggcc tggcagtgga ctgggtccac aagcacatct  64260
actggactga ctcgggcaat aagaccatct cagtggccac agttgatggt ggccgccgac  64320
gcactctctt cagccgtaac ctcagtgaac cccgggccat cgctgttgac cccctgcgag  64380
ggtgagtgtc ccaactgaac ttcccattct cccaccatag gtgctcagtc ctcttgtgtc  64440
tgtcacaagg gctatcttga gggttctaga aagctctggg ccactcagac acaggccatg  64500
gggaagaaag tcttgttaat ccccaaccaa ggttctctgg gcattggtca ccaaagttct  64560
ccctggactc tcccacccac tcgttatatc gtagaattgg agtgtctcag agcagagtag  64620
ggctctagag atggcctgat agaagctcct gggggaggaa gcctttcttc aggctgctgt  64680
aggtgagcat ctgacagctg ctcacatact tccaaagaca ggtagctcat tacctcccat  64740
agggcctgtt tcaccgtggg gcagctctgc tcattagaaa gtgggtcttt tcccctcata  64800
atgccaaatc tatctccctg caacttcctc cattggcctc tggagttaca taaaacatgt  64860
ctattccctg ccctgtgaga gagccagcaa gatttgagga ccaagatcac tggtctgttc  64920
```

```
tgcttcagac tgcctgcctc catccctacc cctgttgcct atggtctctg ggccctcacc  64980
acctaggttg ccctgctctg gccacccctc agttttggga gttagggatt ctgaacagaa  65040
caggactccc tctctccctc agtgtggata tcttgagatg gttttttttag cgttatatca  65100
tgttaagttt aacagaatca acagctgctt cctactgcta tttccttgtt aaacagggat  65160
aagaaaaccc tcttcttcga gcaagggcag ctggtgaggg gagtaccaca tgggaggtta  65220
tgtgaggcct tgggaagtga ctgatagctg ccattcacta agcatgggtc aggtgcttcc  65280
agcacagaac taggcactct gacagatacg gagcctctcc tcttaccctc acttcatccc  65340
tgttctctgt ctgttctcat gcagaccttg tgttgcacct gccacatcct gtccctcaca  65400
tcatagagtt acacccagcc caaccccaat ccactgcgga tcgtcagggt cccaggagga  65460
aacccactgc atactcaaga taatcagagg agggtttaat aaagggacta tttacaaagg  65520
agtgggttag gtctaattta ctaccttgga ttagtaacag tgggctgcta ctggccctag  65580
taggcctgag gagacaaaag cagggagggt tacctgagtt aggaagctca tccactttct  65640
cctctgaaac cagaaaagag agggcttact agggccttcc ccacactgac accctagggc  65700
tctagttagt tagcactgcc agaagtggga gagatggggt cacaggctat tcagctgagt  65760
ctgggtgcaa tctcggagaa tagttttcct caagttctca aatgaggtga aggctaaagt  65820
gcctgctaaa tctaagattt gatggttcaa aagaacttta gaggtcttct cagtccctac  65880
taaacataaa ccacaactag tcaatgggtt attgagctct tgtgactcag accaccccgg  65940
tcatgtcccc agcaagaagg caaattgggt tattttgtct tttaggttca tgtattggtc  66000
tgactggggg gaccaggcca agattgagaa atctgggctc aacggtgtgg accggcaaac  66060
actggtgtca gacaatattg aatggcccaa cggaatcacc ctgggtgagc cctgcctttc  66120
ctgggttggg ggcctattct agtgccttgt cctgatcact gtctggaact ccatgagtct  66180
tgtttctggg tcctctcatg gtgccagtga ctttgtttcc taatggttgc cgtaggctgg  66240
cctcagtgtg aggcctagaa atgtgggcag ggagaggtac aaaggaacag agctccagac  66300
tggggtccca ggttcatgac ctgatcctgc ttccttccca agatctgctg agccagcgct  66360
tgtactgggt agactccaag ctacaccaac tgtccagcat tgacttcagt ggaggcaaca  66420
gaaagacgct gatctcctcc actgacttcc tgagccaccc ttttgggata gctgtgtttg  66480
aggtgagtcc tgtaaggaga ggcaagggcc cactaggaag ctgaagccta gaaaatgctt  66540
gttcaaatag gatgagtccc tgagacttgt tcaaatgaaa acaggaacag ggaaaccaac  66600
tgatttgttt gtaaacaatc tgtgagctgc ctgcacacaa aggctctgca gcccactctc  66660
cacctggcag cctttcccac gctctcttcc caagacccct ctcccagagc acttctcaca  66720
ggtgagctgc taggcatgta tgtttcctct ctgtgccctc agcacccagc actgtaaccc  66780
atatacaaaa ggcacccagt aaagggagga aaggaagaag gaacatacat atccttagaa  66840
tcatttactg gaggaaatgg cctgagagat gctgttcaat tctgcacact tttattgacc  66900
tctgccagac cctggggtca tagaagtgaa tcagacacta tcctagtctc aagaagctcc  66960
cagcaaagtg aggagcgaag accctcctgt gccctgaccc taatgacttt tcttctccgg  67020
gaatgaagaa gccagaacca accaaggtct cacaccttca cctcttcccg aaaactaact  67080
ccaccaccaa ggggagggaa agcaaaggga tgatggtctg tggtgggcat tggcaggatt  67140
tgcttgcagc aaagttactc agcactgctc tgaagttgtg ggcaaagctc cacctctaag  67200
tccagcccct gctttaaagg acaggtgtgt tggtacacaa gtgtttgtgc ttgtttatat  67260
acatggcatg tacatgtaaa gtatgtgtat gtgcatgggt aaatataaat gcatcagaat  67320
```

```
aaaagtgtgc attcctctaa gtgctggtgc ttatgtgtgt acatacatat accaagatgt  67380
atatagactg catatttagg ggcaaatgta gctttttgtg tgtggatgaa catttgggta  67440
tgtgtttaga tctgtgtatg aggatgcaca gttgtacctg tacgtgtgga tttgctgaca  67500
gatgcacatc taggcttata tggactaacc atgtggactc gtgtggatac ccagaggcta  67560
caggaagccc agcaaggcat aaccctcata gctcacacat tccttccaat cttggtccca  67620
ggccccagta atgataatgc tatagagatt taaccttggg tttctgctgg gctctagcaa  67680
gcaggcttag ttcagcatga atgagtaatg ttgtggctgt cagttcaaag cacagaatca  67740
ctgaataatc ctctaagata gaagggaaca aggagacgtg catcacagat tagaggctga  67800
gagccccacc gtgaatccat agacaggaca gatcagggga gatttcaggg aagttcttgt  67860
gactatggtt tggggccaac ccctcagact gaggtcatgg atttacactc caggcctccc  67920
atcctctgca tctatacccc acaggacaag gtgttctgga cagacctgga gaacgaggcc  67980
attttcagtg caaatcggct caatggcctg gaaatctcca tcctggctga gaacctcaac  68040
aacccacatg acattgtcat cttccatgag ctgaagcagc caagaggtga gctgtctctg  68100
gtcctaggtc ccaggtcccc tgactgtgtc actgtgtcct ctcctttcac caggcaggct  68160
gtgttcacat tcaggtcaca actcagcaac cccaggaata ataacaacaa tccctcttgt  68220
tggtagagta ctttttcatc atatattttg tctcatttta cctcaagttc tttgtgaaat  68280
aaggctgggt ataaatgaat acataactgt cctgtttttg ccaatcctac aaagtgtggg  68340
tattactctt ctaacagttg aggaaacgga agctcagaga ggtaaaataa tgttagcagg  68400
tggcagaact gaaacctaaa cccaggtcta tctggttcca cagctgcttt caccatgaca  68460
cactgcatct aacttgctat ttgtagccat tctgcagtag tataagctaa tgtatccgag  68520
ggccatataa taagtcagct tattggttgg gaatagaatc taggaatcct actactaggt  68580
tgtcccctcc tctatcacta ggatacatta attctaactg taactgaagt gttggctgcc  68640
agggtgaaag agggagagca agggagtgta aggagctaag attggtgcct gattctagac  68700
ctagaaattt aaatgagaga catagtatgt ggcacaggga aaaataaaaa ccgcgggctt  68760
atgggctttg gagcccagcc gacctcaatt taagttctat ctctagtcca gacatggtgg  68820
ctcatgcctg taatcccaac actgagaggc tgaggcagga ggatcccttg agcacaggag  68880
ctccaggcag cagtgggcta tgattgcatt actgcactcc agcctgggcg acagagcaag  68940
acccctacct cttaaaaaaa aaaaaaattc ctagagtata ggtttgacga atttgttctc  69000
tttgagccta ggtgtcttta tttgtcagtc tgggatgtaa cgtccccacc tctcagaatt  69060
gttgcaagga ttaaatgaga gtgtagggat aaaacactag gtatggtgct ggaaagtacc  69120
caataaaagt agtagggagg ccaggcatgg tggcttatac ctgcaattcc agcactttgg  69180
gaggccaacg caggaggatc acttgagccc aggagtttgg gaccagcctg ggcaagaagg  69240
caagactcta tcactacaaa aactataaaa atgacccttg tatggtggca tgcgcctata  69300
gttccagcta ctcgggaggc cgaggtggga ggatttctta agcccaggag tttgaggctg  69360
cagtgagcta tgattgcact gctgcactta gtctaggcaa cagagtgaga ccctgtctca  69420
aaacataaaa cataaaaaaa attgaaaaag tagaagggct tcacaattgc agagatgtgg  69480
aaccaaccta agtgtccatc aactaatgag tgaataaaga aagtgtggca tatatacacc  69540
ttggaatact actcagccat aaaaaggaac aaaataatgt attttgcagc aacttggatg  69600
gagctggaag ccattattct aagtaaagta tgatagtagt ggaaaaccaa aaactatatg  69660
```

```
ctctcactta taagcaggag ctaagctatg agtacacagg ggcatacaga gtatagctaa  69720

gctatgagta cacaggggca tataatggac tttagagact aaaaatggag aaggtaatag  69780

cggggctaga gatttaaaaa aaaaaaaatt acacattagg tacaatgtac actacacttg  69840

ggttacaggt gcgctaaagt accagaattc accactatat aattcatcca tgtaacaaaa  69900

aacgtgtatc ccaaaagctt tgggggataa aaaaagaaag aaaaagaaaa aaaatgtgaa  69960

aaaaaaagta tagggcaagc tttttgagca agccaggtgg gagaagcctc atcctcagga  70020

ggcaggaaga cctggcatgt cctgtctgtg ccccagctgt ctccctctct gccattagct  70080

ccagatgcct gtgagctgag tgtccagcct aatggaggct gtgaatacct gtgccttcct  70140

gctcctcaga tctccagcca ctctcccaag tacacatgtg cctgtcctga cacaatgtgg  70200

ctgggtccag acatgaagag gtgctaccga ggtaagcaga ccttccagga gggatggccc  70260

ctggcagtgt cagaccctac cctgctgaaa tcttcccttg gcttctggga cacagtatgc  70320

tgctggtttt cttccatctt ccctggttac ttgttgcctt ttgggggttt ctcttttttta  70380

ccttccttga atgctcatgc ccccaggatc cttccaaagc tttttctcac tcccaaggaa  70440

aaaatgcaca tatacataaa acattttaaa ttcagtttca gggagtttct ggaacgcttt  70500

aaaaacctca agttaagaac ccttaatcgc cgtggcttca ggtacatgca gataactata  70560

tatttgcctg tttctcacct agaacttaac aaacactaca cagcagccct tttgcaatat  70620

aattgggact aatagttaat acttcaaccg catacacaga ttcatgtcct aatcttgatg  70680

tatagccaag gcctttcatt tgagcctaag tctactgcat tattaatgat ttacaggttc  70740

aattgtttaa agtggaataa gaatttcaat ctattggtat aacaatatat gagtgtaaaa  70800

tccttctaga tttatctgat ttcccctccc tacagtcttt ttattgctga tcttacaact  70860

aattccacag caatgtttta atgactcatc tttattgaat caaagtgaag tgcttagcat  70920

tcagctaaag aaaagatcat agcccactgg ggagattagg aaaggcttca cagaagtggc  70980

atttgagcta cgccatgaag ataagttcct aagtatatct cagaggcaat accttaggca  71040

acaaaattat ctgtccaagt gacctccatg gtatttcccc tccagcacct caatctacct  71100

caactacgac gttagcttct accatgacga ggacagtacc tgccaccaca agagcccccg  71160

ggaccaccgt ccacagatcc acctaccaga accacagcac agagacacca agcctgacag  71220

ctgcagtccc aagctcagtt agtgtcccca gggctcccag catcagcccg tctaccctaa  71280

gccctgcaac cagcaaccac tcccagcact gtaaggaaat gagttctgca ttctttcatg  71340

acatgggagg gctcctaggg aagccaggaa gggggtatgt gataagacag aacctaccag  71400

agctgaatac tgcatatctt tgaggaggtt actgcatatc tgagagggag gtagagtacc  71460

agcctgcgat ttaggactca taggtgcccc taccttacag agggtcttgt aggaagctga  71520

gaccctgtga gcctcagttg cttctcttac aaagtggaaa taaccaccct tccacaacct  71580

gcttcacaag attgccatga tagacaaagg tgtaaccggt ataactggag gtgctcacgc  71640

acacagccgt tgctgactct gcgagggtgt gtgtgtctat gtttcacaaa gttctgatgt  71700

gtatatgagg aggtgtccct tgtgtttgga aagctctgat ctcagttcac agcaggtccc  71760

cagatagtaa tatctacaac catggtctcc ttatacctct ttccaaccct gggatgaaaa  71820

taattaagtt caccacttat taaatcattg ggagcagtaa ttgtcactgc tagaaatgtt  71880

ctatctcatt aatcagcaaa taccttttta attgagttac ctgccagagg gagttcattt  71940

aaaaggataa actatctttt taattttttc ccctacatgg acagcccaga aaccaagctg  72000

cttggcaaca tcttcctaac tggtcctatt tgccagcaga agctggcttt ttggagtgga  72060
```

```
gcacttactc cgaagtttgc agaggcagat ggagcatgtg tgaattccag ttcctctcat  72120
ctgagggcag agcctctcac cagcttctcc tcactggctt cctcatgctc taggttttaa  72180
tatcactgtc cagtgttcgc tgtggcccag agcagggagg acagcaggga ggacacagtt  72240
agctctggaa gcaagcagtg cagctttttc tccccttaac tgttagattc tcttggagta  72300
acatggataa acagtcacat tgagagagga tgggccttgg gccattgccg ggacagtcat  72360
ctcacctgca gcaagtgtag atgatagctc cttttcacac cacagggagc tgtcaggagg  72420
atctaaggga aaaatgcttt ctgaactata aagtgcttca caaatgttac aatgaagatg  72480
gttataagag tgagaaagat ggcatggcat agtttttcaa aaagacagta aattttccaa  72540
gcacttttca gtttaaaatg tgcttttaca tatcttttta aaatttagac cctattcaac  72600
aaccccatcc cactctccac cctcttagaa ctaggcaaag ttgtgccaag cattttatat  72660
tcattttaga taaattattt catttaatcc ttaccatatc cctaggaggt aggtaatatc  72720
accattttaa agatataaaa gtataatacc atgtgctgta tttataatat ataataattt  72780
gcccaaggtc acatgggtag tgagtagtag agctgggact tgaacccaga agtctgacac  72840
agaagtctgc gcttttgatt cctctacact atactatgtc ccatttcaat tacttatgaa  72900
aaataatctg ataatgcaga tggacagaca gttcacaaaa aacaatactg gcaaagcaac  72960
agatactgat ggaaaaaggc aaatgaccta gtccatcagc aacataaaga cctaagtgct  73020
cactttgcca tgcacagccc ccagcttcct actaccatga tgctatggaa agggtatggg  73080
acttgggaca tgagtcctgg gttcaagtcc cagctctgcc acttttctga aacccctcag  73140
ttaagactca gtttccttgc ctgtaaaatg gagataacct ctgtcctgct tgcctcacag  73200
gagttgtgat aggatctgga aagactgaat tattaggcaa cagccaggat catcatttta  73260
gaatgaggat gagcagcagt tgggtagttc ttaccacttg aggccagtag gggcttggac  73320
acacagtgat agagcatcat tctgcaaatg tttgtgtttt gcagatgcaa atgaagacag  73380
taagatgggc tcaacagtca ctgccgctgt tatcgggatc atcgtgccca taggtgagtg  73440
tggcccccag tcactgaaga gaaaagagag accctgctta ggcctaggga agagcgctag  73500
cagggtagag aacttggcct gccctattga cttgttctgc ccttgcagcc ttcctgccca  73560
cctcccagtc ctgatttaat ttggtttttt agcctagcac acaaggctct tcaggacctg  73620
gccccaggtg accttccagg tacatccccc atctccccac ccctcgattc acactctaca  73680
ctccagctat gtgaagtgcg actgtatgat ccctaggaac agggctggta tctcttgctc  73740
accattctcc ccagctcctg gcaatgtcta gcacatggta ggatatcaag gatttgttga  73800
attaatgaat agagctgctt accattcctt taataggtca tactgtcttg ttttctttct  73860
gtttggtttt caacaagtat ttattaagca gctactatgt gccaaactct gataagggga  73920
ggaaaggcag ttaaagatga ataagacatg gttctgtcct acaaaagttt atagtcttgt  73980
tagagagacc cacataacac agataagttc attacgacct ggtaggtcct aaggttaagc  74040
tgcatgcact gacttcagag acagtgctga ggaaacactt aacttgggct gggggagggg  74100
gaagagggaa gaggaggttt cctaacagaa gtgatatttg agctgggtca gccaagtgag  74160
ggaggatcaa gaacagtcca agcagtgaag acagcatgag taaagccagg agtaggaaat  74220
ggcctggaag ggtcagggtg gggtgggttt agagctagaa ggagatcagt atggccagag  74280
tataacactt tgttaagacc tcacagagaa tcatgggggc tgattcattc tcttccaccc  74340
tgatgaccac acggtatcct gtacacccct ctcttagcag tctcatctcg tagcagtatc  74400
```

```
tttgcattct gattgtccat tcagagcttt atctccctta cttggctatg agtacttcaa  74460
ggacaggaac tttgtccttt tatcctggga atcttcagta tgccgagtta gtcagcaaat  74520
gttttaaaaa cttctcccct gtgtaagaca ctgactgtgc caagtgccaa ggatccaggg  74580
aagaaaaaaa taaagacttt aagagctttc agtctttaat caggcaaaaa taaagtcctt  74640
taaggtagat gttaatacat gtcattatgt gctatgatag gggcatgttg gatatagata  74700
gagacagagg aacaatgtaa tagtggcatg atactcttgt gaagggatgg tagaaggaaa  74760
ggtaattcca gagtaaaagt ggcgcttctg gagaagacag catttgaatt ggccttgaaa  74820
ggcttcacca ggaaagatga tggtgaggtg attattccag gattattttg attggagtgg  74880
agaaagataa atctacccct ttcttgccat cctttgccct atagaaagag gcagatatat  74940
gctgttttgc tgacataact cactctgaaa tattcaatat ttttaatttc tgctaatctg  75000
aggagtgaaa gatgagtatt atttccctga catttccctg tgaggtagag tatattttcg  75060
taagcttatc agccccttta cttatatttt atctgttatg aatcgcccac tcacagtctt  75120
ttcttatttt tctattggct atctttttct tatttataga aatatttata catgacaaat  75180
attaaacctt taaaatatat gttacaaata ttttcttcca gtctgacatt tggttttaaa  75240
gtttgtttat ggtatctttt gccatgcata aatatgaaac ttttaagtat cagatttgtc  75300
aatcttttaa gatttctggg ttttgtgtct tgcttaagaa ggccagcctc actctaactt  75360
attaaaatat ctcctgatgt ttttcttttc tactttaaac ttttttttag tattaggata  75420
ttaatctatt tggaatttaa attttagagt atcgtatgag gtagagattt aactgttttt  75480
ttctctatat acctgtctag tttccccaaa accatcattg aataatccat acttctctcc  75540
tgacttgcac gtcatcttta ttataaacta cctcccatac gtactttgat ttgcgtctaa  75600
gcagtttatt ttccttcact gatttatata ttcctacata ctattagcac aacttcatga  75660
tatgttatgc tcacaacatc ttctcagcta tttttattca gtttctcttc taggtgaact  75720
tcagaataat cttatcaatt ctataaaaat tttggtgaag tttttatcaa gattgtttta  75780
gatatatgag tttatgtgag gagaatatac ctttttatta tattaaagct tcccatccag  75840
aaatgtggcc tatttatttc agtcttcttt tacgtccctc agcagaattt tatagattac  75900
acaggacttg cgtatttctt cttaggtttt cctaggtatt ttatagcttt tgatgggcta  75960
ttacgaatgt atttttattc cattactttt tctttttctt tttcttttta agagacaaga  76020
agatcttgca ctcttgccca ggctggagtg cagtggtgcg atcacagttc actgcatcct  76080
cgaactcctg ggctcaaggg attctcctgc ctcagcatcc cgagtagctg ggactacagg  76140
catgcaccac cacacctggc taattttttta aattaatttt tttgtaaaga ccagggctca  76200
ccatcttgcc cgggctggtc ttgaactcca gggttcaagc aatcctcctg cctcagcctc  76260
ccaaaatgtt ggtattacat atgtgagcca ctgtgcctgg cctccgttaa attttctaat  76320
tggttgttgc tgattaaaaa gacggctaat gatcttttat gttgattctt gattaactaa  76380
aattatttct gatagttttt caccagcttc tcttaagagt ttctaaaaat acaaatagct  76440
gttaataaca gtttggtttc ctcctttctc atatgtattt atttatttac tttttttttt  76500
tttttttga gacaaggtct cactctgttg cccaggctgg agtgcagtgg catgattgtg  76560
gctcactgca gccttgacct cccaggctca agcaatcctc ccacctcagc cttctgagta  76620
gctgggacta caggtgcccg ccaccatgcc caactacttt gtattttttg tagagatggg  76680
ttttcgccat gttggccagg ctggtctcga actcctggcc tcaagtaatc tgcctgcctc  76740
agcctcccac agtgttggga ttacaggcgt gagccaccgc acctgggctc ctttcccata  76800
```

```
tttataccct taaatttttt tctggcctta ctgcatagct agatctctaa gacaataaat  76860
attagcaatg ataactgcct tgttcctgtc tttaatgctt atcaattatt gtaatcttac  76920
taaaacagaa accccttcca tagcatccta gataggtgat cattcagcct ccactgggat  76980
gctcagagtg actgctaatc accttacaaa gctacttgct ccatttttac ccagctgtgt  77040
tggagagagc ttcctccttt aatcattaac atagtcattt attctaaatc agagcttgtg  77100
ttgccctctg tgtctccttc tagagatgtt cttcttcagg tggagcctca cctttggaaa  77160
taaacactct gcctggcccc atcccactct ccacccccca gttttgggag agaatcgttt  77220
tcttagagaa atctagggaa gcagcagcat tagggcaaag gtgtggtaaa attcactcat  77280
tcattcagca catgttacta ggcacctagt cagtgctagg aactgggcgt agagagttta  77340
aaaacaaaaa aaagacacag tccctgcctt gaaagagcta tctagttggg agtacagata  77400
cataaagtaa gatactgtgt gtgatctggg agcacacatg agagagcaac tgactctgcc  77460
cacagttggg gaagacttca catttgaaca ggatcttgaa ggatgaatag ttagtaaagg  77520
aaagaaggga tgagagatgg gctttcaaac agcagtaaaa gaacatgcag aaacagagcc  77580
tgaggagcaa agggtagtaa aagtggagtg gtgacaagcc ttgtacagat gtctgagcag  77640
tgggttggag cctgctggag gtccagtgtc ctgtgtcctt cctccagtgg tgatagccct  77700
cctgtgcatg agtggatacc tgatctggag aaactggaag cggaagaaca ccaaaagcat  77760
gaattttgac aacccagtct acaggaaaac aacagaagaa gaagacgaag atgagctcca  77820
tatagggaga actgctcaga ttggccatgt ctatcctgca gtaagtattt ctcactggga  77880
gaattcctac cttccgacca tcttcccttc catcctttct tcccctccca tcctttcttc  77940
cttcccatcc tttcttccct cccttccttc cttccgtcct tccctccctc ctttccttcc  78000
gtccttccct ccctccctgt ctttttttctt tccttctttc cttcctttcc tccctccttc  78060
ccttcctcct tctttccttc ctcaaacatt tatcaaaaac gcaccatgta tcaggcactg  78120
ttctaggccc tggggaacac agaaatgctg gggtaggtgg ttaaggtaaa aaggtatcag  78180
gaccaccttg tacctagagg ctcttcctgg cagtaaaaaa agccaaatgt ctctctttct  78240
gctcagtaaa ttttcagaac ctttagcctg gaagggtaac tgtggccatt taattcaaat  78300
gtattcattt caatactgta tgccagttat gtgccaagca ccacattaga tatcaagtat  78360
tcaaaagtca ataaggaaca tgcttgctcc caagaagctg gtagggagtt agagatacta  78420
acatacagtg gtataattgt gtgctgaatg ccgtggtgga agctcaggag tcccctcttc  78480
tagaaagcta tctttggctt gctttgttct cccacagtac tctgggcctc tctacctcac  78540
agcccctgtc acactgtagt ccacttgtct tttactcagt ggtctcctca ctaacccata  78600
agatccttga gggcagaact gtctgattaa tctgttttcc tgatgcctag cacggcatgg  78660
ctgactccca acaaatattt gttgaacaga tgccatggaa acatcaacaa gggagctatt  78720
aattctgtct ggggaatcag gcaaggaatg cctcacagag aaggtgacag atggactatg  78780
tccttgaaag attaatagca gttttcccgg gagagaagga gggaaatggc attccagata  78840
gaggcatgtg caaaggcttg aaggtacaac acagcatggc tttttggggg aatgaggacc  78900
acaaagtggc acagcaggtg tcactgttat acagcacagt cagggggctg agtgtgacct  78960
cagaggtcat ccacagtgcc atccccctgt caggcaatca gcagctttga tcgcccactg  79020
tgggcagagc cctgtcttgg ggagaccaga gaaccggaag acccagcccc tgccctcaag  79080
gagcttttttg tcttgccggg ggaaccaagg tcacagctgc accaactccc gaagaaccct  79140
```

```
ctttccgagc tgcctgtcgt caaatccaag gtagggcagt gccactctaa gtctgagggg  79200
ctggtgagtg agggcatgaa ccaaggcagg cgcagccaat cctagaaggc tttctggttt  79260
gggaaggctg caaattgtaa gctgggtgtt ggggcaaaga agaaaaatgg gttagtcaca  79320
gaccaatgaa tggcatgtgg aagaaagcaa tcaagtttgg ggcagggcag acagaattgc  79380
tgctgaggca aactgttcat gaaggggaga catgggaaat gagatggagc aaatgaggag  79440
ggttagcaga tggccttgag gatccttaac ctcggccagt ccaaaaaaat agttgcttga  79500
ccagtttttg aagatcagag ggagcacagt ggaagaagca ctgaacttgg aataagaaaa  79560
ctcccagttc catccttcca ctgccctgtg atctcagtca cttctttctg ctcactgtta  79620
tttgtaaaat gagaataaca acccccattc tacctgcctc ctgagtttat aaagtacaag  79680
tgagatagca cgtgtgagag cactttgtga cttacaaagc actctgcaca tgtaaagtga  79740
cattatttcc agagaaagaa atgactcagg gggagttact cccgatgagt gttaaggacc  79800
aagtaataag cttctgccag ttgcagagaa ataaggaaat caacatttag tgagcaccta  79860
ctgtgtgtca gacactgttc ccagtgtttt acatatattt tctcatttaa tcttcataat  79920
aaccttatca agctgatatt attcgcccca ttttgcagat gaggaaactg agactcatag  79980
aaattgaata acttgcctaa ggtcatagcc aggaagtggc agaaccagaa ttcaaactcc  80040
agtctgtata tacacaaaag cccatgctct ttcctttata tcgtgaggta aatagccttg  80100
aagctctgga aatcaatatt ctcaacaacc tgtctctcct ctgtccattt ctcggataac  80160
tgtaccatca ctactggggc ctatctttgg cctagagatc tgtcttagag agagtgggag  80220
ggtagctaga ctagaataag atagtcttaa atatctacac tggtggagga tggccattgc  80280
attcataaaa aaactacaga taacccaaag atgacttgaa aggcagtaga gttacttttt  80340
atcatatgta gaatgtccag agatgggaga tactagtctg attctatttt atgttggtta  80400
cgttgaccta ggatattctg ggccctatgt gttgttaggt actatgttaa acactctctg  80460
tgcattatct catttgattc ctcaacaacc ctgtgaggta ggtcctgtta ctattcccat  80520
ttgatagatg ataaaactaa gtctcagaga agtaaagtgg ctggcccaaa ttcacataac  80580
tatgaggaaa agtactgaag ctggggaggg tctttccaaa ggagggtatc tgggaaatgg  80640
aaaagaggca aacaagatta catcaggact agctggggaa agttagatgt gtaccctgga  80700
gaagaaaaca ctcagaatga acggaaggga attcaaacac catctataaa tttcaagggt  80760
tgtcctatgt agaactgtct ctgagtctga gatggaatca gggaatgtca gaagatataa  80820
acaaacaaat ttcacattaa tataggaaag aatttaaatc tgttgtccac aatggaatag  80880
actggttcag gggttagtgg gctcaccttc ccatggtcag ccatttttgg cagacaggag  80940
tctagcatct acctaatgac tggaaagcag gggtgaggga gagagggatg gaatttaatt  81000
aacctgcatt gcctcccaac tgtgtttaat ctgttgggaa ggtgcagtat attacctttc  81060
taaatgtgat tagcatgcta gagacaagta accccatagc ctgaaattta acatttgcca  81120
aagctaaccc actgaaattg accaaaccta aaatcctata agggaggatt aagaaaattt  81180
agatctgtgc aactcttctt tacaaagata caaaacagaa tgatgaaaaa atctacagct  81240
ttggattcat acagacctgg gatcaaattt tagttcagcc acttgctatg tgatccagaa  81300
caaaccctac ttaagctcat tgagttttgt ttctcatctg taaaataaat aggataaatc  81360
ctgtctctta ggatagtttg aacattatgt gagctaatac ctgttaaagt aacgtaagtc  81420
tgtgatttgt caatactaaa taaatagtaa ctcttatgga tctaatgatg aattctttgg  81480
tttgtctccc cagcgagtgg cattaagcct tgaagatgat ggactaccct gaggatggga  81540
```

```
tcacccccttt cgtgcctcat ggaattcagt cccatgcact acactctgga tggtgtatga  81600
ctggatgaat gggtttctat atatgggtct gtgtgagtgt atgtgtgtgt gtgatttttt  81660
ttttaaattt atgttgcgga aaggtaacca caaagttatg atgaactgca aacatccaaa  81720
ggatgtgaga gtttttctat gtataatgtt ttatacactt tttaactggt tgcactaccc  81780
atgaggaatt cgtggaatgg ctactgctga ctaacatgat gcacataacc aaatgggggc  81840
caatggcaca gtaccttact catcatttaa aaactatatt tacagaagat gtttggttgc  81900
tggggggggct tttttaggtt ttggggcatt tgttttttgt aaataagatg attatgcttt  81960
gtggctatcc atcaacataa gtaaaaaaaa aaaaaaaaca cttcaactcc ctcccccatt  82020
tagattattt attaacatat tttaaaaatc agatgagttc tataaataat ttagagaagt  82080
gagagtattt atttttggca tgtttggccc accacacaga ctctgtgtgt gtatgtgtgt  82140
gtttatatgt gtatgtgtgt gacagaaaaa tctgtagaga agaggcacat ctatggctac  82200
tgttcaaata cataaagata aatttatttt cacacagtcc acaaggggta tatcttgtag  82260
ttttcagaaa agcctttgga aatctggatc agaaaataga taccatggtt tgtgcaatta  82320
tgtagtaaaa aaggcaaatc ttttcacctc tggctattcc tgagacccca ggaagtcagg  82380
aaaagccttt cagctcaccc atggctgctg tgactcctac cagggctttc ttggctttgg  82440
cgaaggtcag tgtacagaca ttccatggta ccagagtgct cagaaactca agataggata  82500
tgcctcaccc tcagctactc cttgttttaa agttcagctc tttgagtaac ttcttcaatt  82560
tctttcagga cacttgggtt gaattcagta agtttcctct gaagcaccct gaagggtgcc  82620
atccttacag agctaagtgg agacgtttcc agatcagccc aagtttacta tagagactgg  82680
cccaggcact gaatgtctag gacatgctgt ggatgaagat aaagatggtg gaataggttt  82740
tatcacatct cttatttctc ttttcccctt actctctacc atttccttta tgtggggaaa  82800
cattttaagg taataaatag gttacttacc atcatatgtt catatagatg aaactaattt  82860
ttggcttaag tcagaacaac tggccaaaat tgaagtcata tttgaggggg gaaatggcat  82920
acgcaatatt atattatatt ggatatttat gttcacacag gaatttggtt tactgctttg  82980
taaataaaag gaaaaactcc gggtatatgt atagatgttc ttcattatag acatcttctt  83040
tgcttttctt ggccttgggg gaggaaggga gaagtgctct tttctacttg tggggtctcc  83100
cattggaaac ataatcctat agtcccagaa ggattcagtc cccagtggct ttcccatcca  83160
aagagaaaga gtttgagttt cttaactctg ctgttctgcc acttactccc actagacaac  83220
cagggacaag gtgcaacatg gaagtgtttg acttaagtag gagcagagga gctgcatcta  83280
atctcatcat acctggaact tgacacactt aagcaaatgc cttcccatcc ctacctgcca  83340
gatgccccca actcaatgaa gttggatgtc tcaccagctt gatacccttt gaattttcag  83400
tcagacattc                                                         83410
```

<210> SEQ ID NO 2
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2

```
ttagtttaat cacgctcg                                                18
```

<210> SEQ ID NO 3

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3
cctgctgtgc cactttgt 18

<210> SEQ ID NO 4
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 4
tgacacctgc tgtgccac 18

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 5
aacagtgaca cctgctgt 18

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
tgtataacag tgacacct 18

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 7
tgtgctgtat aacagtga 18

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
ctgactgtgc tgtataac 18

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
gccccctgac tgtgctgt 18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
actcagcccc ctgactgt 18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
gtcacactca gccccctg 18

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 12
ctgaggtcac actcagcc 18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13
gacctctgag gtcacact 18

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
tggatgacct ctgaggtc 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
cactgtggat gacctctg 18

<210> SEQ ID NO 16
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 16
agagtggcac tgccctac 18

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
gacttagagt ggcactgc 18

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
cctcagactt agagtggc 18

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
cagcccctca gacttaga 18

<210> SEQ ID NO 20
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 20
ctcaccagcc cctcagac 18

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
cctcactcac cagcccct 18

<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 22
catgccctca ctcaccag 18

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 23
tggttcatgc cctcactc 18

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
tgccttggtt catgccct 18

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 25
gcgcctgcct tggttcat 18

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
tggctgcgcc tgccttgg 18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
aggattggct gcgcctgc 18

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
cttctaggat tggctgcg 18

<210> SEQ ID NO 29
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 29
aaagccttct aggattgg 18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
accagaaagc cttctagg 18

<210> SEQ ID NO 31
<211> LENGTH: 76601
<212> TYPE: DNA
<213> ORGANISM: Mus musculus

<400> SEQUENCE: 31
tctttctttc tttctctctc tctctctctc tctctctctt tctctctttc tctctttctc 60
tctttctctc tttctttctt tctttctttc tttctttctt tctttctttc tttctttctt 120
tctttctttc tttctttctt tcttcctttt tttttttctg aagagagagg gcctatttaa 180
cactgggcct tggcaccctc gcgcgggcct ggtttacaac ccgtgcccaa gaatcacact 240
ctgagattgt tgtgctgctg ggccaggctc accggcaggt ggctgaaatc cagtctaagc 300
gttgcccttc tgacaaggaa gagtagggga ggtggggtcg cactgctaga ggaggggcct 360
tctttgtgca gaggctagtg gagcccagag acactagatg tgctgcctct ggcggcaagg 420
atgacacatc tgggcctcca cagtccttgc ccttctctgc agcagcaagg gttaccttgc 480
catgtcttca gggcccttga tctgctcctc tgcggggtcc aacagagaag gatgaatatg 540
gataacagtc tgtgcaccag acactcacct ctctcaggat cacacagtga taatcacaga 600
tgcacacggt cgcagaaagc gactcatcta atctgaagct atgacaggtc ttgcccagca 660
cccctagatt ctccctggca atgctttcag ccttcccgcg ctctgcgcgt tcactgcaac 720
ggcttgtgag tctccttctc ccgagctcgg gctctcctcc atacgcctcc ttctctcacc 780
ctcttgccac ctccacgggg aaaccagggg ggccagagcc tagccgggct cgtcctagcg 840
tctacagctc ttagcacctg cgcgcacaca gagcaggatc atggggctcg gaccgagaga 900
ggaggggaca aggacaggcg ggggaggaga agaggcggcg gcgggaggag cgtggggcgg 960
aggcggcggc gggagggagc gcgcgcgccg gcggcggctg cccagggccg gggccgcgcg 1020
cccagcctga gcccgccccg ccgccgagcg tcaccgaacc tgcttgaaat gcagccgggg 1080
agccggggcg ggcggcagcg gtggtggtgg cggcggcggc agcggcagcc ccggcgccgc 1140
ggcaaggact tggcgggctg aggcgcggcg gcggcgcggg ggtctcgggg cgcggcggcc 1200
ggagccccgg gcccgctatg ggccgcccag aactgggcgc gctccggccg ctggcgctgt 1260
tgctgttgct gctgctgcag cttcagcatc tctccgcagc ggatccgctg ccgggcggcc 1320
aaggtgcgta cggcgcttcc cgggccggct cgcagccgcc aaccaacaaa gcgcggccgg 1380
cggtgggggt tgctgtacgg cgaggtcccg atagagaggc tccggggacc ctagctccct 1440
ggatttgcct tggacctcct ccccgctacc cccacggttt tggttaccga agctctaccc 1500
cagctccggg caccctctta atgggggatg ggcgccgggc accccccccc cggcccgtga 1560
actttgcggg gggtagtcct tcagggtctg gggtttggtt taatttgaca cgcgcgctcc 1620

```
atagcggcga tgagcgaagt ggtacagtct tttctgacaa tgcgtttccg ggacccctg   1680
tgggccgagg agactgacag gttgtgaagg gactgagccc ctgcaccggg tgcgtgtcgc   1740
cagtgtgcgg ggcttcccgc agactaggtt tgtgtggacc tgacttggcg ttgtgtgtaa   1800
gggtgaatgt gtctgaaggc ggggtatagc cacgggccgt taagcgcttg tcgggtctcg   1860
ctgtgccatc agtcggtcct gcagtggagg acccgtggca tcctgtcctt tctcggaatt   1920
aaggtgcttg gagatccaga gctcaccgat atctccccct ttcccatacc cgctggactt   1980
ctcggcagcc agggctgcag ggtggggagc gggctcctgt gcagtgaccc agctcaccgc   2040
ccccaacccc cgcagggcca gtcaaggagt gtgaagagga ccagtttcgg tgtcggaacg   2100
agcgctgcat tcccttggtg tggagatgcg atgaggacaa cgactgctcg gacaacagcg   2160
acgaggacga ctgccgtgag tcgcggcgac caggggaggg gaaacggggg gggggggga   2220
tcatgctccg ctgcgcacgt ggctgcatcc gtcatggggc cacctgcccc aggctggcgg   2280
ccttgttctg ggatgggtgg ctcagctgtc ggcgggagct gggtggcagg cgtgtcctgc   2340
ttagggtgga gcccagcgcg gcttgctgaa gctactagcc cgagactgtg ggcgtggacg   2400
cggcagcccc tgcacacctc ttagctctat ggatcggatc cccaatctgg gcctcactgg   2460
gagcgcgcac ttcaaagttc cacgcagctc gggccacgag gggcttttcc ttgctcggtt   2520
ttatgaatga atgggctccc cggggccact gattggctgc gcaaggacca ccccataggc   2580
ctgtggccgg agcggccaat cctggggctg acggtgtgct gtaaagggct ctaggccctg   2640
ccctggcccg ccccggccgc acccccgcgc gcatcctccg ggtggtaggc tcaggtcctg   2700
gtcacagtct gctgcctttc tgccgagtca cccttcagag agcgttttcc tcctgccagc   2760
ctagtctggg tgtgagtcat ggggccaaca gcaaggaggg gctcaggagg aagagtgtgt   2820
ttcctggaag ccaccggagc aacggcagtg aaggcaggcc aaatgctaac cccactgcct   2880
ttgctgagcg tggcctttgt acaccctgtg caaccggtgg aagttccccc ttgtgcgggc   2940
gcgtgagggg tgtctttggg gccagcggca atggagtcag caggcgttct ctgctgtgaa   3000
aggaatttag ttcctggtac caagaaccta cactcttcta gccacgtctt cctaggaggc   3060
ctttcagttg tcattacaga ggcctgctgt ctgcctgccg atgttaggtg tacaggatca   3120
ggccggccgg ctctgcagtg tcggaacaca gtgacagaat gtggaggaca ccaggtgggc   3180
acacaccaag cattcaggaa cgggaggctg agcaacaact cgggagcagt ctgttaagtc   3240
cttgaggctt cctggtttaa cattttttg gggtggggta catttgtaaa gcatgtatgt   3300
gaagataaga gtaaaacttt cgggagtcaa ttctctccta ctttgttggg tctctgcctc   3360
caacttagca tcctccagct tgtctgcgat gcctccaccc gcccagccgt cttattggtt   3420
ctcatggagc tcacaggcaa gcagagatct tccttgagtt cttttgactg ttcacttgct   3480
ggtcagcctg gcagttctct ctggtctagc ttagaccaga ctttcgggca tcagagcctg   3540
actgcctcag tttcccattt gagttgtaac tacagcctgt ggtggactaa cactcttcac   3600
agaggtttat gctacagatg aaaacaggct ccagggttga gttacctgct ctgtggctac   3660
tgagttgcca agtggaagcc tggtcttagg catcttctac cagagttctt agcctaatcc   3720
ttgttctatg ctatggctgt ggttgggtaa aatatcaaga ggggatttca tgcctaggag   3780
ttgttctggt tttcttagag ggtgcacac aggacagggt gcagaaatag aaaccttgta   3840
tcgtatcccc ttaggtcttt aaaacactag tcttgtgagt gtgattgtca ttttgtaggt   3900
agagatagtg gctcagagag atggggtggt gttgtgtttt accgaaggtc acacagcata   3960
```

```
ggcaggatgg atggcagaac ttggtcaaga tctctgcctg cctgttagct cagggcatga   4020
gttgatgtag aagggagtgt ggtgtggaca ggagggcctt ctgctcttca cttatgaagg   4080
tgcataggtg gctggtaacc tgagatggga ttaggagatc tttgaggcag tcgggcagct   4140
gctttggttt gaaatggatg aggcagggtt ctgggcagat gttcatggtg cccgtggtgt   4200
ggagaagaac gtatgttgca cacggcttga ctccctgagc ttgcttcctc gggctcccgc   4260
caggatgcct gtctccatct ctgttctata ttagatcaca ggaagtctcg tgggactggc   4320
aagaagggga ggggaaggta tttggaaatt cttctcccca gaactggaga gatagctcag   4380
cagttaaaat acttagtgct cttgcagagg accagagttg agttccaagc atctacaccc   4440
acgcccagca tctcacaact gatctgactc cctcttgtgg cctctgtggg cacacagaga   4500
cacacactga ggacacacca ttccgggcca cctgctcaga ctcaccccac ccctgatact   4560
tcactctgct ctgtccacag gggcctggt tgctcagcct ctctttgccc ttaggctgca   4620
aaacagagtg gggggaagag ttgtaatgta tgaaactgtc cagtgtaggc acaatgaacc   4680
caagtgtctg atgcagccca agtatgaggg agctgaaggg aaggagggag cttttgcact   4740
gaggagactg agacaggctt cctatagaag gctactgcag agctcatccc tagaagagtc   4800
acttgagact tgtcatcata aaataaggga cacaggtggg gtacagtggg gcgtgccttt   4860
aatcacagca gttgggaggc agaggcaaaa ggatgtcttt gagtttgaga ccagcctggt   4920
ctacacagtg agtttcagtc ccactaatgc tacatagtga gaccctgtct caacaaacac   4980
aaaaggtggg acagacctca tgctacagag gtcaccacca gttctcagag aggtaacccg   5040
actcaagtca tacagcttgt ccttggctct ggaactcaca ctgaggtctt gatctttagc   5100
ttcagggagg gttcttggcc cacagctggc gggctaggga agggaagcac actggagctt   5160
cagttcccaa ggtgccttca aagcggagga agggtctgtc gccctagggc tccagccagg   5220
ggaagttggg tgggactcca gcctgtgggt tcacgtaggc ctgggtttcc tgttgctttc   5280
tggcgtctgg gagcagaggt ggggattctg gtcgctggcc aggcctttgc tcctggacca   5340
tcaaacacag cacctattca cacttgtcaa gcattcggga actccaggca gctagcccgg   5400
gccatgtgcc tctctctgcc ggtgctcctc agtctataag atggttgagc ctgggaggcc   5460
tgagccatct ccaccttgta gaagctcaga gggggtaagg aacagtgtgt ttaagtaaaa   5520
ttgcttcagt gtgcattcag gcatgcagcc acggagcctg cacaggcccc ccccaggcct   5580
ccatttctca tcctgaggtg tgtgagactc ccgactgccc cagctcctgg agtgctggac   5640
tgttttgtgg gagattggat caggaagctc cttctctgta ctcacctgct tttcccttgc   5700
cttagctctc tgccgccatc catccatccc actcagtgaa gagctgctat agcccagcct   5760
cccaggcttc aggcccacta gatggtcctg gccaggccac agggattcca gagcttgcct   5820
ggtggtggcc ttatgaatga tgacagtttg gctacaggtc ctggcttgtg atgtagcaca   5880
catttggctg tggggtacag ttaaccaaga caccaggccc agcttcattg tccctttgga   5940
tagatgacat cattgacaaa gagctgttct tctctgaacc ttggctttcc tgtctcagct   6000
gttgtgccac ctgaggatgg agcctgtgct gtgacttctt tgttccttgt gcccgctgcc   6060
ctccagcctt ttcctgcgtc cttctctgag ccccgccacc gctgcagctc cgtcacctgc   6120
cttctgcttc tcacctccag gcctttgtgt gtgctgcttg ctttctcagg acactgttcc   6180
cgcccatgct ccctgcgttc cctgtggttc tcaacctgtg ggtcatgacc ccatgggggg   6240
gggagtcacg gatctgatat tctgcatatc agatatttac attatatttc atagcagtag   6300
caaattacag ttatgaagca gttacaacat aattttgtaa tatcataatg tataataaat   6360
```

```
aatattgtaa ttatatgagg aactctatta aagggttgca gcattaggaa ggttgagaac   6420
cgctgagatg aggactttct ctttgaagaa ggtgcctctg ttccctcagg ctgaggtaag   6480
ggacttcagg aatactgaaa tcccaactct gtgcagccct gaatcagata aactcagctg   6540
tccccttctg gctgaatggc cctggtgaca atagtgtctc cttcttagag atgtgtggta   6600
aactgaaatg tgctcagtga gcaggaggcg aatgatgggt ggcagtgggt agcatggtgg   6660
gcgaaactca gctgaacacc tctaaggttg ctactacagc agccacccaa accctactcc   6720
acaacaagag tttctgaagg ctccagcagg gggtgtggct ccagtagggg gtgtggctcc   6780
agcagggggt gtggctccag taggggtggt ggtggtggtg gtatgtgtgg cttcaggtag   6840
tgcatgatgg tacagccaca acggaggtgg cttcaaggat acctagaggt gcagaacgta   6900
ttcagggagg gctggggaag aaatgaatct tacagatgtg gctggtctct gaaagtaggc   6960
tggggctggg aggggcagat cctggtgggc agcctcttac ttctctcttt ctagctgagt   7020
ctgttatacc gtgacactgc cacaggctcc aggcttgact agccgtctgt gccgctggat   7080
tcttccagca ggacttgagg gtgctgaagg ctctctcttg ggctttccat ggcccctcct   7140
gggtgagagt cccctcagtt tccaaggctg tagctggctc atggctgtgt ctcccccctc   7200
accatccccc cccccttgct gctgctgctg ctgctgactg acagctttcc tcctcggaga   7260
atgaggtagc aggtgaatcc gagggacctc agggatagag gaagaacagg tcccagagag   7320
ctggtggaac aaacacccct tcagggtata gtcaggtggc gttctcctgg cccagggtga   7380
atggtcatgt ctccaaggcc ctcattgttc caggaaagtg gctgggtctc tggaggtgca   7440
ggcgccacct ctcccagggt acctttcctt acactgtcct ctcagactct ttcttactgc   7500
tagccctgtg cttggcatca gggactccag aacagatacc ttcctctgga gatctccagc   7560
aacaggtact ggctactggc ctgtgggtgt gttgggcagt ttattttctt cagctcttct   7620
tatctctgtt taattcttat tcctgtttta aaagaggaaa cagaggctta gagagaaatg   7680
gctgtgtgct gcatatggcc tggtgcttct gggctggagc tctgccatgt aaaaatgact   7740
gccttagctc ccccctccct ccctcccttc ctccctccct ccctccctct ctcctgtccc   7800
tactaatgtc ccttttcata tttattcctc ttgagacatg gtctcactct gtagaccagg   7860
ctgatcttga attcacaata atcctcctgc ctcagccacc tgagtgctat gattacaaat   7920
gcaaatcagc ttctctctca ggtctgtcca ctctgttggg gtcaaaggac acattgccca   7980
ggcttgtctc cctgtggtaa aagtttctgt cctggggagt gggcctggaa gggatcgtct   8040
ctggagaccc catggagtcc caacgcaggc cccctctcct agactggtgg gcttttgtta   8100
gctgtgccat tgagaaagga gaacctgaca gtggccctgg aaagcaatgt cagctcgttg   8160
tcacagcttc acctggactc tgcctcctgg ctgccagacc tctggtgccg tcagggccca   8220
ttctcaggag cagggtgttc cgctcctgag tgggcctgga ggaagaaaag cagacatacc   8280
ccctcccact cttgcacacc cacccgccgt gcctctgttc tgtgtctagc taagggacat   8340
aaacatgcct gccacacccc agagctttgg gctctggtat tggggactgc aggcatatac   8400
tgtcctggct gggccctacc tggcctctca ggatgtctgg caagcatggt aaagtgattt   8460
gttctgtgtc catggcttcc tgagtgctct ttgctgggtc ttacttaaca caaggcctct   8520
aggcaaggcc tggcagtatg agattgcatg ttgtagaaga caacgcggag aaccaaagtt   8580
gcttgcccta agttagctga ctggtcaggg gttggacttc cttctggctg tggggtctgc   8640
tgtagccgga aggaggagtc cagttcacac acatcagtca ggagagcgtg tcggatccct   8700
```

```
taggtgtgcc ccagcttccc tttccaagta ttctaggtac tcggtcagtc cttgtcatag   8760

ggtgtgctgg ctccctcctg agcaatacta gccctggggt gcccttggcc atcaatcagg   8820

aaggacccct ggttgcagct gtttctcctg ctacaagctg ctatgtcacc caccctgggg   8880

ctggaaaggc ccaagaagag cttaggggag aagagaaggt gcctataggg ggactctgct   8940

cagtaccaac tctatgcttc tcaccaccat tctggtggcc tctgttcagt gggggccagt   9000

ccgggaccca tagctaggag agttgggcct tgggagtatg gactctgaga tcctatcagg   9060

actcttgaat gtcctgatga ctaagtgacc cagcaccgtc cacccagttc ccatgacccc   9120

ttactgcctc tgcctacaat cttcagggtt tattaatttt gtgtgtatga atcttttgcc   9180

tgtatatatg tatataccat acgagtgcct agggcctgtg gggtaagaa gagggtgtta   9240

catctcttgg aattggagtt atgggtgatt gtgaaccacc atgtgggtgc tgggaatcaa   9300

acctgggtcc ttgacaagag gaacacatgc tcttaactgc tgagctgtct ctccagcccc   9360

aaacactgcc ttctagaaca tggcaggaca aacaggcaaa agtcttcctg ggaaactgca   9420

cccaccaaag ccatgggagt ggtcctgtgg cccccggcgg taccccggac actggcctga   9480

ccgtcctaca aggaacttca cccccattac tctatcagtt tcctgtcacc agcctgtcac   9540

actcagtact gccccataga cacgcacctg ggcggccgac gaaggcagtg cataggtccc   9600

actgccctga agaggaattt caggctaagg agcctcacag gacttcctct gttactggaa   9660

gttctggagc cacagcttca gttgattctg tttattcgtt tttatttttc cttacagaaa   9720

tagccttttc tgattacacg gaagtaattc tctaaaagaa aaatgaggtc ctgttattca   9780

gatcatttc tcatcatata cagtgtccca tgccagtaac atacattact aaattctttg   9840

gtctttatag ctagactcta actaaaaaca aaaacaaagc aaaatacata atactgagac   9900

aaacaacaaa agatgacgtc atcttaggaa cacccctgta tgccctaatg gccctggtgt   9960

ccagccagcc cacaggatcc taagcacagg gccatcttgt cccagcccca atgacacaga  10020

caaagtagcc atatctgggt cgcacagagc agagataaag ggcaactgtg tcctggccca  10080

aggacactta gccaccaaaa aaacccacaa tataaccaaa cgattgcttc atttgtctca  10140

acacattagt agaacccatc tccctcttag ctttgcaatg attattctgt ttctttccca  10200

aactggctgt gtgacttgga caagtggctt ccccatctga acttcatttc tctcttcatt  10260

cattggtcct tgctttatca gcacttcagg gccctctgag catcaaactc ctgcctgggt  10320

ctgagctcag ggctggagca agcctgggag gatgggagac taccctgagc tagatatggg  10380

tctgggcctg tagagagagc agttgggcat tttagggtcc agaactcagc cgcaaggcgc  10440

agacttcttt ttcccctctg cgtgctcctg gctgggttgg ataagtacgg tgatggaggg  10500

aagagaacag acagagaggc tcgaggcttg tctgcccctc atgccgtcct gaagcagcca  10560

cagcatggag gtgtgaagac cagtgggtga acatccccag accttcctga acacgtgatt  10620

cctgcatacg tcagctgtcc tccgccaagg gcgcagcaag agggcagccg ctgggagaac  10680

agcaggagag ttagatgtag gtcagctgcc cggagggaag gaggggccag gctgcaatag  10740

tgcctcagcg gtcactccca tcctgactgc tgtggagccc agggcatctt ctaggtggcc  10800

ccaggagcta gtttaccctg ggttcacagt gggtccaggg ggatatcagg gacatggcag  10860

ctgatgagag gcaggaaggt cccaccaggc ccaggttaag gtacctggct gagtggctgg  10920

aggcagcgtg ggctttcctg atggcctgaa tccagggaca ttcaaaccag ccccctccat  10980

gcccacttcc tagaccttgg tctaccatct gctgcccatc atccttaaag cccagggttt  11040

ttttttttt tttttttttc tgttctagag acagaaagga catgacattg tgtgagtagg  11100
```

```
gagatggcaa ggatctggga agggatcagg ggaagggaaa agagtatgtc aaaatatagt  11160
gtataaaatt ttttatttaa aaaaagtccc ttcttttgac tataaccagg agtgaagtgg  11220
gcattctgga caaaccaagg tgacactctt ccttctaccc ctgccaaggt ggcccaaacc  11280
aaggaacccc acccccccag gctgttgtgt ctgggattta tttgtaacta gacaggcgcc  11340
agcaatctgt tcctagcctg tcctgtgcct ctgcagcctg ggccacagcc tgggccgcag  11400
cctgcgatgt gctgtctggc tcctctctga ggactgaggt agctatccac agctgggggc  11460
caggctgcag gcccatctcg ccaagtggcc acgtggcagg tccgtgaacc tcttggggga  11520
atcttctctt tggaagtggg gtacctctag gccatactca gcacaaatcc tctaggattc  11580
tgctgttttc cctgaaattc aggaagttca tagaagctgg agttcaccag agtcaggtcc  11640
tgagtatgga ggcttcaagg aggctcacat ccagacacag aatggggagc tgcgagagcc  11700
aaccctgtgg accctagagg ctctgcccta accctgaagg gacatggtct ggacttacac  11760
aaaaagagga aaccatgtca acagcgtgtg tgtgtgtgtg tgtgtgtgtg tgtgtgtgtg  11820
tgtgtgtgtg tgtgtatgtg gaaagtgtat gtgtgtatgg taagtatatg tgtgtgtgat  11880
gtatatgtgg tatgtgtgtg tgtgtatata tatatatata tgtgtgtgtg tgtgtgtgtg  11940
tgtgtgtatg tggtgtgtgt atgtgtgtgt gatacgtgtg tatgtggtaa gtatatatgt  12000
gtgtggtatg tgtatggtgt ttatgtgggt gtgtgtggtg tggtatgtat gtatgtgtga  12060
ggggtttgtg tattacgtgg gtggtgtgta tgaggtatgt atatgtgtgt gtgatgtgta  12120
tgtggtatga gtgtggtgtg tattggggag tgtatatgta tgtggtgtgg tatgtatgtg  12180
tgttaatgca gacattaata ttggttgact tcctctgttg ctcttcttcc cttcagagct  12240
gacactcact gttatggtta gactggttga ctagcgagcg cctgggtctg tctgcttctg  12300
ccccagtgct ggggttacag gctccatgac gtgcttccac ggccagcttt tttttggggg  12360
ggggggttcc agtgggtctt ggtgcttcta cagcaagtgt cttgcctact gagccacctc  12420
ctccatccct acttggagct ctttctgcct gtgtactttc actcctgggg tgacttcatg  12480
cttgtgagct agccagagtg gcctttgtat tggctgccgg tgaaaggctg tctgtctcct  12540
ccagtggcca gcctcacctg tgtacatccc tggtaaggac tgatccagct ggtcctagag  12600
ccatcatggt ttgcactgtc agctggttcc agcctcggcc ctgggtaagt cccttgaacg  12660
tgaaccccag actgtcccat gtagggatta agtaatgcct atctcgtgga aagcaccaga  12720
aacagtgtgg tcccatgagt atacaccatg ggttggaggt cacacgtgtg gacttcagtc  12780
atgagtccac tttttgcctt tccttctttc tcggtggcct gggtctttcc tgcccctaag  12840
ttctgtgctg acttctctct ccaaaaacct aggcctgaac ccttgttgct gctagagaac  12900
cagactatgt tgcaagctcc tcctcaaccc ccgggtctca gccccaccct aagacccagg  12960
aagctgccct ttcttgtgac ttaactggta aagctatggc cctcccttgg gagagtttca  13020
cagaccagta tttgagccac tatgggcagc aattgaactg cagccccagc tcctaagtag  13080
ccctgcctag cagtctcagc ttagctcatg gcccagtcgg gagcccaggt gtgaaaatcc  13140
ttctcagggc ttcaactcac tagtgaggcc aagtccaacc ttcgacactt tgtatctgag  13200
caactctggg caaattgcct aatctctctg ggaagtccag ccatcaggag tggaacctgt  13260
catgaactac ctctgggtga cagtgggatc tcttatagaa gcagaagcaa caggaacaag  13320
ccttgacatc ttttaaacct gtttttatcc tgtgcctgag agagagtgcc tgcctcccgt  13380
accactgttg aatggggtgg gaggagccag gaagccccca gaaagagtct ttagtactcc  13440
```

```
aaatccttgt ggccctggct ggaacttact ggcccagttt agagggagtc cttccaggaa  13500
ccttgttaag aaatgagtgc agagcctcag ggacccacag agggtggtgt gcagaggagg  13560
ttacacgtct ggccctaact ctggatgtgc ccaggaaggg aaggacactg ggcccttaga  13620
gaggacactg gcctgtgata cagagtgtga caggcagggc tgaagggctg cctcacctcc  13680
gtcctctgtc ccctgcccgg cctcagcatt ctatccttgg gaatggggaa ggttgaagag  13740
agaggcccaa gttgttcttt cgtgcactgc tgaaggcctc tatgcctggc ctcagagaga  13800
tgtccctatg aaagtcccga gcaagctttg gcccttgggt ggtgaagcag cctctggcca  13860
gcacatatag gaatctctca gcagccaggg gtagggtcta acacctcctg aaacagaaaa  13920
ctcgctgact gcccactact ctctctgcca agacggtgtt ttcagtcagt cccccgcccc  13980
tgcctgcctt ctgcgtctag ccgatttagg agcctctgct tccagaggct gctcccacct  14040
gtctcaagcc ctgtctggat cccttcctct ccaccctacc attgccccag tgcagggagg  14100
ctcaccctac ttgaaggtct ccagctcttt gacctcagtg aggggcccac aggccgcaca  14160
tcctcagatg ccgttggcat gcctgcctcc tgtaacgtga ctgacttcct gaggacagat  14220
gtgccttgtc tggaggccaa ggtgacatcc tacagaaggt ttagcttcct gggtagcagt  14280
gcccaggtct gtgacagcca tggtacagtt atgtgagtgt ggcgctccag ctggaaatct  14340
ccattccctg catcctcatt tgttgtggta ccccagattc ttccccccaa cgtctgccac  14400
ctgtcagttc atgtccgccc ccagtacact caccctccca gactccatgg aagtaatgtc  14460
cttgaattcg gtcttctgcc tcctatctaa cctctgcttt gcaggggcac tctgaaaggg  14520
acaaggctgt cctcttcctt gcctgcctta gagatggcag cctcctcaga ggatgttcag  14580
agccagttgc aacttaccat gcacctgcct cctctgtggc ctcaggtctc catcctgccc  14640
caacccccag gcctgtgctc cagccatctc cctgtgaaaa gctcttccct ctcgcccatg  14700
aagtccatcc ctgctttact ggtagaccca ccgtttccag ggtgctcctc tgacacactt  14760
ctcgccttgc aggtttctct ccattcctgt ccttgttgct ctatgatggt ctaataataa  14820
tctatggttc acagtgtgta tgtgacccgt gggagcaggg gcaggggaag gcctgtggtg  14880
gaagagagaa tcagggtgag tggagggtga ccctgggccg tgcatgtacc ctgtgctgtc  14940
tacctcctgc agtctgtctg ctctcttggc acttgaagtt aggcttagga ttactgagag  15000
ttccagggaa gcgtgaagaa gactagagcc ctgtgtttct ccctccaatg ttccctgagt  15060
ttggttatgt ggccctaccc cagggctact ggctcctgtt ctatgtgtta tctcctcaga  15120
acctcagcct ctgccactga cctcctccct atatgttgtg gtagaggacc catgaccttc  15180
ccctatatgt tgtgatggag gacccatgac cttcccctat atgttgtgat ggaggaccca  15240
tgaccttccc tatatgttgt gatggaggac ccatggcctt cccctatatg ttgtggctgg  15300
gtcagaccag agtttcctct gcacagggac tctcacagga gggaccagcc agcaggctgc  15360
ttgcttttcc agtgaaaatt atgtttgcct gttgcttgtc actgccaagt gccaccctac  15420
acaagggtga ctcactcatt ctggtctgct cagaaccgtc tcagggttaa aaataaacgt  15480
ctcgcatctc aggaagcaag cccccactcc tctggacact ggaccagcct tcccgcaccc  15540
ccacaagtcc tgactgctgc tccccactcc tggagcccaa tagcaggggt tccccaggta  15600
cttgggaagc cagttggtca tggctcactt gaaaaccaaa ttgctgctct ctactccaca  15660
ttttggagag tgcagagagg ctaagagcct agtgggaagt taggcatggt tgggcatcct  15720
gggtgctgtg taggggacca ggactcccag gtactgatac acagtctgcc tccagcacag  15780
catatgatgg ctatttggtt tcttcaccct taccctgctc acctctcaaa attatgggga  15840
```

```
gactctgtag ccctgaatgg tctacctgtg atcttcttgc tatgggtact ctgcaggaca  15900
tttatccatc aaatcctgct gtggcctcat gactcccagg ggaaggcagc actgaaaccc  15960
tagacaatgc caaacaaaga cacaggccat ctgtctccta tgaagcttca cagtggaaca  16020
aaagcccttt ccatgtgtgg tcttgaagct catgacagcc cttggggctg gtaagaaatt  16080
ataataccca ttatacagat gggaacactg agctctcgat ctcagcatct cttgatggct  16140
agggagaagg gaagacaaga gggtggctat gctatggcca tggtgcctgt caggggtgtt  16200
gccgagtagc ctgtcctcac cctttctgca taccttctct gtcaatgtcc tcatctgtag  16260
ggaccatgga gacagatgga agatgagggg gaagtacagg aggaatggag aggggacggg  16320
agcgctggga aggcagggag aggggagggg gtccacacag cattgccact gacttcctct  16380
ttggttctca cagtttgtct gcaccgattc atgacagatg gagggagggg agagctggtg  16440
ccaagaggct gtcaccacag gcgagcagag ctggggggag ggtgctttgt gtccatggtt  16500
tgtgtaggga ggggaagcag ctggtggtct ggctgcctgg cctcctcaga gcctgttccc  16560
caggaacttg gggtgggtt acgcgtggat gttgtggggc aggagagtgg gcaaagggtg  16620
agcctgccat ctgccttgac aggctgtgat cctggccctc cccaccaagg acagatgtag  16680
ctttcttcac tgggtgctgg gagtgggcag gggctctgg ggactggcac tgagctgtgg  16740
tcaaggaaga gcctgagact ggaggccttt ggatcacaga gagcacgggg caggggtggg  16800
gggagcaagc aggatgcctt ctgggccagc actcatccct aggtgtgcca tctggatttt  16860
accatgctgc cttcctgccc ttgtattcct tctagaccct gacacattcc aagagtggat  16920
agtcctgacc tgggcttgat ctgattcctt tgttgtgtct tgtttcttta gggtggtttc  16980
aacaagcaag aatggctctc tcccaccccc agtggacaca gtggccagga gatacttgtt  17040
agctaggtgg gtgggtaggt gggttagcta ggtgggttag taggtgggtt agctaggtgg  17100
gtgggtaggt ggatgaattc ttagcttgca gagcttctga ggtgagcctt gctccttcgt  17160
tatgcagtcc tgagctctca gaatgttctt tctgtttgtc ctgaggcctc aggcagccca  17220
ggcttccttg gggtccacca aggcctctgg ctggtcttcc tgacttagag catttctgtg  17280
aacactgaga ctcccctgag tcttcccagt ttcttagtga ccccttgtag ggttgggtcc  17340
ccaagctgtg gtctctatta agcccttagc ttgtattggg tctcacctat tcgattctca  17400
cgtgcgcctt ttcagctcac gctgccttta tcccttcttc acagaggagg tgagtgaggt  17460
agaaagtaat gagtgattta cttgggtgtg gtgtgcattc agaaggtaag gggctgggcc  17520
tcctggagca ggggttgggt gtgctggggc ttgttggggg cccctggcct aataaggctc  17580
tggactctgt ctatcctcta gctcattccc gagcaggtct ctagcaccaa gttccagctg  17640
tgtactttca catctggaac tgaggaccta gggctcaggg cccctcctgt ctctgaagcc  17700
agtgtgtggt taggccagtg tgtggttagt ccactttggg atggaaccca aggtccttaa  17760
actgataggt gatttgtctg aaataaccaa agatgtatgc agggctaagg ccctggtctc  17820
ctaggcatct tctcattaat atatattttt aaaggtttat tgtatttatg agttacactg  17880
tagctgtctt cagacacacc agaagagggc atcggatctc attacagatg gttgtgagtc  17940
accatgtggt tgctgggaat ggagctcagg acctctagga gagcaatcag tgctcttaat  18000
cactgaacca tctctccagc cccgtcgtta ttattaataa tgacagtcat taatggtaaa  18060
ttacagtgca tctgcctcga gccagctcag ctggacagct gaggggagtg gaagatagtg  18120
tgcatcctga gtgagggaca tgcttgttcc tggacttgca ggcactgttg tctgctcccc  18180
```

```
acagcctgac tgacactggc tgagtactct gggtaccgct gcggcagctt ggttcagcct  18240
cagtggctga gaaacaggct ccggggctgc cctagtggaa tgcccactaa cccttcttcc  18300
ttccatgtct tttaccaagt cattccacaa acactgttgc taggtctaga cacaacccaa  18360
gacagcccca gggcctaacc tttcccccca aaactgtggc tctttggatt cttggaggtg  18420
ttcttttcag tgagtgttat ggatggcccc ggcgcttcac tctgccatac tgtgacccac  18480
tgtaccatag tcagtcacat agcatgggag ttgactgggt cagcttcccc cttagggtca  18540
gggtgtcctg tctgcgcagg gccatagtgg tcacttcctc agaggactga gaactgatgg  18600
gcacagtgga caggggctac ttagtggcct tactctatgc ggcacccaaa ggtggggaaa  18660
ctcacctaag gtcatagggc atatgaaagg acagaggatt gggggcctgg cgtctggctc  18720
tcagggctgt gtgacagcac tgttggaaat ggatactcaa ggtgtctgac atcctggact  18780
tctctctctc tctctctctt tgcctctctc tctgccttca agaccccaat ctcctcccta  18840
atcctgtgtt agagacagtc ttcattttgc ctatcagtat ccctgaggcc cctggggagc  18900
ctctcacctc ccacatgagc aggagagagg cgagagctag caggggcttg ggtacaggat  18960
ctaggggttt ccccactcag gttgagatct gtcacaacat tcatgttaat taagccttgt  19020
tattcagccc tgcacttacg cagagttcct gacagcagat tactcataag tgaggcggta  19080
aatttactac gtgtttccca aagtctcaga agcaaaggcc gcgttgggaa aggtttgtag  19140
ggtgaacgat gctcttcccc actcacccgt accctcctcc atcctcatgg cctgtgcagt  19200
ggtggtggtg gtgtgtgtgc acacgtgcac gtgagtgtgg agggtgagga gtcggctccc  19260
tggaagattc aggtcacctg actgcttcca gctgactgcc tcactggagt gcaggagccc  19320
agggcacgga gcttggcagc ccctctgctc agtgcctcag ctctgcctca cccctggctc  19380
acagcagact gccatgcaca gacacatccc cttcagagtc ctcccacgga ggcacgcagg  19440
ctctatgcgc agtaggactc agcaaagaca gccttggatc tgcctctaag cctgcagtcc  19500
acctcggtgt tggtgaacac atttcaagtt gctgtgcaat ctaagggacc tctgctgcgc  19560
cccccccccc cccccccgca gcagaaacag agccccctcc cccccatcag gtgaagatcc  19620
aggaatgtta cagtgtaatc tttcctcagc ttgagttgta gcagcagatg gcccttgcct  19680
gcttcttggc aaggtaaggg gtggggcccc tgttaggtgc atcccctcac cctaagtcct  19740
gctgcctccc ttggcctatg gctgggccat gcctgagaca tttggaacaa atccaggtct  19800
tgggtgccta ggattttttt ttaattaatt agagcattaa atggtagccc aatgggagaa  19860
tcccaccatc tggctgtcac aggagaggca ggcaaatctc tgcatatttg tctgtagtgt  19920
gtgagcatca caggaagcca cctgtgcgtg tgtgggtatg cagcccgtgt gctgcagtgt  19980
gtacacagtg tggcttggtg tgtgtggggc acacatgcga gtataagcgg ctgagtgtat  20040
ctctgcgcat gcatgctcat ctgcatgtgt gtgcactgcc atgcccgagg acctccatgt  20100
ctatttcaac atacttccct gtgtgtggtc taggtccagg cctggctgga gagcaacatg  20160
agacaggctg ggctgtgtgc ccagcggcct cttgagcctt cctggcagag gtagtgatca  20220
cagactgtct gggcagaagg caagatggag ctaggtttgg caggtatgca ctggcattgg  20280
gaaggaggca ggaatccttg tgctgtgttt gacagatggg gaaacccagg ccgatccaag  20340
cacagagcca ggatggaggg acaggactgg agcccagtct ctggactccc tgtagtggtt  20400
ttatctgttc ccccaggcta ttgccctgtc cggtaattta tgccttaggc atcttttatg  20460
ctgttagagt ttcacggtgg ctcagagagg ctcttgaaag agtactcctc tttatttcac  20520
aggactgacc aggatcaagc tctgaattcc cactgtagcc ccttccttag aggaagtacc  20580
```

```
ctgagctgct ggagagcact ggacctagta ggtctactca ttcgttgtgt gatgtaggcc  20640
atcttgtccc tctctgaact tcaggagagc tgtaagaact aagtaatgac tggacaggtt  20700
gctcgttaga agagtgctaa cctagcatgc gcgaggccca gggttcaatc cctagcactg  20760
catgatatca ggcatgatag caaaagtagg aggagggtca gaagttcatg accgtccttg  20820
gctacacagt gagcttaagg ccagcctgag cgacagagtg atctactacc ctgtctccaa  20880
aataaatgga tagatgatag atagatagtg tcgttcagtt ttagagcatg cgtgaggcct  20940
taggttcatt tctcagcacc aagtcaagcg aggatctata tgtaataggc tttgtatacc  21000
ttaaggagca gtgtggtggc catcactcca tggtcagggc caagtctcac attcctcatc  21060
taagagtaca ttatatatac caggcaagta gcctgcatga ggtcacatag gggcagaggc  21120
aggatttaag ctctgggacc tctaacctgc tcctggcagg aggaagacca cagcaggcag  21180
tagacgagac tctcccaaac gtccatgccc agaggaactg gctacttgga ggggagtgaa  21240
tttgttctgt agtgcaagca atgattgcat gataggtggc ttcacctcca tgcaagccat  21300
agaggggtgg tttactgggg agcaggctgg ctcaaggcag ttggtatctt tagcttgtat  21360
aaggagcgag agttgtgaga tgtggtccag aggcctgtga gcagggaggc tgccccccgcc  21420
gcttcccctc cccctcccc ctcccccaga agtcttccct aacttcagag ttcaccagta  21480
cctggcaggt gcctggcaca cagtaagcac ccccttctg ctcctgattc tcttggcttc  21540
cagcagtaca gacctgagac tctcctacga gtaggatgag tgaaactggt ccttgtgtga  21600
gttaggtctg gttcttcctc ccagccccgt gctctcagaa ataagatcca gactcaaagt  21660
ataaattggc catatagcta ggctcttctc tgactagatc ataactgtaa taatccattc  21720
tgccacatgg ctgcttacct gggctcaggc accaagtgtc cccctcgtca catcttcccc  21780
tgtgaatctt cccgtgcctg gctctatccc agaattcttt ctgcctcccg gatgtcccac  21840
cttctcttct accctttcct ataggccata ggtttttaaa ttgacaggtg atgcatccat  21900
gcaatacacc agatgttctc tctgcagccc ctcccgtatg ctacacctag cactgaaggt  21960
gccgtagagg gaaggacaag gggaggccta gcagcctctg cacccagccc tccctgagtg  22020
aacctgggga tccctctacc ctaagcactt gccaagcaga tcagtggctg cacgtgggct  22080
tgcctctcct ctcccacccc cgctttggca tcgctgtctc caaggtaacg gggaattttc  22140
cctccctctc atcattaggg tgccagggca aacaaacagc cctaatccag atgagccttg  22200
ggccacaatc acactcttct ggggttttct ttttatttct agcgatttg agaagcttgg  22260
agtaattggt attccgcaca ggttaacagg ggcactgcct ccgcagtatt atgccttaat  22320
tttctttatc acatagcaag ttggaatgaa tcaccccgct cctgcctttt tcccaccgaa  22380
acctattacc agcctgtctg ctggttaaag tcatttcgtg gcagcgcttg gcttcttgcc  22440
actgccctgg gaatctttct gaccagagcc aaagaacaag gagggtgaag aatccatttg  22500
tacaaagcgg gggtctcccg ttgagaactt acttccctcc ctgttcagaa gggacagctt  22560
tcagcctctt gcctgcgcag actggccata tgtcagcggt gggaacggga ttcctgggcc  22620
tgcggtgggg gaggggtggc catgcctact gctcctggca cctgggttag atcccatgac  22680
gagagtttct gggcttctgc agcttgcttg tgagagtctt tgatggccga gtgtcccacg  22740
ttctgaccca gagggcctga gcagtctagc ttggggtttt gagactctaa aatgtttatt  22800
ttggaacatg gagagttgaa tctgtggttc tgtggctcct ttttgattct gagatagata  22860
gaaagataga tggatggatg gataaatgga tggattatag atacatacat acatacatac  22920
```

```
atacatacat acatgcatac tgtgcttaca cagggtctat cattgaatgt taaatacatt  22980
tggctaggct ggctggccag taagctcttg ggttctattg tcttccctta ccctcctagg  23040
gttatacgtg gcttgttttt ttaatatgtg ttctagggga gcagaatcag gccgttctgc  23100
ttacgcagca ggcgctttat cagccgagcc acctcccagt gctcttgcct gatctcttca  23160
gctgctctta gttctgtcgt gttgggtcct gtgagggagg aattgctttg ctaagcttac  23220
cttagaaatg tcacctcagg ttggccccag cttctctggc atcgtctctc cgttcataaa  23280
gttgaggact gagccaggtt gcctccaagg cccaagttcc aggtttgtcc tgcctgcctg  23340
tcgtgccctg cgtggcctgg tctctgtcta gcacttcatg ggacctgagc cacacatgtc  23400
tcctgtccat ctgagccctc agccattcca gaaggaaggc tgcccagccc tccctggagt  23460
cccagaagga aggcattgat ggtgcctcaa agtcgcttcg ccccaaaatg ttagccctgt  23520
gttctaggtc aggaaaccga gggactgaga gatgaattca tccatcatgg tacagcttcc  23580
tcctgggacc ttgtctgtgt caccaaggct gcacagctgt ggctggagtc tcactaaaca  23640
caagagattt gggtgagaga gagagcaaga aagggggga gcacgagaga gcacgagaga  23700
gcactcacgc tctatcacca cccctttctc tgaggtccaa ctaaaggctt cctctttagg  23760
cagccctccc tccctggctc ggtgtccatg ccctaaagct ggccagagag ggcaagtgag  23820
tgtcctcttc cacctttgca tctttggggt gaggggatgg ggcagtttta ctatctctgg  23880
ctggccttga aatccaccca cctctgactc ctaagggctg tgatgaagga tgcatgcccc  23940
tatgcccagc ctaccccctt gcctctaatt aagacccttg tcttgtccca ttcttgatta  24000
cggactttgc tctggggagg tccttgttac ctcagcttag tacagactgg gtaggaacgt  24060
ctgccttgat gtgttccttt gagctcagct gacttttccc cctcatctct gtgtcccctt  24120
tggtccccac ctctgagcca agctcctcag ttgtccctgc attcagggcc catcgctcca  24180
tcccttgggc atctacctga accctggact cagctgacct tgccacccta acagacactt  24240
gccctccctt ctggaagttg gacatgctgg cccacagctg gagaactccc catctgtccc  24300
cttcactttc acctgtaggc acctggagca agcccttaaa ttgggctcat gggcaaactg  24360
tgcattttct cttttgatga ctacaggagg aggagactga actacagggg gtaagggacc  24420
tatccagtgt accaccccgc ccagaagcca gaggccacct ggagtagtgc ccaggtttgc  24480
ctcagcccag gcctggctct gtggacctct ccagtccgca gagcttttcc actgcactgg  24540
acagctgagg gtgtgcttct ctggttccag ctggggaagg tggtgagcca tgtgtgtatc  24600
gccgtgtgct gagcctctag gatggcttac tcagcctggt cctgtctggt agaggctcct  24660
tagtctttcc agcgtggaag ctgtacactg cgaggcatac ctctgtgtgg tgctgataga  24720
tggtgagctg tgtggaactg catgaccggg cttccactgt tccccttgga gctggcctat  24780
gcacactgct ggggctgggg gtgggggtgg gaaaagcacc ccctgagggg tggcactcca  24840
gcagggatcc tctgggtttt tgctttgtca ggtgagggca ctgccagcca ccagcacagt  24900
ggtacccaag ccctccatcc ttcactcctt tgcacccggg agtccttggg cttctatggc  24960
ctggcttcct tgccactgga tgccgagttc tgttctggga actctggcct ttccattggc  25020
agttgatggg gccttaagcc taaagaaacc tgtgcaggga ccctcagtat attggcagtg  25080
gggctagaat gcaatctaga accttctaaa ctgtggcaga gctgcctctc ctcctgtcag  25140
aaggcctgtg gcaggaagag caggttcctg aatgtaaggg acctggcagg cttggtgtgt  25200
gtgtttgtgt gtgtgtgtgt gtgtgtgtgt gtgtgtgtgt gtgtgtaata gagagagaga  25260
cagagacaga cagacagaga gggagacaga gggacagaga gcgacacaga gacagacaga  25320
```

```
cagacagaca gacagacaga cagacagaga accacagact acagacccct tagagctttc  25380
gggtggcctg tctgggctta ggtaggaagg tttctggtca gaagacactg aaacaagtca  25440
ggtaacctct gccccagtgg cagttgtgaa gttggaatca cgtaggaccc tgggctagaa  25500
tccctgatct aaaaggattt cccaaccgtg cctcctgcac ccaagaagct tcgacttcgg  25560
ggatgccctg agtttgtttc ctgggaccta caattctagt gccaggtggg cagtccacat  25620
tccaggacgg ggctgatctg atccttaaag gacggtgttc atggggtgtg cacccgtgtc  25680
tgcaagcaac attgggtttg gctacttggc aggcaccagc ctaagaccct tacagatccc  25740
atcccatccc atccatgtct ccctctgtac cctcccccac ccccagctgt cactggctca  25800
atactgcctg cttctacaaa tcactgggac aggaagatgc ctttgtcgtc tcactcagag  25860
ctgctcatct ttcctgtggc gactgggagt cccacatacc ccagtgagag cctggacttc  25920
ccttggtgac agccagaccg gggtcagaga gtatccaaca ccaactgggc tgtgctggat  25980
ctggaaggag gtgcctgttg tgggaagccc cgagtgaccc ttttgaaggg ccttggagca  26040
caccagagat cacagcctat gtgtctcaga gccactgtct agaacatcag ctggagggag  26100
tccttagagg ttggttcaga tgaggaaact aagacccaga gtgtggaaga ggccactttg  26160
gaagttagga atgtggggct agagatggtc tctgagggag agcctaggtt gaggacactg  26220
gggaaggacc taggtcaggg agagagaggt atggcttatg acttacttag atgctgcggg  26280
ctgtgatgtt ctctctctct ctctctctct ctctctctct ctctctctct ctctctctct  26340
ctctcctctc tcttcccccc tcctctctct cagactctct cctgtcatct ggtaatggta  26400
ccttcctcta aggtccccag ctgaggatgg caggaaaacc cagctcttca ctgggagatg  26460
gtagtcgcac tggatgctca tggagtccca ctgatgacat ctgccacagc gataggtcac  26520
cacgtgatcc tgatgcccca ggccctgctc caccatcccc attagtgttc ctgcagatgt  26580
ctcccacatg gcctctggat ggcctcctgg ccccttccta tgggtgtttg gggacatttt  26640
gtttgactcc tgatgtgccc tcgataggat atgtagtgaa cagagaagga aacaactggg  26700
aagactcaag gggaacattt actaacttaa tagcaaacag gactttgctt tagggatccg  26760
gccatgagag gatctcggca cgggtctctt gcctcctcag cagctgtgga gtcttcctca  26820
ttctctgcag gtgggaggag aaaggactca gctatgtctg tgaatgtcac ctgccgatgg  26880
atagaggtgg cctaagtcgt ggagccgggt aggcagcgct gagccaaggg cctgagccct  26940
tcgagctact cttgaagtat ttcagggctt agcagccgtc tgctgcccaa caccaccaag  27000
agcctggagt tacggattgt cagagtatgg ctgcctggac ccacggaaac atccctcgcg  27060
gggatgcggc tgtgctgtct acttctgaca tctctgactg gccacgtctg ttagagagac  27120
ctagactgtg taggggctca gggtgggagg cactacaact aggaatcctt agagacttgg  27180
tgcctgagac aggaaggctg ttttaaatgt cagacccaca ggatctttaa actcagggct  27240
tatgggaaca tcacatgcct ggagaagggt aaggatttga acccagagct gctggaccac  27300
agcgggttcc agttcccaga gtttcatgaa ggtttctgca gggctgttga ggggaaacag  27360
ctgatgggat cccccactcc ttgccccatt tccacagcac agatccattt ttatctgttt  27420
tctgtgtgta gtttcacttg ggaaaaggtt cctcctaagt gtgaaaaata acctttgtca  27480
ggccttgtac caagctgcag ctccatgcca ggacccgcca cagcctgggg aggagggggg  27540
gtgtctctgg cagtgggtgg acaagcctgc agtccagggc ctcctggaag ggggtgcagg  27600
ctgcttcagg ccaccgtctc ctcccccccct cactcctgct gtattgttgc tgcagtcgga  27660
```

-continued

```
gaccactctc agtctgtcgt cctgttgact ggggtgacag tttaatagta gcttcctggg  27720
ctgtcattta aatctgcctg ccaggttagt aggccagggg cgggctggca cgccccctgc  27780
ccccaccccg gatcttcatt ctgctggcag cagttgtctt ggcaacctca gggcctggcg  27840
agctctgcag aagggtaaca gtgtagggag cagccctttc atctccccga acagggtaca  27900
agtgcccagc tgccttaggg ctggctgcgg gctgagccag gcctcccggt gctggcctgg  27960
gcctgagaga ggaagtggaa gcagctgagt ggatccctct gggcagggac ccaccccagg  28020
tcactcggtc ggtcggtcgg tcgcagtgct gagctggact ccacctttct tactggtctc  28080
ttgctctgct tctgtctgga gctcagtttg catccctgac atctctctgg cccaggtgac  28140
tggcctcagt cccctctccc tgtcctgagc cctccctcaa acagtccctg atgtgaggat  28200
ttgagtgtcc tcattgctga gtgctctttg gacacctgtt ctgcatggtc tgtaggagag  28260
gtccacagtg agatggctgg gtaccattct ctgctaggtg cctgtgtggc caggctctcc  28320
ttctaagaac ctcagcttcc cataggatca agagcttgta tcacatagtg cttcctgata  28380
tggctcactg gacttccttt tcttgggaaa ttaatagaca tggcatccaa aagtggggat  28440
cttcattaaa caagattgga tgtgctggaa gaaacagcca gtcaggtatc tgctgcaggc  28500
ttttctgggg gtggggtagc ttttgttatg ctggtgacat ctcgattctc taagggggaa  28560
agtatatccc aaagacctga gcagatggct gcccaggctc tgtgcctgac ttcctctgct  28620
agcagctgtt ggtccatgtt gtgtagcctt accaaatccc aacgcaaaca tagccatggg  28680
tctcactggc tgctgaataa gccatcctgt ggttagccac accctcagtg ggtccctggg  28740
tgagctcaag gaaaacaagg tcacactggg cctcctaggg acagtttgat gctaggcaga  28800
gcaagctggc tgctagcctg gtagagctct caggctcctt gatgcttgct gcctccctag  28860
tcccttacaa actctgtggg ttcctccagt ccaggcctgt tagcccttcc cagaacaccc  28920
ttcatcccaa gcccccatcc tcgcctaggc acctctgctg ggtacagtcc ccctccaggg  28980
gccgttatca ggctgcctgg ccacacagtg gacccagata cttgagctga agtgtagcct  29040
cccacgggca cacgctgtgg ccttgagctg tcacttacct gggaaatgtg tcttggtggg  29100
acattctctc agctccaagg agcagctggc agctggctta tttgaagcca catctctgca  29160
caggagtgtg ggtgggatcc ttggtttgag gatgtgtgtt gtttggggaa ggacgcctct  29220
gggggtgggg cgtgggagtg atgagtgagc atggtaattt gcaggagcat acaggggctg  29280
ggagctgctg aaggaccagt cagcaccata cctccatcgc ctgaggagga ataccacccg  29340
gacgtgcggg cagacaaccg tgcacaccat acgcccttca gttggggcca ggactgtgac  29400
tttatattca gtcacgtccc cttttgtttc tcagttcaca aatccttagc accattctta  29460
gcccatttgt tcctcatagc agccctgtgg gggtttatga ggcccagaga agtagtgcat  29520
cttgaataag gtcacacagc cacaggtggc accagagacc ctgtgaccat gacgcttccc  29580
ttggcttgca ttcttattat acatagcagt agctcccatt ccctttgtcc tggatttccc  29640
actgtcctct gctcttccct ggggtaggcc cctcctcacc accctgtgga atcccagggc  29700
ctttgtggca gtccatctgt tgccatggca ccagattatg atgtcgcaga ccctggatga  29760
ctatgtatca ctcctgcggc gtggagtaca gggactcaca gaggtgggca ttgtccaagg  29820
ggcagactgg cacagaggga cataaatccc tggaaacaga gaaccacagc ctggagccca  29880
gctggggaat tgccctggga accaaagcca aggccaggag agtagggtct ggcctggcct  29940
tcagtgacag cttgaccggc ttggcctctt cctgtggcag ggctgagcta gcttggttac  30000
actggaggga cccgaccgac gctgagcttg ttcactgagc tcttttgcct tttgtcctgt  30060
```

```
ggcagtgcta cacaggaaag tcacatccct actggctcgg agacagaagg gacttgcctt  30120
cagtcaccta gtccaacggg gggacttcaa aggtggttta gtgcagtctc tagcctgaaa  30180
gtggtcatat cacctctgtt tccacagggt ggtgtgttct ccaagcatgg actgtcatca  30240
taggccaggt ctctgcagca cacttccggg cacatggcaa gggtatagct ttgtgcagga  30300
gcctctgtgc ttggtggttg gtttgctacg aggtccctga gagttgaggg gcctctgtca  30360
caggagtcct cgctcctccc ctgccagtca gtgccctcat ggctgcaggt ttgtgggaag  30420
ggatttattt acctctcaca gaccctgaag tccttctgcc gcctacccac tcacgtcttt  30480
gagcctcagt ttcctctgta aacgagattg acagcagttg ccagggtagc tgtgaggggg  30540
ttgtaggatt tggggtgaga ggcccaagtc tagatctggg tgaatatggc cgaaccggcc  30600
cagatactga aacagtctgt cccgcagtct gctgtgggtc agctaagcct gagctgacac  30660
tgctggcatt tggctgctat ggcgtccgtg cccagtgtct gctatggctt ggcatacagg  30720
gagtgagcaa gctctcccct gcactcccag aatgctcaga attaagggtt ctgggatggt  30780
atctggctgt cttgtcttgt gcccagtgac agggatggta tctggctgtc ttgtgcccag  30840
tgacagtgtt cctgcatcac cttaagcaat tcatcttgct ccttggcaag cttgtcccct  30900
tgctggagct ccttggcgta gctgtcctac tctgcgttcc caggagcacg ggcctagctg  30960
tcctactctt gtgttcccag gagcacggga ctattggata ctggggctct cataggatcc  31020
tccaggtatt tgaggggctt ttccgccgcc atgtgcgtca gccactgttg gaggactgtg  31080
ctggcggaaa cctgctgaac ctgacaggtt caaatctgtt ctcacttcca tgtgacctta  31140
gacatataac ttaagagcgc gagcgctgcc tggaactctg cctgtgttat atgatgaaat  31200
gttaggctgt ctgtcctggg atttcctgag taaaataccc agcagcatca agggagccgg  31260
aaaaaataag aaacggaggc atctgtctta ggaagatgtg aagaaatctc agaatagaga  31320
tggccaaagg atactatgga aaagcaaagc aggcatggac cagagtcaag acgacagtca  31380
gtgttcccaa aactctgctc ggcagctgga ggaccacaag aaggggaaaa agtacaaaca  31440
aaagccagca aaccctcagg ccatggactg tgtttaccca ggggaggggc cctaccctgg  31500
atgtgtacga gcagagatgc caggcaggga ttggtgtcct cctgtggtct gccccgcgtt  31560
gggtcctgtg tggaatctga catggttcct tgtggaaaga cgggagaaaa gccagccaca  31620
ccagaccaca ggatccacag tgatgtaaag cagcaggcat cagatttaag ggctcaggcc  31680
caaactagcc tattgctggt ctttggaaac agccttctac tgcaacacag ccctgtgcac  31740
ccacctacta ttctgtcagg gctctgtcca catggcaaaa cccgaggagc agggcagagc  31800
ccattgcagc cgaaagcccc aaatgtctat catctgtgac aagtttgcca agctgtagaa  31860
gaccgttgag aggattgtgg cagctcaggg gaggcccccg acagagactg gaggtgatgg  31920
gaaagaacat ccaagcttgt aagggaaaag cagtgtaagg attttcagat gacagacttg  31980
gcagaggggg actattaata gtacgtaggg accaacagta gtcatggtgg ggccatttgg  32040
gaagctggaa aggggaggaa gaggaggaag actttctagc tgctagagag gggtcgtatc  32100
cagatggccc caatatcaca tctagttcca ctgtcactca gggagaggac acccagggcc  32160
tgggctcctg aggaccctct tggcctctct ctgccagttc tggggcctct tggcctgtga  32220
ctgtctacca tgcccaaacg attgtgtctt accaaatccc cttccctttc cctaggaaga  32280
ccaaagacct gggagggaaa gtgtcttcct tgagagtaca tggcaaagca gaacagccaa  32340
aatgcacatc caggcctgct agctccctgt tcagggctcc tgccttcttg cccctgttcc  32400
```

```
tgggctctca gtcctagggt agggctcatg ggagctgaat gcaggtgatg ttgaggagtc  32460
cctggagtac atgaagggcg caagaagcca aaagccaagt cctgaacctc tactccacac  32520
ttcccagggt gggcaggccg ccatgctcac ctgcaggttc cctgttggga cagctgcctt  32580
gttctgccct tgtctgatca tatttataat cagtgccagg caccgggaca acacagagaa  32640
ataataaggg ggcgtggcca acttctccac cctgaccctt acatccagtt cctttcagaa  32700
ctaggcacac ggggcagcaa atagtttggg gctggacata gtattcatgt tcttacccct  32760
gctccgctat gagtcatgca atctcagctt gcatgggcac acaacagccc atttctttcc  32820
cttctaatta ctccccagac aaacagcaat agctgtactg acggcaagca cctgccatgc  32880
gccggggccc gattgcacat cctcacacat tagcttcctg ctatctttca gcccttctgc  32940
tctttatagt aagagggaat tcagaggtta gtgatgtcct caaattcacg cagatggcag  33000
gaggcccagc agggttctga aaccctgatg caggacatga gccttccttc ctgcagagtt  33060
ccatgacagg gacccatgct ccatcatggc cacaacttca aggacaaaat cctttattca  33120
tcctgctaca aaaccatcat cttcttttag ggttcgtggt catgagcgct ccctggggct  33180
ttcccagggg tcctgtttgt gcgctgggat ttaagcaggt gaagaggctg aggcctgcct  33240
gcaggaggag tccaggagag ggatgctgtg gtgtggagcc atggtgacag cctggctgtg  33300
cctgagaccc tcggggagct ttggtggtac acttctgagg ctgagcacac gccagttacc  33360
cacctgcctc ctgcctctgt cttagaaaag cattcagtgc tcacccttat gctcttatct  33420
ttgtcccaca gccaagagga cctgcgcgga cagcgacttc acctgtgaca atggccactg  33480
catcccagag cggtggaagt gcgacggcga ggaggagtgt cccgatggct ctgacgaatc  33540
gaaggccacg tgctgtgagt cttgccccac ctcagtttcc tcctcagcac tttgaggttg  33600
ataggttgtt aggctcacag gccatagtca gaggatgctc catgccaggc ccttggggga  33660
gtgggcggct cctggtgagc aggcgatggt ccgtggagct gctctgcctg tttccctggc  33720
cttctcctga gcttccctgt aggttccctc agttcctgca gcaccaggaa ttagagtggt  33780
gcgcagaggt agccctgcct cacctcaggc cccctgctct cacgcttgaa gatctgaatt  33840
gtaattccag cagcactaac ggcagctggt gcgcgctaat catttaccat gggccacacc  33900
tcgattgcta agctctttgt attcctttta tcttcgtagc agcctctaga ggcaggcacc  33960
gccactctct gacttttcaa aaggggcata cagaaactca gagagttagt gtgatttgtc  34020
catggtcacc cagccaagac ttcaagcccc cccccctttt ctggggcctg ttcttcgtgg  34080
ctagctacat gatgacataa ggaaccggga agaggtggcg tggctagtgc ttcgggactg  34140
ccttccacac gcagggcttt gtctctccgt gatttctttt ctaggctcta atcctcaaag  34200
caaacttaga cctggcaggt cattccgtga catttgttaa attaaaaagg agatgcggaa  34260
ggggaggggg aggacccaat ggtccagagg cagagctata gcaaggcaag cctgagacaa  34320
aaggctgtgg ggagcacgtg gaggatggtg tgggactgtg gggagcacgt ggagggtggt  34380
gggactgagg ggagatccag aaaccgctct ctgaggctaa catttgcccc agaggtagag  34440
gcagggacaa tggaggccag agtcccattt agggctgcca ctgatgataa ctgggttttc  34500
ctgtctccta gcaacaaagc taccagtttc caagagagcg agagagagag agagagagag  34560
agagagagag agagagagag agagagaccc ctgccccaga caaagggccc ctcatttcct  34620
aggcggctgc caagcccttc ccagttttac tgcaggccca tcctttcctt accacaccaa  34680
atgccactcc atgctgtcct gggaggcctg gaggcagaag gaagccctgc actctctcct  34740
gcccttccaa aagaagagag ccttgatgca cttgcctgta ctaccattgt cctgccagcc  34800
```

```
tggagcacgc aagggtgctg catctctccc agagaaaaac acactggacc aggtttggcc  34860
tcttggccag ggctgctcag ccgagaaggg acagagtcct gtgcctcctg gagagtttct  34920
ggggttgggg tggaccttcc taccctaata gtcagccagt tctgccttgt gatcctggat  34980
gtgggtagag gctttatgga ggtcactggg ggagggcagt cttgctgccc aagggctatg  35040
ctcccttctc tctacatctc tgtttagggg tattgcctcc tccccgccct gtccggccct  35100
ctcacctgtc ccgctcttct gggctctgca tccctactgg ctcatgctcc ctgccccctc  35160
ttaccgcccc tctctcctag cctgcctgtt tccttgtctt tctacctcag aatgccagtg  35220
ctcactgcct tctgacctgc gatggaccca cacaccccac tcctgacttc cagggccctg  35280
agagttgaca gctgagcagc ctttagaact tgatagacct gcagacacgc agcctgtttg  35340
tggcaagtgt ctcttccgtg acaaaaggca gtcttctcaa gctctctgag attcatggga  35400
gcagcaccta ggatcgaaga ggcccagctt cctgtgggtt accccaggca attcctgtga  35460
ggtcctgtat ccactgccac ccctcattat ataatgtatc caaatctaga atcccaaaga  35520
tttccccatt ttaagattcc taaattctta gtagttcaag accctgtttt tgcccttgtc  35580
tagtggggca cagagtctgg gatccctacc ttacgaaccg tcacaatggt cctggggtct  35640
tagagtaggg agggctgcct ggaagaatcg ccctgagagg gccttgaagg ccaggcagaa  35700
tttgtggcag ctggacttgg tagcaagctt gctctcagct tcccaactga atgaaaaccc  35760
agcagccaac ccgctgtcca tttaattggt gttgccatag caactaccac agcctaccag  35820
gtttctggga ctgtgccagc tcccaggata gagccttact cctcacccct aacagaaaga  35880
ttatagatag aagggcacag tgggcttggg atctggtgca gttggaccgg gttgtttgcc  35940
ttgtatcctc atataagctg tgtagccttc ctgggcctca gtttccccat gttcagtgag  36000
aaagaataaa tattggagta agagccagca ttgtctgttt tcatgcttgg gcctcaaact  36060
ctctgccccc aacataacag tccattagac taccaggaca ctagatccat actattaaaa  36120
tattgtaagg ggggttgtga gaagcggagg gacctgggag caggttctca tcaaacacag  36180
agtcataatg ggaaagccca gaacatttgc ctaatgaaag tatcgtttgg gctctaatta  36240
tagctcgctt gattggggag cctctgaccc accttcaggc atctgtcggg aggggtgcag  36300
gcagggagca gagagactgg ttcaagagaa tgagttacag atctgggtgc tacttgctac  36360
gtgtggattt ttttttcttt cttagcagct agccggggcc tttgctcctt accccctgctt  36420
gccttcaaat tagatcagga agcaccggcc tggagatgtg acatcaccca ttttgcctga  36480
tgctgtgtgg aggagcctgg tatagttctg ctccttcagg gtgcaagggt gcaaaggtgt  36540
acctcctaag gcattttctt ggggttccca gccaagcgac agtagtgctt ccctacggcc  36600
caagtctcca gtctccttag agcaggctgt ccccatttgg acgttgtcta tccgtaagac  36660
tcgagtcttt aagactgtag accggcgagt agccatcagg tactggcaac aaacattgtt  36720
ctttttcttt aatttattaa cttatgagtt ggcaaaggat ttctggaaca gggttctcag  36780
gaaattaata aatgccttca gtcacttcag ggtggcactt caaccccccct cacagtgttg  36840
tctggcagta gggacttttg cttcagcctc ttagaagctg aaacacttgg gcagcaagcc  36900
gagggtgtcc cttgggagca tctctattcc tgaggctgtg ctgggatggg gacacgtgag  36960
ctcctgcgca tacccccagg ctggggagcc acagtcattt acattttcat tacaagggac  37020
aggacaagag taactgttcc ctgagctgca agtgtgtctc aggcttttga gtatagggat  37080
ttccatattg cctcctgcaa accactcatt caacccactg ttcagcagag gaggccagag  37140
```

```
agcccgaagt caagcgcctg gtctaaggac cttagtagat gagatttggt cctaggtcta  37200
tcgactctaa agcccaggct ccctcgcctg taccaacttg cctatgggtc ttggcttcaa  37260
ggatcctgga agtagatgcc aaatggtcat attgcacagc ctacctgagt aaagactagg  37320
tgggcatctc tttgtccttt ctagccacac cagggaaagc agccaagtgt cctcatgtgc  37380
agtggctaag tagtatagat ctgggatgga agtccagctc tgctccctcc atgagactct  37440
cagaaagcaa cctacacact ccggggcttt ctgtctgtct gggaggtacc ccagctcagc  37500
agtgggcagt agagaggcct tacctggagc ctggaaaacc atgcctagac ccagctttgg  37560
ggacgagatc tatcacaaga gagacaggaa tttgaggtac ctgtccctct ctggactcta  37620
gaatacctct ccaagagatg cttgtcaact tgtctccttg gcctcttttg tcctggcctt  37680
ccaagagcct cggctcttta ggggtgaagg gaccggtagc cagcactgct gggtccttga  37740
gagcctgtaa ttagaactgt ctatttaggg acacagcaaa tgccttatta attataaaga  37800
aaggaagcag acagattgtt taatcattgt ccttgttgaa aggttatgct gttaactgta  37860
taaatattca ttgaaagttc agttggctgc ctgcagcact gggggctgca gagccaggtc  37920
tccgaggtgg tgcatctggc caaaggctat ttcagtcacc tcggctttgg gtaaggcagt  37980
ttgggattgg ccctcagtca tgcatggttt gatggaagga cagggttttt gtccgactat  38040
aaacttttgg ttcagaggaa cccagactct gtctttcatg tgctgtgcat atttgggcga  38100
gttactaggt gtctctgaac cttaggactg cctccccctc atctgcacag tccctttgag  38160
agtggtgttt ctgggatcta ctcacaggct tcttgcctat cagggttcag ggtgggggca  38220
atgatgagtt ggttctttgt cgtctctgtt tattaaaaca aaatgtcaca gactagactg  38280
ggtatgttgt aaatgacaga aatctattgc atatagttct gatgcatata caggccatcc  38340
acagactggt gtctggtgag ggtccatttc ccacagaggt tgctttctca cccagatctt  38400
tgtaatagag tggcatggag tctacctcca acatctctat tatattgtat aattatatta  38460
tattgtaatt ttgcttgtgt atttcacata catagtactg tggcccataa gtacattttc  38520
ataaagatgt acattgtgta aagcttgttc cttacgtcca cccttcccgc tcctgtttta  38580
gcccctgtgt tcctttgggt aattctgctt ctattttaat atcatatata cacacttaat  38640
tttatatacc tatataaaat tagaaccaca aatgagaagg catgcaatat ttgtctttct  38700
gagtctagct taattgttta atatgattat ctccgattga attcattttc ctgcaaatga  38760
cattactttg ttctttatgg ctcaaaaaaa aattccgagt gttcaggtgc gtgtgagtct  38820
gtgtgcaggt gtgtagaagg atatgtgtgt ctgtgtgcag gagtgtgtgt atagaagggt  38880
atgtgtgtct gtgtgcaggt gtgtgcagtg tgtgtatgtg cgtgcatgtg tgtgtgtgtg  38940
tgtgtagaag ggtatgtgtg tgtatatgta tgtgtgtgta gaagggtgtg tgtgtgtgtg  39000
tagaagggtg tgtgtgtgtg tgtgtagaag ggtgtgtgtg tgtgtgtgtg tgtgcgtgtt  39060
ttgttttgag ccatctgcag cttttctgag agggcattag ctccattggt gatggcattg  39120
ctctcagtgt cttagttgcc tcctacaggt ggtcaggtgg aatgggaaaa cagcattgaa  39180
cctgagcagg ctgacccact tacaggcctg taactgtggc cgtagccctt tccactcccc  39240
gtgaggctaa gctttatgag tgggtagtgc ccagggctca ccttctccac cacccgttgc  39300
tttcttgggt gggtgggggg ctgcaaacat ttgaagccct ggttcactag ggggccatgg  39360
tattaccaaa agatgaagtg tgccatgcct tttccacatg cagactcagg ctgtcccaca  39420
gaggtatctg gatttggttg aaagtagtta ctaaggtgca ggttccaggg cctggagctc  39480
aggggttaaa cgtgctttct gctttcccag agggcccggg gtttggttcc agcacccagg  39540
```

```
gatctgattc catttccctc tccctaccat accctataca gaaagcagac acacattcac  39600
tggaaggaaa atataaaact ttttaaaaat gcaaattcct ttaccttcag catcccgatt  39660
cagtcaccat gacttggggc caggaacttg agctttcaac agccccctca gctcctgcct  39720
ctcggttagt tccgtctgag agccagcagt cagctccggc tgcttcatgc tctgaggcat  39780
caagaagtgc tcatggcatt ccaacattga tgacagacgt gcccttccca aatgcccacc  39840
ccacttcatc accccacaag acaaccaaag cagctttttt tgttttgttt ttgttttttg  39900
tttttgaga cagggtttct ctgtgtagcc ctagctgtcc tggaactcac tttgtagatc  39960
aggctggcct tgaactcaga aatccaccta cctctgcctt ccaagtgctg ggattaaagg  40020
cgtgtgccac cactgcccgg cccaaagcag cttgctttat ttatttattt gtttgtttgt  40080
ttgtctatct atctatctat ctatctatct atctatctat ctatctatct atctattggt  40140
cagggttttt ctgtgtaggc cctggctgtc ctggaactca ttctgtagac caggttggcc  40200
ttgaactcag agatttgccc atttccacct cctgagtgct ggaattaaat gtatgtgcca  40260
ccatcttcca gcaaaagtgg ccattttaaa agctcactga gtattcgaga tctacctgac  40320
agttacctca tgcagagtga actgtgaact gcagctgact ccatgacagg tgttcatggg  40380
atagcttcag gatccactct cctcacactg aagtagtgtg tgatcacctg ggaccttga   40440
tttagacacc cgcccctccc cctgcccact gcccctaacc ctgtctactc ctcctacccc  40500
tgcccactcc ccctgcccac ttcccctccc cgcccctgcc cactcccccct gcccactcac  40560
ctccccctgc ccacttcccc tcctcctccc cactgcccct catcctaccc actgcccctc  40620
accctgctca ctgcccactt ttctgtgcct tttcttgcat cggcccgctt ttgttctctt  40680
gtggcctttc attccagcca tgaaatcaaa tgagaggaaa cagatcatag atcagagcga  40740
gacaggaatc acccttcttc tgggggtata aaactgtgta tcagacaaat gtgccaaacc  40800
ctcatgtcat tcttgtgtgc gtgtgcatgt gtgtatgcgt gtgtgtgtgt gtgtgtgtgt  40860
gcatgtgtgt ggcatgtgtg tgtgtgtgtc tggaactcaa gacttagcat catgtctggt  40920
atccagcagt gctcaatgtt attcattgaa tggatttaca agactcggag tctcattgat  40980
tatgtgtgga taatagtaac acgtagcaag cgtaggctga gtgttcttct aagcatttta  41040
cagatattaa tctggtcact aaaacgatcc tatacagcag gtcattgtgt cacctacact  41100
ttattgagac aaagagaagt ggttaggcta aggtcacgtg gccagcgagt gactgagctc  41160
cgattccagc ccaggcagcg gcttccagag cccacaccct acttcccacg ctggaggccg  41220
agacataatc ctcaccctgc agggttatta taaagatcaa atggaagcgc ctagcactgt  41280
gcctggcaca atctaactga ggccgggact cctgcacact gtggaaggca tcagggagcc  41340
aaccagaggt cgtaaatgca tctgcctcgc ctgtcatgtg gaggaaggga agctcagagg  41400
aagagcttcc ccaagtcctg aaagggttct cattctttca gattgagaat caacccaggg  41460
gctctaggcc cctgcttgag tcagcctctg attgcagctg cagtaattat agctgcgtac  41520
tcccgctggg tcctgcacgt ggaggctgct ctctgtggtg ggctcaacac catctttgca  41580
gagacttaga ttgttgctgg taaggttttg gtgagccctc caaacccaca ggttcagatg  41640
acagttgctg atctggaagg taaactgagg tccagttagc catatcttac ttacccagag  41700
gcgcacagct ggaacatatc aagggtgtgg cgactccaca gtgctggatc ttaaagggaa  41760
gacatgtagg agcccttggg tcaagaaaga cttgtgagct ttagactagg agactctgag  41820
agagtgttag atccggtcgg tgtggggtga ggtcggattt aggacacagc aagcctttag  41880
```

```
aagaggttgg cttccgatga agacatggag caggagggcc ccagtggact gccagggact  41940
taagcccagt agcaggactg gttggtgcta tgacctgtgt cacccttagc taagccgtgc  42000
acggatgtct gtctttacag ccagtgaaga gtgtcctgcc gagaagttaa gctgcggacc  42060
caccagccac aagtgtgtgc ctgcctcatg gcgctgcgac ggagagaagg actgtgaggg  42120
tggtgctgac gaggccggct gtcccacctg tgagtccagg gccagtggtc aggcagcctc  42180
ggagtgatga cctcttcttg ggagggtcgg cgggaaggga agaataatgc taccattaga  42240
aacaaacggc tgggcacgta ggagacattc tcttctctca ccctcatgac cacctcatga  42300
atagccatta ccatccccat ttaatggatg aggaaactga ggctcagaca agggaggaaa  42360
catgcccaag gctgaggggg tggaactgag attcaaattc aggtctacac acagctttct  42420
accatgtctg acatctgctc atccattcta caattctacc gtttccactg atctccgaac  42480
aagaacaggg ggaccaaaaa ctgggctgta cgaaatgtgg tgtctcgtgc cagcacacta  42540
gcagcactgg ggatagggca tgtgcggaca gactctcagg gtgtgaagga caactgtttc  42600
tgagatctca gactggggcg catgtcgcat gcagagaagc agcctcagca gggacagatg  42660
gaagtggcca ttgggacggt tccacatggc tgaacttcaa acgcaggatt atctccttct  42720
cagagagcag tccagcaagg tttgggctgg gggtctgggg aggaccatgg ggaggaccat  42780
gcatggcctg attcagttta cttctctggt acccacagtg tgccaggtct ggagtaaggt  42840
tctgaaaggg acaagacggt gatcccacat agtcttcccc tggggaccac agactgacag  42900
gctgtgctac tagcctgggc tgagatatat gtggtcattc cggaggaggc gtgccaggca  42960
cttgcccacc actgcctctc caggcatctg cccactcccc gctctctccc tagccacctc  43020
tcctgttcca ggagccaggc catctcctct taaggcttct gagattccaa gtgtggagag  43080
ttgatgggtc tgaagcagga agtgtgtgga tgggggtgag ggtcctggct agaatctaca  43140
ctttaaaact tcagctgtgg agagatggct cagtagttaa gagcaccgac tgctcttcca  43200
agggtcgtga gttcaaatcc cagcaaccac atgatggctc acaaccatcc aataatgaga  43260
gacagctata gtgtacttta catatagtaa atacatgttt aaaaaaaaaa agaaaaaaaa  43320
aacttcagct gtgatagttc tatgagaact catccaccca tgacagtccc caccccccca  43380
aaacaggccc aaccttatag tcacatgatc cttccattat aaagctagca gccaccattg  43440
caggcgagta gggaatttgg ggacagggac atttcctgtt aattaaagaa accaaagctg  43500
agaggcccta ttgggctcgc tgtggcctgg gcagggaagg aaactgtcct tctctggctc  43560
tctgagagtt ctccagttct gattgtagat gcagggagtg gggccctggc cttggtggtg  43620
agatctgcca gtcgcttcag aacctcactg ggagtccatt gttatgaaac acttcctatc  43680
aggactctca gaaggtggaa tcttctctcc ctgggcttgt atgaactgtc tagacaggca  43740
ggcgggtgtc agcagcagca tcttgggggt gctttcccct ctggtgccac cacatcccaa  43800
aagcccaaga cagggaaaat gcagccgtca ggggcttggt agagctgtca gaagaacatg  43860
acacgatctg ctgacactgt aacaccgaag acatcacttt attttatgtt cagtaacagt  43920
gaaaattgac atcttgtcgc cagaaaatag aaaggtgggt tccgggcgcc cccgtgtgga  43980
gagttgcgga gctgctactg ctgtgtagtt ggcgattaat agccacagca tccctgacct  44040
ccttgagccc tcccacggga gttctaaaga gggggaggag gcaacacccc aaaccaacca  44100
aacaaaaaac aagaaagctg agagaatggg tcagagtaga cagaaatgct ctggaaccca  44160
agttctggtt ctcttgtcac gtgtgaccct gagcaaggtg ctcccctctg agcctcaggc  44220
ttcctgtctt taaactagca ggggggctgg ctggtcgcta aggcctttgc tgtagacttt  44280
```

```
gcactagcct atcagagagg aagcccaggc tgcagacagg gccaggacct gttctttact  44340
tcgtccacac cctgcaaggg gcctccgtgc ccacccggta cccagacatg tgggtgatgt  44400
gggtggatgt gagaggcaca caggaggcag actgggccag agggagattt tctaaactga  44460
agcatgcgat ggatggaggt ggagtttgag cccatgcagt ggaaacgttc tgatgtagaa  44520
ctaggagcaa tggtaggctg cagtgggttc ccagaagatg aagcaacttg aacaaaaccc  44580
tggagtggaa ctatgtggtc atagccgggg tatgtgcagg agtgaggtgt ggggaccagg  44640
gtagtagatg ccaggctgga gaattaaata gtctttgcaa gtgatataca caaccatgcc  44700
acaaacggac aaactcctgc cttgtcatct ggtgtcagtc atgttacaga tgatttccta  44760
tccttcaaga caatagggct ctgcaacctt agagcccctc tctgccccac catgtttgcc  44820
agctgcaggg cagaatatct gtgtacttgg tgaagcccag agactcagaa agggcaaatg  44880
tggtcggtcc aagttcagct cccctttcaa gtctccagca ggacctattc cagcctgtag  44940
gtgaggtgag agtcagaatt ccctgtaccc ctgtagcaga aacagcgggc tgggtcacaa  45000
gggatgggat ctggccggcc gaccggctct ctgtcctgcg cagtgtgcgc cccgcacgag  45060
ttccagtgca gcaaccgctc ctgcctggcc tctgtgttcg tgtgcgatgg tgacgatgac  45120
tgcggcgacg gcagcgacga gcgtggctgc tcggacccgg cctgcccgcc ccgcgagttc  45180
cgctgtggag gaggcggcac ctgcatccct gagcgctggg tctgcgaccg ccagttcgac  45240
tgcgaggacc gctcggatga ggcggccgag ctctgcgggc gagcgggcca ggggaccacg  45300
gccacgccag cagcctgcgc cccgaccgcc cagttcacct gccgcagcgg cgagtgcata  45360
cacctgggct ggcgctgcga cggcgaccgc gactgcaagg acaagtctga cgaggccgac  45420
tgctgtaagc cccctccgtg tcacccagtc ccacccagag cctgccgata tgaccctcct  45480
actgggagta caaaccctgc tttaacagag actttacact gggagaatga agtgacttgc  45540
aggaggtcac atggctgcta aggcttggag ctcaggtctg accccagaag ccaggcttct  45600
tcactggtgc ctttgtctct gctgtgtggc cattccatca cacccgttgc tgctctttac  45660
tgtttcaagg agtctggcac tggtccccat cccccacccc acccccacct ctgtcatact  45720
gacgtaggag tgccttccat accgaccctg ttagagtctg ctgactgttc cagctctgtt  45780
gggtcccttc caggactttg gctctctctt ctaggcacaa ctcacactgt gccttcttca  45840
tctgtgcgtt tcccatctct ctgcacctga gcttctgaaa taggctctta gtctccgggc  45900
tccccaccaa cacccagcac agtcccgggt tcaggacagg ttgactgagt ggaccacatc  45960
actaagtcat gagcaccagg gctcagtgga aaaagctcgt gtctgtgctg aggtggtgga  46020
cagggaaaca ggaaactgga gtgctgtgtg acctttggca aggccttccc cctctctgag  46080
cttcagtctc ccccatgtgt acacagatgt tttgggtagg tgtcctttga ggtctcctaa  46140
gctcagtcac tggttcattc tttccagggg cggaagggac atgaggtggt ggggaaagct  46200
gttctggccc tgcgtgggtc ctgaccgcct cttgccctgt ctcagcagca ccaggaccct  46260
gccgcgagaa tgagttccag tgtggggatg ggacttgcgt tcttgccatc aaacggtgca  46320
accaggagcg ggactgcccg gacgggagtg acgaagcggg ctgccttcag ggtgcgtgag  46380
gtctctgaga ggaaaggccc gtgaccctcc caggctcaga gagaacagag ctgggggggc  46440
tcctccctct aactctgaga tgatcccttc cacatccctt gcccgttatc cttggaattc  46500
cttcccatga ggatctgggg tccaagaact ggacttttgg ttaaggactt tgtaaaggct  46560
gaagaggact aagggggtaa gatgggcact gcaggggatc tagccttccg ctgtctgtcc  46620
```

```
acacccgagc ttccttgtgg ccttccttac tagttcctag acagggcaga ctgaagccct  46680
ctcccaaccc cctagagagt ccctctcaat ctcaggtggc tttgttggtc actacctgcc  46740
ctgcagggat agaaacccta ctcgctcatc atctgggaga gttcatttca gagtgggcaa  46800
tgaggagtga accatatccc aggctcatgg agcaaacatt ccccccttggg actcccagga  46860
ccctaagtgc ccccaggaca gacaaagact cttgtgtgga tatatgagga tctgtcctgt  46920
gagagagaag actgtggttc cattgtctgt cctgtggtcc cctaagagac ctgttgggtt  46980
ttgaactctg tgcgttttct gtgggccttg attggccctg cccagccttg tgcttcccac  47040
cccccgtctc acaggcactg tccactctct tgtctggccc gacagagtca acttgtgagg  47100
gtccccgcag atttcagtgt aagagtggcg agtgcgtgga cggcgggaaa gtgtgtgatg  47160
atcagaggga ctgccgggac tggtcggatg agcctcagaa agtgtgtggt atgctacctg  47220
tctacgccta acagctgaac taatgctctc accatgctcc ctcctggcat ccaggctgga  47280
ggccctctta ccctctagac cgagtgttct cctgtagcct cacactgggc catttgccac  47340
tggcatctct tggtctgtat tgttgcaaag cccggggccc tcttctgaag caaggctact  47400
tctcacaaaa tctcatttca ggcactgagc ctgtgccctc cacaagtttc tcccttcctg  47460
tgttcccgtc ctgctgatct tcccgtgacc ttggctcctg agctcttcca gtctttggca  47520
ggacacctta caaagtcaaa ggttggcgga agcagccagg gaggctgtta ggagcatgtc  47580
ccagcagcag gcagtgtcac cattctaaat cccaagattc tggaactcct gaaggagccc  47640
agaggtgcag tctaacgaga gagaagtagg gtgagccagc tctccaagga ctagtgagga  47700
gggcagaggc tctgagctgg agtggagcag gagcccatga gtgcagaaga gtttgtgagt  47760
catctctgct tgtctcaggc cagaatttag agacctggac aaaggagtcc ccagagaaca  47820
gagtcagatt ggcccctcct tgtcctctca gaccacccac atctcccctc ctgggtaccc  47880
cagagctccc caggatcagg tttgcccccc cccccccaca cacacactga agatgtaaat  47940
gaagtcagac tgaaaggaac cgtagttagg caaagctggg cttgcacaga cagacacccc  48000
actgcccgca ggccttgcct ggagacatcc agaagagaca gagaaagggg gacagggaag  48060
gagcggccga ccctgtttct ccacaacact cagctctgta gctacgcagg gactactaac  48120
ctaccaaact ctcatcttct gcatgacatg tcaaagagaa atatgtgctt gtttgtgtcc  48180
acgtgcgttc tttttgtctg tgctggtggg tgacaagtgt ccgcacccac gtctccgaat  48240
tactgtattc atgcatctct gactgcattt ccatctctgt agagcccgca ggacctgtcc  48300
gtgcctctgc acataagcta gtgtgtgtat gtgtgtgtgt gcatgaaggt gtgtgcatgc  48360
aagtatatgc cgtgctgggg agagatgaca tcaaatactc aggcctccag cccctcttcc  48420
ttcctctcca ggccttccaa agaagaccat cagggataaa ctaatcgggg tctcctagct  48480
tttctctctc agcccatggt ggccttgagg cactccacac cttctttcgt cagaagctac  48540
aattatgttg agctcttcct gggcagcagc gccctacaca taccatatgg ctaagtgtcc  48600
agtaaataga actgcgggtt gctgtgactt ccaaagagag aggaaggaag tgggtgggta  48660
cgtgactgag gccgcgagtg aacgggaaaa catgaatgca tggtgcttgt ggaataataa  48720
aacccaagac aagcaacaga gggtgtgagt ggccaaatgg ttgccagtgg gagctctccc  48780
agcaactagt ccaaagccac catggctcaa acgacttcca gaagtctgcg gcttcccagg  48840
gattggactt gaccaatcta ctcccagtcc cccaaagtca tgggctcgat gtggtcttgt  48900
tctttcagtt gcaccatcat tcccgggaaa caggaggcat cccaggggta aaggggatat  48960
tccctaagca tggctcgggc tggaggtggg gatgctcaca gctgtgcatg gcctggcatg  49020
```

```
ggcagctccg accagctgga tgcatggcca cggctggctt cgctcagcgc tgctttgctt  49080
ggctggagtc acggtgcatg agcctggtgt gcagaggggg tggcacagta ctttgccctg  49140
gcttgtgtga gtaactgtcc atgattctaa gctcagaggg cactgagaac ttggtaaacc  49200
ttggtcctgg cctctccaga aggtggtgag gaagtggaga atgaggggcc agacccaggc  49260
gacctcttgg catcccttca ccctttgcag cacttggtaa tcctgggcta ggcttgtggc  49320
aaggtagatc aatgagacag gtcagagagg agttgaaaag gctccatcat gtaaagccct  49380
gtaggagaga attatggctt ggccacgggc atattgaaaa gaaagtgtgg cctagagacc  49440
cagctgtagc atgtaagggc cttctgctta cactgtctga cttcggcgaa ctggccaact  49500
aattcagggc cctgccttga gaaagcacac aaatagcagg ggccagaagt cagcagttga  49560
cagagatctc aggagcccct gcaccttggc tgaccccaca gagcagaatt gggaagagga  49620
ggaaagctac aggaggcagc tcctggagga agaggtttgt aagagcagca gcactccaaa  49680
gtggtgtcac ctgcctccgg agcctgccct ttttgggtgt gcagaggcat tcggcaggca  49740
cttgggggat accccagggg tgaacgttat acacgcaagc ttcagcttaa aggttagaag  49800
gaagaaggaa ctattttaaa aaatgtgttt gtgaaagacc tcagagcccc aggtaagacc  49860
tagctgcctc tagtctagtg gtggatggag ccctggccta ggaggacaag gacttgtgtt  49920
ttctttgttc cactggccct gtctaaccag ggagcctgcc ctctgatcct cctcctgccc  49980
atcacctggc tattggttca gtgcagcttc ctggtttcct ggtggtgggt gtctgctgcc  50040
ccaaggcttt gctttgctct gggccacttc cctgcctgtc agagtagttc agcagcctgt  50100
gtccctcccc agggctaaat gagtgtctgc acaataacgg cggctgttcc cacatctgca  50160
ctgacctcaa gatcggcttt gagtgcacgt gcccagcagg cttccagctc ttggaccaga  50220
agacctgtgg tggtgagccc tcccccatct acccgagcgc acgcagagcc tcctgcccag  50280
tctgactcct ggtctttccc gcagacattg atgaatgcca ggacccggat gcctgcagcc  50340
aaatctgcgt gaattacaag ggctacttta agtgtgaatg ccaccctggc tatgagatgg  50400
atacactgac caagaactgc aaagctgtag gtacggactt cataaaggat aaggaacact  50460
ctggacggcc tagaaaacac aaaacttcca catatgtgag gagtggttaa gcatacacgc  50520
acacacacac acacacacac acacacacac acacacacac acacagaaag caaatgggtc  50580
acacaaagtg ctcaaagtac acgtgaacat cacatacatg atctgctgca ggcgcatacc  50640
cacaggcatg cttagagtca ttcatgatag cctgcagttc acattagcac agcacaatgt  50700
ataggcacaa gtttggacca cagagccagt atgggcagct cccacgaaga gcaggatgtg  50760
tgcagatctc tacgttgatc cgtttatcca gatgatttaa ttatttattt cttcatatta  50820
aatgcagtag tactgctgta ggcactaaga ttcagtcagc aaatgacaca atgcgcttgt  50880
tagtgaccga gacaggcaga aaatgagatg gctaaacaaa atacagcaca tggcaggtgg  50940
cacgtgaggg ctgaggggac ggagagtagg gattggggat gggaagtctg agggaatggt  51000
gggttatggt tttaagcagc atagtcgggg acgctctcac taaggaggtg acattggaat  51060
gagaagctga aggaggtgaa ggggtgggca ggaacggcat tccaggctgg aggaacagaa  51120
tgagcaagag ccctaggcag ggagtgtgct cggatggtga cggaaccccg agggagctgg  51180
tggggttgga acaaggagac tggggcagag gtgaagtcat aggtgtctgg ggctggggca  51240
ttctcccagc cttccagacc attgtaaagt cggacgtggt ttctcctgag tttgagagaa  51300
gctatcaaag ggttctgagt ggaatgcatt gtcatgttta agctctgcct ggcttcattg  51360
```

```
ctgagaccag actgcacagg gccagagcgt acacaggtta ccgaggtact tcaggagaaa  51420
ggcttggggc agggtgggtg ctgggggaat attgagaggt gaacagatgt gtgtatattt  51480
tgaaggccaa ccaacagggt ttgcttagaa gtttaatgtg ggattctaga gaaaagtgaa  51540
tcagaagatt ccaaaggaca aatgaggaaa aaggaatatc tatttcatta tatgagaaag  51600
atggtgaaag aggcaaatct cagaggactg tagaccgttg agaatacgga aactgtagct  51660
ctccacatgg aggtattgaa cggacagttc agtcaaagct tggagtttca cacacatact  51720
tgataggacg catagatcac agtaacacag tagctatgat acttgatatg aaacccatca  51780
atcctaaaat atcccaccca catattcaca tgtcacatgt aacctgtctt tacttccata  51840
tggaacagga gtgacagggc ccatatgtac gagtatatgg tgacaacatc ctgaatatat  51900
acactaaatc atgtgactat ctaaggtaca gttatacaaa aattcaaggc ataaacacac  51960
aggtccctgt tgctgacaca gtcctcaata aaatccacaa gaggccctct accccagctt  52020
acgaccttag agaggggaag tcgtgcctgc acttagggtg aggaaaagtt ctggcgactg  52080
agcaggccta gaacctagct ttccgtctgc tgctccctgc actgtgagcc ccatttcccg  52140
gctctttgta tcaccacttc cctcctaccc ctctgccctg aaagtttcca tcactacaca  52200
cagtatattt gtgtgtatat gacacagccc tggtcagtgc gtggctctgg actttgccca  52260
tcctgtcccc attagcctgg cacagatgca cagaaaccgg accaggtggc tgacaggaat  52320
gtgtatcggg aaacatggaa ctgtgcctga gaattgcctg atacatctcc aaaccccctg  52380
tgagcggggc agtgcaaggg ccttacggac ctctgggaca tcagtcttcc aaatggaagt  52440
cgagactatc taggccccgt gggatcttct gaatcttact ctagggtcta aaactagctt  52500
ctaagtatac atggtcagtt gtatgttctg tccagtgcat gcatgtgatt tgtcagatgc  52560
cacatgtcct acctccgttg atggctcagc aaacttagcc tagcccactg ggctatcttt  52620
ctaggacctt tatgcaggat agcaggtgga ggcctgagca gaaaggcttg tgatctctgg  52680
aaagaagcac actccagggc aaggggaaga cttgaaaggg gcctgggtcg cgaagcttgt  52740
ctggggaatc catgatggga gaatggctgg tgagccagac ggacagcagc agggtcatgc  52800
tgcaaacgtc tcctcagtgc aggcatgcgg gcacagggag tcatggactt gggagtttgt  52860
acccagtaga gaggagagct tctttctgct gtgtgctggt actcattatt catctgccct  52920
tctagcctgt gaggtaggga ccatcatccc cacttcatag gacaacgaac ctctcaccca  52980
gcagacgagg ggcaggaact tgtgtctcta ggctccctgc attctccact gacactgctt  53040
ccctgcacgg cagccggcaa gagcccatct ctgatcttca cgaaccgaca cgaggtgcgg  53100
aggatagacc tggtgaagcg ggactactcg cgcctcatcc ccatgctcaa gaatgtcgtg  53160
gcgctggacg tggaagtagc caccaatcgc atatactggt gcgacctctc ctaccgcaag  53220
atctacaggt gagtgtcagt gcatgcggcg gcggcccagc atggggggct tgagggaggg  53280
gcgacttaca gagaagaggg cagttgggct tgacagggga catggaatca tagcaggagt  53340
agaagtacca aggctcatca gcctgtaggg aaacagcctt gagtccacat cctagactgt  53400
gtctgaccca tggtggccta gccgtgaagt gcaggacatg tgggagatca ggtgtcgggg  53460
gctgggcagt ctgtggctga gggacaggaa cagggacttg cagtctgcag tgcattgagt  53520
aaaggtgcca tgtagcatct aagagtgctc tgcagcctgg accttaaggg aattgcccgg  53580
attgcagagt gagagttacg gatggcagca ggcagtacgg aagcaataac atggagagga  53640
cccctcgggg gagggacagc aacctgactg acacctcctg tgtgtgtgtg tagtcagctc  53700
tctctgcact gcacagcctc ctgcagactc tcttcatctc acctctgtgt gccataacct  53760
```

```
cccctcagcg ctctcccttc ctccccttcc ttttgagacc atccattccg cagctgccac  53820
agtgatctaa cattcacagc tatgtcccta gattcattcg gttacctgtc ccacccttgc  53880
cccaggacac aatccagcgt gctcagagct gttcccgtta tttccggttt tgcatcccat  53940
catcaaaccc taccacacca aaccctgcct cctttccaaa tgtgcgcact tctgcacttg  54000
tatgtgctgg tttcggcatg tttggtctca ccttctgtgc ccctggtgat ctagtccttc  54060
aagactcaac cacaaaggct tctcccactc tgcagaatgg tgcagtctcc atttccctgc  54120
tgccgtagct tccacactgc attgtacctg cctgcaagct tcttccccca ctaactgagc  54180
tcctccaggc cagaaactag ctggttcagt ccgtgtctct accctggtga cttaaggaat  54240
gtgttgagtg gagattagtc gagttcctct agaacccact gccgtggccc agagagaaga  54300
caaaggggag ggttgcagag gcagctccac gtgggcccat gggtggagca tctgcccatg  54360
gccagccctg ctttctccta agcgcccaca tggacaaggc cagcatcccg gacgagcagg  54420
tggtcctcat tgatgagcag ctgcactccc cggagggcct ggcggtggac tgggtccata  54480
agcacatcta ctggacagac tcaggcaata agaccatctc agtggccaca accgatggac  54540
gccgccgctg tactctcttc agccgtgagc tcagtgagcc ccgagccatt gccgttgacc  54600
ccctgcgagg gtgagtagcc ccacagaaac cttccattcc accagcacag gggctcagtt  54660
ctcatgtgtc tgttatgaga gctgtcaaag gttctacaag tctgtggggc ttctagacag  54720
acacagggaa ggaagtccaa gcggcccaca tcctatttgt cctcagccaa gggatcgggc  54780
attagtcacc agagatcacc ctgaactctt tggctccttc actgtatcgc tgaaatggcg  54840
tgtcttggaa tgctacagga ctagagatcc ctggaagctt cagaggtaga ggccatcggt  54900
atctggcagc tgcttaatca ttttagggga cagagaactc attccttttc atagttccta  54960
tttcattgtg gggtgcctac ccattacaca gtggtgtttt tcctcataat cgcaaatctg  55020
tctccctata acttccccca gtgggagtta cataagcact cagtacaacc agaaagattg  55080
aaggatgcag gtccctgggg ctgctctgtt cctagctcct catctttccc cagcccccacc  55140
cttgttgccc cttgtgagcc cctttaacct aggctacttt actctggcca cacctgggtg  55200
ggggcttagg acctccctta gtggaaatgt tccttcttcc ttcctcatga aagggtgaat  55260
tagcaacagt gagctgctgt gatccttagt agaaatgcgg gtccaggagc agggacctgg  55320
gttaggatgg tcttttagtt tcgtctctgt aatcgggaga gctgtgtaag ggcccttccc  55380
acacagatgc tctagggttc tggttagagc cacccagtga gagccgagct cacaggccgt  55440
tcagctgaga ctgcgtggat tatgggcaag ttgagcttcc ccaggctctc atgagatgaa  55500
ggttaaagtg cctgttttaa gatttgatag ttccaaaaaa tttcagaagt ttgcccatta  55560
aatataattc ctaactgttc agtggatcgc tgagcctttg cgactaagac tactccaact  55620
atcccaaaca agaagctaat ttgggctctt ctgcctttca ggttcatgta ctggtctgac  55680
tggggtttcc aggcaaagat tgagaaggct gggctcaatg gtgcagaccg gcaaacactg  55740
gtttcagaca acattgaatg gcccaatgga atcaccctgg gtgagccctg cctgtctacg  55800
tgagtcgggg gcctgcacta gaaatgatcc tgacagctta acatcgcccc atggtcttga  55860
gtcagagtcc cctcgtggtg gccagtgtct ttgttccctt aggctgggaa ttgtgggtag  55920
ggagtgcagt ggagtggaga ggcagctgca gtaactggtg tctgacctga tccctcctcc  55980
ccaagacttg ctgagccagc gtttgtactg ggtggactcc aagctgcacc aactatccag  56040
cattgacttc aatggaggca acagaaagat gctgatcttc tccactgact tcctgagtca  56100
```

```
ccccttttggg gttgctgtat ttgaggtgag ccccataggg ggaggcatgg ccctatcggg  56160
aagctgcaac ccagagaagg cttgttcaaa taggatgctt ccagacttgt ccaaagggaa  56220
acaaaagaac agggaagcca gctgacaggt ttgtatagac tccaagagca gcctccacgg  56280
agggccagct gcccagtctg cctggcagcc tttgctgtgc tcttcccgag agcctcgttc  56340
agataatgtc acagaagcaa ttcacttctt ctccacatgc ccagcatcta gcgctgtatc  56400
tcacatacgg aaggaggcag ggagaatgga agatgcatgt ccttagaatc atttattgta  56460
gggcacaccc tgagagatgc tatgcactta ggctcatttt tgttgacctt tgctaagtcc  56520
tggctggggt ggtagaagta aactagaccc tacccaagcc ctcgggaagc tcccaagaag  56580
gaaaagaatc acaaagccca tctgctctga ccttaacatc ttttcttttt gggaaataag  56640
gaagccagaa cctaccaaag tttcttacac acagactaac cctgccatca agggaaggca  56700
gagtaaggag gtggtggtct gtggtgggaa attggcagtc ttttcttaga gcagcttcat  56760
tcagtactgt ttgaacttga gtgcagagta tctcctctaa atctagcccc tgcttcaagt  56820
ctatgtatgt gtacgtgagc atctccctgg catgtgtaaa gtatgtgtat gtgcatgagt  56880
ttgcacacat gcaccagagt aaacacgtat gttcctgtgt gtgcttttat gtgtatgtac  56940
actgaaaggt atttccttca gcatgagtat gtctttagga gtctagatgg acttgtgcgg  57000
gtgtgtctgg atctgtggac aagatgcatg gctgcacctg caattgtgga ttgcctacag  57060
atgcgtgtct agtcttctat ggactaacca tatagacttg tgtgttcctc ccagaaggct  57120
caacagcaac tagccctcag gatctcacac attccttctg atcttagtcc caagccgcag  57180
gaatggtgcc agctgtagac atccaacctt ggttttcttt tggctccagg aagtaagcct  57240
agctcagcaa ctcagagtca tcacgtaatc atctaagaca agggagcgag gagactttgc  57300
ttcactgtta gaggcagagt cctctgaaaa cctgtgggca gggtagatag cgctgagacc  57360
ctgatttggg gctagggatg gagtttggat tctggccttc ctgtccttta catctgtatt  57420
ccacaggaca aggtattctg gacagacctg gagaatgagg ccattttcag cgcaaatcgg  57480
ctcaatggcc tggaaatcgc catcctggcc gagaacctca ataacccaca tgacattgta  57540
atcttccacg agctgaagca gccaaagggt aagtcagtct tccccggttc ccaccgcctg  57600
tgtcctctcc tgccactcat ccagcatccc caggaataca gtgacccctc ttgttgttga  57660
acgtgttgct gtattttgtc tcacttctgc ttcagcctcg gtgtgaagca aggctaggaa  57720
caaataatcc cgtaagtgtc ctagccttgc caccactgta acaggtactt actgtatatc  57780
tcactgaaca gccgaggaaa ctgaaattgg agagagaaaa caaaaatata aactcagtct  57840
acctgattgc caagctcctc tgtgacacat cagtgcgcgc tcacttcttg cacccatttt  57900
atagtactat gaaatcatgt gactcaaggc ctcacagtta gccaggtggc ttactggaaa  57960
tggtcgaata atcatactgc agggctgtct catcggctgt cacaaccaac tgtaatgggg  58020
gttggttgcc agggtaacag agacaacaaa gaggggcaag aagataagat tggtgcctga  58080
ttctagttct agagatttaa agcagaaagt cacgacagcg ccaggcattg gtggtgcatg  58140
cctttaatcc cagcattcag gaggcagagg caggtggatc tccaagttcg aggccagcct  58200
ggtctacaga gtgagttcca ggacagccag aactacacag agaaaccctg tcttgaaatc  58260
cccccctcc ccacccaaaa gaaagaaaga aagaaagaaa gaaagaaaga aagaaagaaa  58320
gaaagaaaga aagaaagaaa gaaagaaaga aaaagaaagc catgacagca ggtacacaga  58380
ggaggaacaa acaaggcaag cacagtgggg gagagggtag ttttagtttg ggaattgatg  58440
tacctcaatt aaagtctgcc tccaaaattc ctagcgttgt aatgtgtaca tatattctct  58500
```

```
gagcgtaggc ttctctgtca gttgggaccg taatacccac ttctcagaac tgtaacaatg  58560
aatgaggggg gacaataaag tcccaagtac tatgctggta tgtccccaaa taaaagtagg  58620
gaaagacttt tgagcaagtc cagttggtgg gatctcatta ttggtagaca agaggacctg  58680
gtgaggcctg tcaatctccc aacacgctgt ctgtctgccc ctccccctgc cattagctgc  58740
agatgcctgt gacctgagtg cccagcccaa cggcggctgt gaatacctgt gccttcctgc  58800
tcctcaaatc tccagccact cccccaagta cacgtgtgcc tgtcctgaca cgatgtggct  58860
gggcccagac atgaagagat gctaccgagg ttagtgacag acgctgtcct ggcctcccag  58920
gacacagtat gctccagatt tcctccgtct tccctggttg cctctcacgt ttgcactttc  58980
gtcttattta cactaacttg aatgcatgag tcacggcacc ttctaaggct ttcccatttc  59040
ccagaaaagt gcaaagtgca taaaatattt taaattcaac tttcaggaag tttctggaat  59100
cccttgaaaa cctcaagtta gtgggcctgg agaaggctcc gtggctgaga gcacttgttg  59160
ctcttgcaga ggaccctggt tcagtgccta gcacctatat gctggcttgc agccatcctt  59220
aatatgctgg cttgcagcca cccttaactc caattccaga agttccaacc ttgattccct  59280
ctgctgactt ctgagaacac cacgggagct catggtgcac aggcaaaacg cccatagata  59340
taaagtaaac caatcttttt aaaaagtaaa aaataaaata aaggaaattc atgtaaagag  59400
ccctcactct ccgctgacca tcttttgcag ataaccattc ttagctagac ccagcacact  59460
gcatagacgc cctgagtgca gttgtcactc atgtgcaata gcactttatc ttcagcaagg  59520
ggatttgttt cccagtctcc gtgcacagcc aaggccttgg ggttgagcat taagtctgtt  59580
tgcatccctt tataatgtcc agagtcagct gtttgatgtg tttaaaccta gtgatgtgac  59640
tgtggattag gataaaatgc ctctggattt gtgtttctgc tccctctagt cttacagagg  59700
cctcttccac agtgtttcta cagcactgtt ccactggctc ggcttcatca catcaaagtg  59760
aagtgctagg actcagctgg agagtgttta gggggtgggg ggaagtctca caaaagtgtc  59820
atctgagcta agcccagagg acgtgcgtgt ccctacatgt aactcagcag caataattta  59880
ggcactaaag caacaacatg ctccgtgtac gtaacctccc tgctctctcc cctccagcac  59940
ctcagtctac ctcaactaca accttagcct ctgccatgac aaggacagta cctgctacca  60000
caagagctcc tgggacaacc atccacgacc ctacctacca gaaccatagc acagagacgc  60060
caagccagac agctgccgcc cctcactcgg ttaacgtccc tagggctccc agcaccagcc  60120
catccacccc gagccctgct accagcaacc actcccagca ttgtaaggaa gttggctctg  60180
tatttctcct aacttgggag agttctgtgg aagccgggat gagggtcgga agtggctggg  60240
aagggagatt ttgccagaac tatgtaatgt ccacctctta ggaggaagtg agggagagaa  60300
gggactgtcc tgggattgag caaacgtgag tgtccataag ttttaaaggg cctggagaca  60360
agccattcat tccatctcta agcctccttc ttcctcttaa aggaacaaat cataagctac  60420
actctacttg cttctcaaga tggtcaggag agcctggcag tgctggtgca catctttaat  60480
ctcagcagag acaaaggcag gtggatctct ctaagtttta ggccagcctg ctctacatag  60540
agagttccag gctacgtgga aagaccctgc ctgcctcaag agagggagct aggcaaaaga  60600
ggcattgtgc attgtaaatg gaagggccca gctgcctggg tgtgcgtcag ggtttcatgt  60660
gttcctgagg tgggtgtcat caagtttgga aagctctgat cagagctccc agcagcctca  60720
gtaagctgcc tagacagtaa cgtctgtgtg atctgtttgt gcctgtttcc aaaccctggg  60780
ataaaataat taagcttagc acttcttaat tcattgggag cagtaattgt ctctgttgga  60840
actgctctat ctcattaacc agaaaatacc tttataattg ccagggggag ttcattttaa  60900
```

```
agggtaaacc atctctcaca ttttttttcc atacttggct ggcccagaaa ccaagcaacc  60960
tagtgacgtt gttgcttggg ctattttgcc agcagaagct agattctaag agtagacttt  61020
gaggcagctt ggcatttgct gaggtgaaat tccatttcct ctcatcgggg gcagagctca  61080
gagtgtcctc acaggcctca ggacattttc aagcacatca gagcaagggg acagcagcgc  61140
ttctaactag cttgttttct tccttctctg tgtgtgtatg tgttgggggt gtgatatgta  61200
tgtgtgcata tagaggctag agatcaactt tagaagtgtt ctcagtagtt ctccgtctta  61260
attcttgaga cagagtctct cacagaacct ggagctcatt gcttcagata aactggctgg  61320
ccagcaagct tcaggtttcc tgtctctacc tccccagtgc tgtgggtaac atgcctggct  61380
gctgtgcact ggggagcaga actcaggtcc ccgttcttat atggcaagca cttaagaagt  61440
gcaccctcca gttagctaac ccggtgagca atgcagctct ctgattagtc agagtccctt  61500
gaagtaacac ggagaacgag actgagggga tggactgggg gacatttcca gtggctcacc  61560
attcctctca tgtttcagag ggttctcgtg ggatcccagg gcctagtgct gtacaggtgt  61620
ctcagggaag atgactatta gagttagcga aggatattta tttaaaatac agtacattct  61680
acagtcactc ttcagtttaa gaatgggctt gggctggtga gatggctcag tgggtaagag  61740
cacccgactg ctcttccaga ctgctcttcc gaaggtccag agttcaaatc ccagcaacca  61800
catggtggct cacaaccatc cataacaaga tctgactccc tcttctggag tgtctgaaga  61860
cagctacagt gtacttacat ataaataaat aaatcttaaa aaaaaaaaaa aaagaatggg  61920
cttttacgtg cctttaacaa caacaacaac aacaacaatc ctttctttag agatggggtc  61980
tcactatgta gcccaggcta gtctgaactt gagtcttctt atccttagca tcctgagtgg  62040
tgtgtgatac gcatgcacca tcacacatgg ctaacatacc tttttaaact tggcccttat  62100
aataattact atccccctca ctaccatctt gaattaggca aagccagcta gacactgtgc  62160
taagtatctt atatgaatta tcccatttaa tccctcagat atacccctta gaggtagaaa  62220
agattttaag ataaatatag tatgcattat atgtttaata ttatattagc ttccacagtg  62280
tcacacaggt aatgtgtaat agagatagaa tttgaaccga ggcctgacct agaagtctat  62340
gttcccagtt atactctact atgctctagt atctctcgtt ttaatctctt aggaaaacaa  62400
gcaggtagtg cataggatag gcagaccacc aaaacagtag agacaatgca ttgggttttg  62460
atagaaaaag acagcagact ccatcaacaa caaggaggcc taagctctct cctgccatgt  62520
agcccccagc ttcctaccat cttgatgcta tgggaaagta taggacttga gtcatgagtc  62580
ctgagttcaa gtcccaagtc tgtatttatc aaaatttagt ttcctgggtg tgaaataacc  62640
tctgccctat ttgcctctgg agttttggtg aaatatagta aactcaatag ttacacagta  62700
tctaggagca tcatcctaaa ggagaggttg ggtgggtggc ccttacaact tgagggcagg  62760
cagggcttgg attcacagtg atggacagtc attctgtaac tgatatttta cagatgggaa  62820
tgaaggcagc cagatgggct caacagtcac cgctgctgtc attggggtca tcgtgcccat  62880
aggtgagtgt ggccccaact agtagagggc aaaaggactc tgtgcccaag gtttggggac  62940
gacactagag ggataaagaa tgttgcatgc tgcctggttc aatgtgggct cttgcccggc  63000
acacagctct cttcaacttc tgccgccatg tgaacatcca ggcacatctc tctgccccac  63060
ccacctccac acccaacact cacatcatgt gaagaccaaa tgagtgctcc ctggggccca  63120
gctggtgtct cttgctcacc actctcccac atgccacatt ataggaaatt atggatttgt  63180
taaccgatga gcctgtttgt catttcttga gtaaatcatc ttgtcttgtt ttctttctat  63240
ttggttttta attaatattt atcgagcagc tattatgtgc caaactctaa tcaggaaagg  63300
```

```
gaaggtagtt aaaggataag taaggcaggg tcctatccta caaaagtcta atcttggttt  63360
agcaagataa cttggtgggc aaaagcactt gccaccaagg ctgactgcct gagttgtgtc  63420
cctgcagacc acatggtagg aggagggctg attcctgcag tatgtcctct agtttccaca  63480
cactccacct tgtagtatgc atgccctacc ctgcaaaata aataagtaaa tgtgatttac  63540
aataaaaacc ctagcaggac aaaggataca tatgacacag gtaagttgat tatgacatgg  63600
caagtcctaa gagtaatcta tgttactgtg ttgagtgggg gattctaagg agtctctttg  63660
gtctaaaagg gaagggaaga gttgaggttc tccgatggac ataatccttg agctgagttg  63720
gccaagtgaa gaagaaccaa gaacagccca ggcagtgcag aaagcctgtg caaagccagg  63780
agtgggagag gcatagagtc agggaggctg acctaggcgt tcagtatgac agcaatcctg  63840
gataagactc agaacctggg gtgactcatt ccctcccact gtgatattca tacgtgtcct  63900
gtgtatccgt tttctcatgc ctgactcatg ccttagcagt atttttgagt tggattgccc  63960
atttttaggt ttaacccctg tgctagctag tattactact gctgtgatga aacaccataa  64020
ccaaagcaac tttgggaaga aaggattcat ttggcttatg cttccacatc actgttcatc  64080
actgaaggaa gtcaggatag gtattcaaac aggacaggaa gttggaggca ggagctgatg  64140
cagaggccat ggaagggtgc tgcctaccgg cttgttcccc atggcttcct tagcctgctt  64200
tcttagagaa tgcaggacca ccatcccagg gttggaacca cccacaatgg gctggctctc  64260
ccccatcaat cattagttaa gaacatgccc tataggcttg cctacagcct gatcttatgg  64320
aggcattttc cttttttttt tttttttttt tgttttttgt tttttgtttt ttgcttttat  64380
tttattagat attttcttta tttacatttc aaatgctatc ctgtaagttt cctatacctt  64440
ccccccgccc tgctccccta cccacccact cccacttctt ggccctggtg ttcccctgta  64500
ctggggcata taaagtttgc aagacctagg ggcctctctt cccaatgatg gccaactagg  64560
ccatcttctt ctacatatgc agctagagac acgagctccg gggtactggg ttagttcata  64620
ttgttgttcc acctataggg ttgcagaccc cttcagctcc ttggatactt tttctagctc  64680
ctccattggg ggccctgtgt tccatccaaa agatgacggt gagcacccac ttctgtattt  64740
gtcaggcact ggcatagcct catatgagac agctatatca gggtcccttc agcaaaatct  64800
tgctggcata tgcaatagtg tctgggtttg gtggctgatt atgggatgga tccccaggtt  64860
gggtagtctc tggatagtcc atccttttgt cttagtggag gctaagacga atttcttaat  64920
gaggctccct cctctcaaat ggctctagct tgtgtcaagt tgacataaga ctagccagca  64980
catctccctt agggactctg ttcttttata agtcacatac agaagtgcta atgcatagta  65040
tatatataat atgctgtagt agaggcatga cagatacatt ggtgatgtaa cagcatcttg  65100
gttgatgata ttcctgggga ggaaatagaa aggtcgtccc agagtggagg tgaaggttct  65160
ggagaaggta gcatttgaat tggtcttgaa agggctcacc acaaaagatg gtggagaggc  65220
aactagtcta gtttattctg aataactctg ttcctgccat ctgtgtgtcc tctctggttg  65280
ctatgacact tgctgaaaga atcagtactt acactggatt aaagcattaa ctttaaatgc  65340
ctgctaatct gaaggggagg agatgagcat tgttctcacc agaagaacag ttaggttttc  65400
ataagatccc tggacagtca tttacatttt attctctatg aattgcctac tggtggtctc  65460
attttttaat tttggctatc ttatttttag aaatacataa taaatattaa aaccttagta  65520
atagataaac aaatattttc tcccagtctg acactcgatt tttaaattag ctcatggtat  65580
ctcttatcat tcataaattt atatttaagt ttatatttaa gtcttagatc tgcccctctt  65640
ttgttctgtc agttctgtgt ttactatctt gcttagaaag gcccacttcg ttctgagtta  65700
```

ttaaaatgtc agctaatatt ttcttcttct aacttaaact catttttttct gtgctttata 65760 ttgttatttt agaggatgac ctgagctagg gatgtaactg ttttcttttg taattgttat 65820
cctcgttcta atctgtgaat ataattattt atatgtgtgt actaattttc taaaaccata 65880
cttagggacc catcatctcc ctgtgacttg agtgatcatc tttattgtag cctatacatg 65940
tcagcctatg caatcccccct cacctactat ctgttcattc ccatagatag caatactttt 66000
tgaagtgtta tccttgtaaa catttttttt aaatgtttgt atatcatttc tcttctagat 66060
aaactttaga ataattgtgt cattttgtaa aacttacgat aagattttca ttggacttgc 66120
tttggataaa tacacttgcg tgagaggaac ttacattttt atagtatcaa actttcccat 66180
ttaagacatg gcatctttat ttcagccttc atttatgtcc tttagccgac atgtcgcatt 66240
tgcctacttc ttgttcagtt agtctgggta ttttgtaact tttactagtc cattatgagt 66300
gtgcctgttc cgtgacattt tctagttggt tatttatttg ggaaattatg tgtgtttgtt 66360
tgcctgggtg ggtggttttt tgagacaggg ttgcagaaac tctgtaaggc ctgagctaac 66420
cacggtgcag tccagacgat tcttaaactc ttgttaattt tcctgtctcg gtctcctgag 66480
cactagagtg atgagtgtga gccccacatc tgcatcctaa tgtgttaccg cttactaaag 66540
gcaggctttg tttttttata ttgattcttg agtaactaga ttatttgtaa tattcttttt 66600
cctgcttctg taacactctt tttcttgttg ctatcgttac ttatggtatt cttactcaaa 66660
cagaaacccc ttatatcata ctttagcatc ctaaatcatt tccaccaatg tgcttggaac 66720
cactctgtac tttggcgagc acagtctgag aaacttccct ctataggccg ccctgggtga 66780
cctctgcagt ccgcacatgc ccagctgagt tcttgcccat tcccatcatc tggatttaac 66840
tctttgtttg cacttccacc agctctacaa gatctgtcaa gcacagatca agcatagatt 66900
ccttcctagg tcttggtcct ggacctataa gacacccctt cctttcttct gacaaaggga 66960
cagagagtgc ttggtcttga ctttaccatc tgtccaacaa gaaccgagct gcttggtatt 67020
tttcaccagc cctaaagtct ttgactcaaa cctgtgttgt ccttctatat cctcttctag 67080
agactctctt tgttggatgg ggcctcagag ttggaaagac atgcagtttg gagggagggt 67140
ggccttctta agagttccag caaagcagca gcattagggt acaggtgtag gcaaatactt 67200
ctcagccatt tagcaagtgt cgctgagcta ttagacatga gcacagagaa taaacaaaca 67260
ctcagggctg gagagatggc tcagtggtta ggaacgatgg ctgttctcct aaaagaccag 67320
agtctatttc ccattgtcca tgtctactgg ctcacaacca actgtcacac tagttccagg 67380
atataggatg ccttttcctg gtcccaaccc atacctgcac atgcatgtac atatgtatac 67440
actcaacaga cacacagaca tactacatac acataaatac acataaataa aaatgataaa 67500
aatcactttt ttaaagttag cacagccctc aaaagctcag tccaattgag agaacagaga 67560
gttaaaaatc gtgtggcctg ggaacacacc taagggggag gcagggtctt cccagagcag 67620
ttgggaaaga ggtcacaaca gataagaatt cataaagaaa cacagtggtg actcaaaatg 67680
gagcccggaa gcaaggggtt atacggtctg ggagggggca gatgggtgtt gatgctgggc 67740
cggagcccct ggttgttcag tgtgatgtgg ccttccctcc agtggtaata gccctgctat 67800
gtatgagtgg gtacctcatc tggaggaact ggaagcggaa gaacaccaag agcatgaatt 67860
tcgacaaccc agtgtacagg aaaacgacag aagaggaaga ggaagatgag cttcacatag 67920
ggaggacagc tcagattggc cacgtctacc ccgcagtaag tactccacag cgccttcccg 67980
ccctccttcc ctctcccccct ccctccttcc ttccttcctt ccttccttcc ttccttcctt 68040
ccacgttatc aggaacctcc tgcataccag gcactgtttt ggctctggga gaacacagcc 68100

```
atgctgaagc aggcggtggg aggagcagag tgtcaggatt ccttttacct gcagggtctc  68160
cctggcagtt aagcagccaa atgactttct gcagaagggt aactggctga attccaacaa  68220
gctctgaatg ccagttaaat gccaaacccc acattagaca tcagcttccc aagtcgttgc  68280
tggggtgtta gagatgctca gtgccatggg gtggaagctg aagaatctat caccctagga  68340
cgccttccta ggcttgcttt cttctcccac agtttcctgg gcctctccat ccacaatccc  68400
catacctttt gcttagcagt taggccacta gactgtgggg tccctgaggg caggctctga  68460
tgtggtctct ttgcctgggc ttggcacagc acagctggct ttaacaaatg ctgaaggatg  68520
gatggtgtag aagcacagcc atggggctgc tggtttgtct ggggatcaag tgcataggat  68580
gactcccagt aacacacgag ctgtgtcttt attaaaaaaa aatagtaatt ttcaggtagg  68640
gaagaataga gctgacattc caaagagaat catgtggaaa ggctaagagg catgagaggg  68700
cgtggcttgt tggggagcga ggattatgaa gcggttagaa caggtgtcgt tgttgcacag  68760
cagagtcagg gggctgagta tgacctcaga ggtcatccag tccatccccc tgtcaggcaa  68820
tcagcaacta tgatcgccca ctgtgggcag agccctgtct tggggagacc agagacctgg  68880
aagacccagc ccctgccctc aaggagcttt ttgtcttgcc gggagaacca aggtcacagc  68940
ttcaccaact cccgaagaac cctctttccg agctgcctgt cgtcaagtgc aaggtagggc  69000
agtgccactc tgagcctgag ggctggcga gtgagggcct taaacctagg cagctataga  69060
aaatcctagc aggctttctg attttagaag gcttgatatc gggatagagg aaacggcatg  69120
ttactgaata atgttactga atgcgtggca gacaaactgc tcttgaagca aactgtttgt  69180
aaaggagaga tgtatgaaac aaagttgttc agtgctgtga gggtcagaag atggtcctga  69240
ggctccgtca ccgtggccag tgcaggcaaa cagaatttta gcgatcagag gtcacaggaa  69300
gcctagaact tggagggaga agatggctct gtcccactgt tcccacggcc ctgcagtctt  69360
gtctgcttac ctctgctagt gaggtgagag tggaaaccct agtctctgct tcctgaggtt  69420
aaaccgttta ggagcatctt gtaaattaca aatcagtcta ggctaaagaa tcatcatttc  69480
cagggaagga aatgatgcag ggaacttaac tctgattaat aaggcagatc tgagttcaag  69540
gcctgctggt ctacagaggg agtttcagga ccaggataca cagagaaacc ctgtcctgtg  69600
tgataagctc ctgctagttg cagagaaatg gagtaagcaa aagtacattt ggcaagcaca  69660
gtgtgtcaga cattgctttc tgtgtgtcat gtctttctca tttagtcttc acagttacct  69720
ttggaggtga tagtattagt ttcatttaca gttgagaaaa ctgagagcca caggatttaa  69780
ataacttccc cgagatccta ggcagaaagt ggcagaacca ggagtaactc caggcagtgc  69840
acagaggccc gagttccccc cactctgtca tggggtacat gtcctccaag ctctggaaat  69900
cagaattccc aacctccaat cttctgtcct tttctcctgt agctttgcca tcactactag  69960
gggcctatct aaaaaaaggc aatgggtttc ttttgttttg ttttgttttg tttttgtttt  70020
tgtttttgtc atatgtagca tgtccagagt tggaaaatgc ttactttatg ctggttaggt  70080
ttcgctagac tacttaagac accatacttg ctagctagca tgtcagaact ccagatacat  70140
tttttcattg ggtttctcac ccatcctgtg aagtagatcc aagcctcact gacagctgat  70200
gaaactaagg cttagaaaag cgcagtgagg ccaccctcaa atcatacagt ctgagggggt  70260
aatgcagctc tcagcaccat gtaaggaagg cggcaggaaa ggggaaagtg gcaggcaggg  70320
ttcactcaca atgagctaag gaacgtggga tgtgcatcct agaaaagggg atcgcttgtt  70380
caaaaaataa gttttggggc tttcctgccc agaactccga gactaatgca gaccagggag  70440
catgagaaga tgtcaatcac acaagtatag gaaagaattt caccctaaag ggaacagagc  70500
```

```
cataggttag ccatttgagg cagaagagag ttgagcatcc agtaactggg agtaagggac  70560
gggggggggg gggggggggg ggaggggaag agagggatgg aatagaatca ccggtattgc  70620
tttccagtgc tcctttatca gttaagaggg gcacagcatg gtacccacct aattgtgatt  70680
tgtattctgg ggacaggtgg ctaatagctc aagatttaac atttgacagt taaccctctt  70740
taagttcacc caacttaaac tcctgtgagg aaccaaggtt aggtctttgc tgcctttctt  70800
tgtgaaagga cagaacagaa tggtggggga aagctacact tgtagatctg cacagacgcg  70860
ggatcaaact tgagttcagc tgtttgctgt gtgacccaga gcgccatgta gcctcagttt  70920
tctcacctct gaaataagtc agataatctt atcatgggga gtgaggatct tgtgagctaa  70980
tgtctgtaaa ggaatagtac atctgatact tttgttgcca ttcagtaaga ttgcctctta  71040
tagatctaac gacgatttct ttggtctgtt tccccagcga gtggcattaa gtcttgaaga  71100
tgatggactg ccctgaggat gggcccaccc acttcgtgcc tcatggagtt cagtcctatg  71160
cactactctc tctggatggt gtgtgattgg atgagtgcca tttctatata tgggtctgtg  71220
tgagtgtgtg tgtgtgtgtg tgtgagtgtg tgtgtgtgtg tgtgtgtgtg tgtgtgtgtg  71280
tgtgtgtgtg tgtatgtgac ttttttttaaa tttatgttgc ggaaaggtaa ccacaaagtt  71340
atgatgaact gcaaacatcc aaaggatgtg aaagtttttta tatgtataat gttttataca  71400
ctttttaact ggttgcacta cccgtgaaga attcatggga cagccactgc tgagtgacta  71460
acatgatgca cataaccaaa cggggccaat ggtacaaact tcactcatca tttgaataca  71520
gtatttacag aggatgtttg agttgagagc ttttttaggt ttgaggggct tgattttttt  71580
gtaaataaaa ttatgctttg tggctatcca tcaacataag tataaaaaga aagaacgctt  71640
caaccccctt ccccatttag attatttatt aacatatttc gaaagtaagg ttagctctat  71700
aaataattta gagaggtgag agtatttatt tttggtatgg ctggctcact gcacagactc  71760
tgtgtttatg tgtgtgtgtc tgtgtgagag aagaaaaatc tgtagagaag aggcacgctt  71820
atgactattg ttcaaataca taaaaacagt tattttaaaa cagtccacaa gaggggtgtc  71880
tagttttcag agacacttca gaaactttgc tcagaaaaca gatgctacag tttgtgcagg  71940
catgcggtag gaaaggtaga tcacctctgg ctactcctga ggccctgctg agccagcaaa  72000
atgctttcca gttcctcttt ggctctcacg atgcccacct aggctttctg gccagtgtac  72060
tgaacagtgc tacaagccct caggagctca agatagcaga gtccttcttt caaagcccag  72120
cttagtgagg acttgggtca acttcagtaa gcttcctctg aagcaactga aggccgagcc  72180
tttagagcaa ccattgtcaa cctttgtggg tcgcctaaga gcatcgcaaa ccagatattt  72240
acattatgat tcataacagt gacaatcaca gttatgaggt agaaaggaaa gggattttat  72300
ggttgggggt tagtccaaca agagggacag tgttaatgct tctgaagcat caggaaggtt  72360
gaaagccact gctctagagc caagtgagtg catgtctagg gttcccatgt ttacagtaag  72420
gaccggctca ggcactgacc ctctgagtca cgtgaatgag gacgaagaat ttggaatagg  72480
tttggttaca tctatttctc atccccttat tttccaccat ttaaaaataa taaacatgtt  72540
tcttaccacc gtatgttcat atggataaga ctaagtccaa aaaggtgact acatccaaat  72600
ttatatttcg gggaaatacc atgagataat tatagcatac tgggcatgtg tccacacacg  72660
gattggtttc actgctttat aaataaaagg aacaactctg ggtatttgta tagaattttc  72720
ttcatatgta acatctttcc atttcctgag ccttgggggt ggggtgggag aatgccactt  72780
gctgtctgtg aagtccactg ttggaaacat aattccatag tcccagaagg aattcagtcc  72840
ccaccaactt actctttcaa agtgtggtct tcccgcgact ctgcagctct gcagttcact  72900
```

```
ccagctgaac gaccagggac aagtacaaca caggagtttg gcttaagtgg cagcagacta  72960
atatctaaag ttgacataac tgaaatctga catttgaggc atatgtctcc gcgtccccac  73020
acaccggctt gagtggctca cctgcttgat gtcctttcaa cttccgggga gaccgtctgg  73080
agacctgtca tcctgtcatc ctgttcctag gagcttgctc tatgtcactc atgttttcct  73140
aacctttaaa aaatggctgt gttccaagcc tggccattat gtctgacaat gcacgtgttg  73200
atggtcttga gatatacagt gactaaatgc agctgacccc tgacccattc caaacagtct  73260
caaggacagg cagctgagtc ccctgcagct cgcctgtcac tgttcatcca ggaatggaga  73320
ggagaaatca agtttactaa agaaaaaggt tagaagtgaa atcatcaaaa tttacacaag  73380
ataggcaggg tttttccctt taatctgcct ccaaggaaac tgaagcagtg atagtgtata  73440
gtttctgaac aaacgttcat agcctagcct tcacaacaag gctgaaacat accgtctagg  73500
gtttccgaaa gatgaaagaa ttcatatcag aaataccatg tttcctgaat gtgccacagc  73560
tgcagtctaa aagcagccta cagtaaacag atgggcaaat ccagggacgg ccggagagcg  73620
gaagcactct gagggaccag accgacctcc ttctatcctt ggaaactttt tgagcctcat  73680
tctgaggtgt aattcagact tctgttgcct ttcgcctctg cctatgtatc cacagccaat  73740
aacagctgaa aggaaactca gtaataaacc aaaaggacag aaaattcaac aaacgttact  73800
tattaaaacg aagccaaccc cttccttctc tagaagacaa ctctgagcag cctgaacaag  73860
gtctcagacc tgcatcctct ccacagctat ctgcccagtg gattgaaggc actaacagaa  73920
acgactttcc tgaaacaaga aactacagct ttgtttactc ttcagaatgt gtgtatgtgt  73980
gtgcacagag ggacaggatg agacggcttc tgacaaggag taagaagaat gagacaggat  74040
ttaaactgat gtcagtgaac actgttgaag ccctccagtt atcctcatgt cttagtaaca  74100
tactcagagt attcactcgc tgctgtgtgc caggctttgc agacattgca ggtcaattca  74160
acagttttca ccctttccaa actcacagca gtacatatgg atacaaaaag aaaaaaaaat  74220
tttcccatag atttcaccta gactactccc aaggcacaac aaaagagatg ggccatttta  74280
cctgaagagg tggaaatagg tctacatagg aatgacccaa agcaatgtct taaaacttaa  74340
aaagtggtgt tcaggctgct tctatgagaa gaggctgggc tcagactggg agtgaatcag  74400
cagcaggaat ttcaaggaaa acatggagtt ccttacacct ggaataaaga actttagcag  74460
ggttggcaag atgtgaaact ggatggaaag acaagttcaa cacaagcact ttataaaata  74520
gtctgatgta agtaagcaga catttgtttg gtcgtcggtt cctgtgtgca aggcatcatg  74580
ggaaactccc tgccagcact tggcaggcat tattccacct caagctttcc agagaccaca  74640
gggaaatgac tgttttcttt atttgagcca gaggttttga tatggttcct gaaggctaac  74700
agaagggcgg tgggcttgtc aacagaagca cgccatgttg ccgagcacct gtgaggtcct  74760
cacgtgggag gaagagaaca aggtggttaa gatagagaat ctggagaggg taccccaatc  74820
acactacagt cgggtgctac tgggtggagg agaaaaccat cctaacccca cagcactgca  74880
aagacgctcc tgtcccgcca cactcccacc atcacgaaca tcagtaagtc agcagtttca  74940
gattctgcca tttccttccc cataaaagca tgaagatagg gagtcggtgt ccttacgctt  75000
tatttttagg gtatttggga gtttccagga tgtgaagaag ttaggtggag gaaattacgg  75060
cttcaatttt tttcagttaa ctacaggacg cttcattcag gccgggcacc atgtgcacag  75120
tcttaagaag cagcaggaac tgcatttgca aacacgtgtt gtaaaaaatt aattttaaaa  75180
aagctacctg tataaatata aatatatata tttaaagaca aggttttgat acttttttt  75240
taaaaaacaa aaactacaag agaagactgt acaaaccacg ggcttttaaa atagcatttt  75300
```

```
gctctctaca agctgttaat gtcaggggtg aggggtgagg gactggtttg caaacacact  75360

atccaaatgg atttgcttgt tttgtcaagc caccctccaa attaccatat ttggtgtaat  75420

agtagggcat gtaaagttat tgggtcccat taaccatttc tgctcttgtc atgtcattcc  75480

gggttccgtt agctcccgta ctcggcaatc cagcttcttc cagaggcaga ggggctgaag  75540

gaagtgtgct ccatttcact agctgtactg acatcatcca catgtggaca tttgtaatat  75600

cagtacacta tttctagaga gattaaattc attttttaaa atctgttttg tttccttgtg  75660

gtgatttgat ggtggtgggg aggtgtgagc tctcacatgc taaccccctc atgtatacca  75720

aaggttttgc acaaacatct cgatcttagc agtaagtact cagtattatc cactcccgtt  75780

ttataaagac atgggtgaag ttacagctca aagccacaga gttctttttg gtagtcctaa  75840

agaacaacag actattctct gcctagattt tcttcctgct tgttaagaac tcaatttagg  75900

tagtgtctct cccaggaagt aacgtcttgt ctgtctgggt tagaaaactc cgtatttcca  75960

ttatgacttt tgttcacgtg cagcccagtc tttctgagct gccacttttc tcatgcccct  76020

gaggtgactt taccaaggcc tccttgtaga cactccagtc cttttcttcc ttgacctagg  76080

agcagtattt tatactaggc cactcttcct ggaatactct tattttggct tctatggctc  76140

catatgcctg gtttctccct tacagctttg gccacagctt agtctccttt gcctactgtg  76200

ttagtcaggg ttctctagag tcagagaact tatgcctcgt ctctatatag taagcggatt  76260

ggtttgtctg tagtccaact ccaaggattt agcagttgct cagtcccaca aggcaagcag  76320

aagaagaatg tccttatgta ggtctccaca ttaaaggtgt gtaccaccac acctggatct  76380

aggggaagaa gagtgaatct tccttcttcc aatgtcctta tgtaggtctc cagcagaagg  76440

tgtggcctag attaaaggtg tgtaccacca tgcctggatc taagacttgc tttgtcgcag  76500

atgaccttga actcagatct ccttgcctta atctcctggg attcatagcc actatgcctc  76560

atgatctcca tgccaagacc aggtcggaaa cttgtatctc c                      76601
```

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32

```
cctgttctaa ccgcttca                                                    18
```

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33

```
cgacacctgt tctaaccg                                                    18
```

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34

```
aacaacgaca cctgttct                                                    18
```

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
tgtgcaacaa cgacacct 18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
tctgctgtgc aacaacga 18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
ctgactctgc tgtgcaac 18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38 gcccctgac tctgctgt 18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
actcagcccc ctgactct 18

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
gtcatactca gcccctg 18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
ctgaggtcat actcagcc 18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
gacctctgag gtcatact 18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
tggactggat gacctctg 18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
ggctcagagt ggcactgc 18

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
cctcaggctc agagtggc 18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
cagcccctca ggctcaga 18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
ctcgccagcc cctcaggc 18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
cctcactcgc cagcccct 18

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 49
aaggccctca ctcgccag 18

<210> SEQ ID NO 50
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 50
ggtttaaggc cctcactc 18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
gcctaggttt aaggccct 18

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
tagctgccta ggtttaag 18

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
ttctatagct gcctaggt 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide -continued

```
<400> SEQUENCE: 54

ggattttcta tagctgcc                                                     18


<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55

tgctaggatt ttctatag                                                     18


<210> SEQ ID NO 56
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 56

aagcctgcta ggattttc                                                     18


<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 57

tcagaaagcc tgctagga                                                     18
```

ANTISENSE COMPOUNDS TARGETING APOLIPOPROTEIN E RECEPTOR 2

SEQUENCE LISTING

The present application is being filed along with a Sequence Listing in electronic format. The Sequence Listing is provided as a file entitled BIOL0256USASEQ_ST25.txt, created Dec. 1, 2016, which is 216 Kb in size. The information in the electronic format of the sequence listing is incorporated herein by reference in its entirety.

BACKGROUND OF THE INVENTION

Apolipoprotein E receptor 2 (APOER2 or LRP8) is a post-synaptic transmembrane protein that mediates a signaling cascade initiated by the binding of ligands including ApoE and Reelin. APOER2 has been found to protect against loss of coricospinoneurons during normal aging. Following ligand binding, APOER2 interacts with PSD-95, a post-synaptic density protein important for synapse formation and function. This interaction activates the src-family of kinases, ultimately leading to phosphorylation and activation of NMDA receptors. The interaction between PSD95 and APOER2 requires 59 amino acids that are encoded by the alternatively spliced exon 19. APOER2 protein isoforms that lack exon 19 act as dominant negative inhibitors and cause defects in long-term memory storage and spatial learning. The antagonizing activities of the two alternatively spliced forms of APOER2 may suggest a regulatory role in signaling. Given the role of the active form of APOER2 in memory and learning, any disruption in the alternative splicing of this transcript could disrupt signaling and lead to learning and memory defects similar to those seen in Alzheimer's Disease. Indeed, Reelin signaling through these receptors has been shown to be required for critical processes in the developing and adult brain including neuronal migration, dendritic development and synaptic plasticity.

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Certain antisense compounds have been described previously. See, for example, United States Patent Application Publication No. 2014/0114057 and published International Patent Application No. WO 2008/049085, which are hereby incorporated by reference herein in their entirety.

SUMMARY OF THE INVENTION

In certain embodiments, the present invention provides compounds comprising oligonucleotides. In certain embodiments, such oligonucleotides are complementary to an LRP8 transcript. In certain such embodiments, the oligonucleotide is complementary to a target region of the LRP8 transcript comprising exon 19 or the intronic sequence upstream or downstream of exon 19. In certain embodiments, oligonucleotides described herein increase the ratio of LRP8 mRNA having exon 19 compared to LRP8 mRNA without exon 9.

The present disclosure provides the following non-limiting numbered embodiments:

Embodiment 1. A compound comprising a modified oligonucleotide consisting of 8 to 30 linked nucleosides and having a nucleobase sequence comprising a complementary region comprising at least 8 contiguous nucleobases complementary to a target region of equal length of an LRP8 transcript.

Embodiment 2. The compound of embodiment 1, wherein the complementary region of the modified oligonucleotide is 100% complementary to the target region.

Embodiment 3. The compound of embodiment 1 or 2, the complementary region of the modified oligonucleotide comprises at least 10 contiguous nucleobases.

Embodiment 4. The compound of embodiment 1 or 2, the complementary region of the modified oligonucleotide comprises at least 12 contiguous nucleobases.

Embodiment 5. The compound of embodiment 1 or 2, the complementary region of the modified oligonucleotide comprises at least 14 contiguous nucleobases.

Embodiment 6. The compound of embodiment 1 or 2, the complementary region of the modified oligonucleotide comprises at least 15 contiguous nucleobases.

Embodiment 7. The compound of embodiment 1 or 2, the complementary region of the modified oligonucleotide comprises at least 16 contiguous nucleobases.

Embodiment 8. The compound of embodiment 1 or 2, the complementary region of the modified oligonucleotide comprises at least 17 contiguous nucleobases.

Embodiment 9. The compound of embodiment 1 or 2, the complementary region of the modified oligonucleotide comprises at least 18 contiguous nucleobases.

Embodiment 10. The compound of any of embodiments 1-9, wherein the nucleobase sequence of the oligonucleotide is at least 80% complementary to an equal-length region of the LRP8 transcript, as measured over the entire length of the oligonucleotide.

Embodiment 11. The compound of any of embodiments 1-9, wherein the nucleobase sequence of the oligonucleotide is at least 90% complementary to an equal-length region of the LRP8 transcript, as measured over the entire length of the oligonucleotide.

Embodiment 12. The compound of any of embodiments 1-9, wherein the nucleobase sequence of the oligonucleotide is 100% complementary to an equal-length region of the LRP8 transcript, as measured over the entire length of the oligonucleotide.

Embodiment 13. The compound of any of embodiments 1-12, wherein the target region is within exon 19 of the LRP8 transcript.

Embodiment 14. The compound of any of embodiments 1-12, wherein the target region is within the intron upstream of exon 19 of the LRP8 transcript.

Embodiment 15. The compound of any of embodiments 1-12, wherein the target region is within the intron downstream of exon 19 of the LRP8 transcript.

Embodiment 16. The compound of any of embodiments 1-12, wherein the target region is a portion of the intronic splicing silencer upstream of the 3' splice site of exon 19 of the LRP8 transcript.

Embodiment 17. The compound of any of embodiments 1-12, wherein the target region is a portion of the intronic splicing silencer downstream of the 5' splice site of exon 19 of the LRP8 transcript.

Embodiment 18. The compound of any of embodiments 1-9, wherein the target region is within nucleobase 78901 and nucleobase 79258 of SEQ ID NO.: 1.

Embodiment 19. The compound of any of embodiments 1-9, wherein the target region is within nucleobase 79176 and nucleobase 79208 of SEQ ID NO.: 1.

Embodiment 20. The compound of any of embodiments 1-9, wherein the target region is within nucleobase 79176 and nucleobase 79193 of SEQ ID NO.: 1.

Embodiment 21. The compound of any of embodiments 1-9, wherein the target region is within nucleobase 79181 and nucleobase 79198 of SEQ ID NO.: 1.

Embodiment 22. The compound of any of embodiments 1-9, wherein the target region is within nucleobase 79186 and nucleobase 79203 of SEQ ID NO.: 1.

Embodiment 23. The compound of any of embodiments 1-9, wherein the target region is within nucleobase 79191 and nucleobase 79208 of SEQ ID NO.: 1.

Embodiment 24. The compound of any of embodiments 1-23, wherein the antisense oligonucleotide has a nucleobase sequence comprising at least 8 contiguous nucleobases of any of the nucleobase sequences of SEQ ID NOs: 3-30, or 32-57.

Embodiment 25. The compound of any of embodiments 1-23, wherein the antisense oligonucleotide has a nucleobase sequence comprising at least 10 contiguous nucleobases of any of the nucleobase sequences of SEQ ID NOs: 3-30, or 32-57.

Embodiment 26. The compound of any of embodiments 1-23, wherein the antisense oligonucleotide has a nucleobase sequence comprising at least 12 contiguous nucleobases of any of the nucleobase sequences of SEQ ID NOs: 3-30, or 32-57.

Embodiment 27. The compound of any of embodiments 1-23, wherein the antisense oligonucleotide has a nucleobase sequence comprising at least 14 contiguous nucleobases of any of the nucleobase sequences of SEQ ID NOs: 3-30, or 32-57.

Embodiment 28. The compound of any of embodiments 1-23, wherein the antisense oligonucleotide has a nucleobase sequence comprising at least 16 contiguous nucleobases of any of the nucleobase sequences of SEQ ID NOs: 3-30, or 32-57.

Embodiment 29. The compound of any of embodiments 1-23, wherein the antisense oligonucleotide has a nucleobase sequence consisting of the nucleobase sequence of any of the nucleobase sequences of SEQ ID NOs: 3-30, or 32-57.

Embodiment 30. The compound of any of embodiments 1-23, wherein the antisense oligonucleotide has a nucleobase sequence comprising the nucleobase sequence of SEQ ID NO: 17.

Embodiment 31. The compound of any of embodiments 1-23, wherein the antisense oligonucleotide has a nucleobase sequence comprising the nucleobase sequence of SEQ ID NO: 18.

Embodiment 32. The compound of any of embodiments 1-23, wherein the antisense oligonucleotide has a nucleobase sequence comprising the nucleobase sequence of SEQ ID NO: 19.

Embodiment 33. The compound of any of embodiments 1-23, wherein the antisense oligonucleotide has a nucleobase sequence comprising the nucleobase sequence of SEQ ID NO: 20.

Embodiment 34. The compound of any of embodiments 1-23, wherein the antisense oligonucleotide has a nucleobase sequence consisting of the nucleobase sequence of SEQ ID NO: 17.

Embodiment 35. The compound of any of embodiments 1-23, wherein the antisense oligonucleotide has a nucleobase sequence consisting of the nucleobase sequence of SEQ ID NO: 18.

Embodiment 36. The compound of any of embodiments 1-23, wherein the antisense oligonucleotide has a nucleobase sequence consisting of the nucleobase sequence of SEQ ID NO: 19.

Embodiment 37. The compound of any of embodiments 1-23, wherein the antisense oligonucleotide has a nucleobase sequence consisting of the nucleobase sequence of SEQ ID NO: 20.

Embodiment 38. The compound of any of embodiments 1-23, wherein the antisense oligonucleotide has a nucleobase sequence comprising at least an 8 nucleobase portion of any one of SEQ ID NOs: 17, 18, 19, or 20.

Embodiment 39. The compound of any of embodiments 1-38, wherein the modified oligonucleotide comprises at least one modified nucleoside.

Embodiment 40. The compound of embodiment 39, wherein at least one modified nucleoside comprises a modified sugar moiety.

Embodiment 41. The compound of embodiment 40, wherein at least one modified sugar moiety is a 2'-substituted sugar moiety.

Embodiment 42. The compound of embodiment 41, wherein the 2'-substitutent of at least one 2'-substituted sugar moiety is selected from among: 2'-OMe, 2'-F, and 2'-MOE.

Embodiment 43. The compound of embodiment 42, wherein the 2'-substituent of at least one 2'-substituted sugar moiety is a 2'-MOE.

Embodiment 44. The compound of any of embodiments 40-43, wherein at least one modified sugar moiety is a bicyclic sugar moiety.

Embodiment 45. The compound of embodiment 44, wherein at least one bicyclic sugar moiety is LNA or cEt.

Embodiment 46. The compound of any of embodiments 40-45, wherein at least one sugar moiety is a sugar surrogate.

Embodiment 47. The compound of embodiment 46, wherein at least one sugar surrogate is a morpholino.

Embodiment 48. The compound of embodiment 46, wherein at least one sugar surrogate is a modified morpholino.

Embodiment 49. The compound of any of embodiment 1-48, wherein the modified oligonucleotide comprises at least 5 modified nucleosides, each independently comprising a modified sugar moiety.

Embodiment 50. The compound of embodiment 49, wherein the modified oligonucleotide comprises at least 10 modified nucleosides, each independently comprising a modified sugar moiety.

Embodiment 51. The compound of embodiment 49, wherein the modified oligonucleotide comprises at least 15 modified nucleosides, each independently comprising a modified sugar moiety.

Embodiment 52. The compound of any of embodiments 49-51, wherein the modified oligonucleotide comprises one or more 2'-deoxynucleoside.

Embodiment 53. The compound of embodiment 49, wherein each nucleoside of the modified oligonucleotide is a modified nucleoside, each independently comprising a modified sugar moiety Embodiment 54. The compound of any of embodiments 1-53, wherein the modified oligonucleotide comprises at least two modified nucleosides comprising modified sugar moieties that are the same as one another.

Embodiment 55. The compound of any of embodiments 1-54, wherein the modified oligonucleotide comprises at least two modified nucleosides comprising modified sugar moieties that are different from one another.

Embodiment 56. The compound of any of embodiments 1-55, wherein the modified oligonucleotide comprises a modified region of at least 5 contiguous modified nucleosides.

Embodiment 57. The compound of embodiment 56, wherein the modified oligonucleotide comprises a modified region of at least 10 contiguous modified nucleosides.

Embodiment 58. The compound of embodiment 56, wherein the modified oligonucleotide comprises a modified region of at least 15 contiguous modified nucleosides.

Embodiment 59. The compound of embodiment 56, wherein the modified oligonucleotide comprises a modified region of at least 20 contiguous modified nucleosides.

Embodiment 60. The compound of any of embodiments 55-59, wherein each modified nucleoside of the modified region has a modified sugar moiety independently selected from among: 2'-F, 2'-OMe, 2'-MOE, cEt, LNA, morpholino, and modified morpholino.

Embodiment 61. The compound of any of embodiments 56-60, wherein the modified nucleosides of the modified region each comprise the same modification as one another.

Embodiment 62. The compound of embodiment 61, wherein the modified nucleosides of the modified region each comprise the same 2'-substituted sugar moiety.

Embodiment 63. The compound of embodiment 61, wherein the 2'-substituted sugar moiety of the modified nucleosides of the region of modified nucleosides is selected from 2'-F, 2'-OMe, and 2'-MOE.

Embodiment 64. The compound of embodiment 62, wherein the 2'-substituted sugar moiety of the modified nucleosides of the region of modified nucleosides is 2'-MOE.

Embodiment 65. The compound of embodiment 61, wherein the modified nucleosides of the region of modified nucleosides each comprise the same bicyclic sugar moiety.

Embodiment 66. The compound of embodiment 65, wherein the bicyclic sugar moiety of the modified nucleosides of the region of modified nucleosides is selected from LNA and cEt.

Embodiment 67. The compound of embodiment 61, wherein the modified nucleosides of the region of modified nucleosides each comprises a sugar surrogate.

Embodiment 68. The compound of embodiment 67, wherein the sugar surrogate of the modified nucleosides of the region of modified nucleosides is a morpholino.

Embodiment 69. The compound of embodiment 67, wherein the sugar surrogate of the modified nucleosides of the region of modified nucleosides is a modified morpholino.

Embodiment 70. The compound of any of embodiments 1-69, wherein the modified nucleotide comprises no more than 4 contiguous naturally occurring nucleosides.

Embodiment 71. The compound of any of embodiments 1-69, wherein each nucleoside of the modified oligonucleotide is a modified nucleoside.

Embodiment 72. The compound of embodiment 71 wherein each modified nucleoside comprises a modified sugar moiety.

Embodiment 73. The compound of embodiment 72, wherein the modified nucleosides of the modified oligonucleotide comprise the same modification as one another.

Embodiment 74. The compound of embodiment 73, wherein the modified nucleosides of the modified oligonucleotide each comprise the same 2'-substituted sugar moiety.

Embodiment 75. The compound of embodiment 74, wherein the 2'-substituted sugar moiety of the modified oligonucleotide is selected from 2'-F, 2'-OMe, and 2'-MOE.

Embodiment 76. The compound of embodiment 75, wherein the 2'-substituted sugar moiety of the modified oligonucleotide is 2'-MOE.

Embodiment 77. The compound of embodiment 73, wherein the modified nucleosides of the modified oligonucleotide each comprise the same bicyclic sugar moiety.

Embodiment 78. The compound of embodiment 77, wherein the bicyclic sugar moiety of the modified oligonucleotide is selected from LNA and cEt.

Embodiment 79. The compound of embodiment 73, wherein the modified nucleosides of the modified oligonucleotide each comprises a sugar surrogate.

Embodiment 80. The compound of embodiment 79, wherein the sugar surrogate of the modified oligonucleotide is a morpholino.

Embodiment 81. The compound of embodiment 79, wherein the sugar surrogate of the modified oligonucleotide is a modified morpholino.

Embodiment 82. The compound of any of embodiments 1-81, wherein the modified oligonucleotide comprises at least one modified internucleoside linkage.

Embodiment 83. The compound of embodiment 82, wherein each internucleoside linkage is a modified internucleoside linkage.

Embodiment 84. The compound of embodiment 82 or 83, comprising at least one phosphorothioate internucleoside linkage.

Embodiment 85. The compound of embodiment 83, wherein each internucleoside linkage is a modified internucleoside linkage and wherein each internucleoside linkage comprises the same modification.

Embodiment 86. The compound of embodiment 85, wherein each internucleoside linkage is a phosphorothioate internucleoside linkage.

Embodiment 87. The compound of any of embodiments 1-86 comprising at least one conjugate.

Embodiment 88. The compound of any of embodiments 1-87 consisting of the modified oligonucleotide.

Embodiment 89. The compound of any of embodiments 1-88, wherein the compound modulates splicing of the LRP8 transcript.

Embodiment 90. A pharmaceutical composition comprising a compound according to any of embodiments 1-89 and a pharmaceutically acceptable carrier or diluent.

Embodiment 91. A method of modulating splicing an LRP8 transcript in a cell comprising contacting the cell with a compound according to any of embodiments 1-90.

Embodiment 92. The method of embodiment 91, wherein the cell is in vitro.

Embodiment 93. The method of embodiment 91, wherein the cell is in an animal.

Embodiment 94. A method of increasing the inclusion of exon 19 in LRP8 mRNA, comprising contacting the cell with a compound according to any of embodiments 1-90.

Embodiment 95. The method of embodiment 94, wherein the cell is in vitro.

Embodiment 96. The method of embodiment 94, wherein the cell is in an animal.

Embodiment 97. A method of preventing, treating, ameliorating, or slowing the progression of a disease, disorder, or condition associated with neurodegeneration, comprising administering the compound of any of embodiments 1 to 89 or the composition of embodiment 90 to an subject in need thereof.

Embodiment 98. The method of embodiment 97, wherein the condition associated with neurodegeneration is Alzheimer's Disease.

Embodiment 99. The method of embodiment 97, wherein the condition associated with neurodegeneration is Down Syndrome.

Embodiment 100. A method of increasing the ratio of LRP8 mRNA having exon 19 relative to LRP8 mRNA without exon 19, comprising contacting a cell with the compound of any of embodiments 1 to 88 or the composition of embodiment 90.

Embodiment 101. The method of embodiment 100, wherein the cell is in vitro.

Embodiment 102. The method of embodiment 100, wherein the cell is in an animal.

Embodiment 103. Use of the compound of any of embodiments 1 to 89 or the composition of embodiment 90 for the preparation of a medicament for use in the treatment of Alzheimer's Disease.

Embodiment 104. Use of the compound of any of embodiments 1 to 89 or the composition of embodiment 90 for the preparation of a medicament for use in the amelioration of one or more symptoms of Alzheimer's Disease.

Embodiment 105. The compound of any of embodiments 1 to 89 or the composition of embodiment 90 for use in treating Alzheimer's Disease.

Embodiment 106. The compound of any of embodiments 1 to 89 or the composition of embodiment 90 for use in the amelioration of one or more symptoms of Alzheimer's Disease.

Embodiment 107. The method of any of embodiments 97-99, wherein the subject is a male subject.

Embodiment 108. The method of any of embodiments 97-99, wherein the subject is a female subject.

Embodiment 109. A method of increasing the inclusion of exon 19 in LRP8 protein, comprising contacting the cell with a compound according to any of embodiments 1-90.

Embodiment 110. The method of embodiment 109, wherein the cell is in vitro.

Embodiment 111. The method of embodiment 109, wherein the cell is in an animal.

Embodiment 112. The compound of any of embodiments 1-12, wherein the target region is within nucleobase 78901 and nucleobase 78993 of SEQ ID NO.: 1.

Embodiment 113. The compound of any of embodiments 1-12, wherein the target region is within nucleobase 78901 and nucleobase 79003 of SEQ ID NO.: 1.

Embodiment 114. The compound of any of embodiments 1-12, wherein the target region is within nucleobase 78901 and nucleobase 79014 of SEQ ID NO.: 1.

Embodiment 115. The compound of any of embodiments 1-12, wherein the target region is within nucleobase 79170 and nucleobase 79258 of SEQ ID NO.: 1.

Embodiment 116. The compound of any of embodiments 1-12, wherein the target region is within nucleobase 79160 and nucleobase 79258 of SEQ ID NO.: 1.

Embodiment 117. The compound of any of embodiments 1-12, wherein the target region is within nucleobase 79150 and nucleobase 79258 of SEQ ID NO.: 1.

Embodiment 118. The compound of any of embodiments 112-117 wherein the modified oligonucleotide comprises at least one modified nucleoside.

Embodiment 119. The compound of embodiment 118, wherein at least one modified nucleoside comprises a modified sugar moiety.

Embodiment 120. The compound of embodiment 119, wherein at least one modified sugar moiety is a 2'-substituted sugar moiety.

Embodiment 121. The compound of embodiment 120, wherein the 2'-substitutent of at least one 2'-substituted sugar moiety is selected from among: 2'-OMe, 2'-F, and 2'-MOE.

Embodiment 122. The compound of embodiment 121, wherein the 2'-substituent of at least one 2'-substituted sugar moiety is a 2'-MOE.

Embodiment 123. The compound of any of embodiments 119-122, wherein at least one modified sugar moiety is a bicyclic sugar moiety.

Embodiment 124. The compound of embodiment 123, wherein at least one bicyclic sugar moiety is LNA or cEt.

Embodiment 125. The compound of any of embodiments 119-124, wherein at least one sugar moiety is a sugar surrogate.

Embodiment 126. The compound of embodiment 125, wherein at least one sugar surrogate is a morpholino.

Embodiment 127. The compound of embodiment 125, wherein at least one sugar surrogate is a modified morpholino.

Embodiment 128. The compound of any of embodiment 112-127, wherein the modified oligonucleotide comprises at least 5 modified nucleosides, each independently comprising a modified sugar moiety.

Embodiment 129. The compound of embodiment 128, wherein the modified oligonucleotide comprises at least 10 modified nucleosides, each independently comprising a modified sugar moiety.

Embodiment 130. The compound of embodiment 128, wherein the modified oligonucleotide comprises at least 15 modified nucleosides, each independently comprising a modified sugar moiety.

Embodiment 131. The compound of any of embodiments 128-130, wherein the modified oligonucleotide comprises one or more 2'-deoxynucleoside.

Embodiment 132. The compound of embodiment 128, wherein each nucleoside of the modified oligonucleotide is a modified nucleoside, each independently comprising a modified sugar moiety Embodiment 133. The compound of any of embodiments 112-132, wherein the modified oligonucleotide comprises at least two modified nucleosides comprising modified sugar moieties that are the same as one another.

Embodiment 134. The compound of any of embodiments 112-133, wherein the modified oligonucleotide comprises at least two modified nucleosides comprising modified sugar moieties that are different from one another.

Embodiment 135. The compound of any of embodiments 112-134, wherein the modified oligonucleotide comprises a modified region of at least 5 contiguous modified nucleosides.

Embodiment 136. The compound of embodiment 135, wherein the modified oligonucleotide comprises a modified region of at least 10 contiguous modified nucleosides.

Embodiment 137. The compound of embodiment 135, wherein the modified oligonucleotide comprises a modified region of at least 15 contiguous modified nucleosides.

Embodiment 138. The compound of embodiment 135, wherein the modified oligonucleotide comprises a modified region of at least 20 contiguous modified nucleosides.

Embodiment 139. The compound of any of embodiments 134-138, wherein each modified nucleoside of the modified region has a modified sugar moiety independently selected from among: 2'-F, 2'-OMe, 2'-MOE, cEt, LNA, morpholino, and modified morpholino.

Embodiment 140. The compound of any of embodiments 135-139, wherein the modified nucleosides of the modified region each comprise the same modification as one another.

Embodiment 141. The compound of embodiment 140, wherein the modified nucleosides of the modified region each comprise the same 2'-substituted sugar moiety.

Embodiment 142. The compound of embodiment 140, wherein the 2'-substituted sugar moiety of the modified nucleosides of the region of modified nucleosides is selected from 2'-F, 2'-OMe, and 2'-MOE.

Embodiment 143. The compound of embodiment 141, wherein the 2'-substituted sugar moiety of the modified nucleosides of the region of modified nucleosides is 2'-MOE.

Embodiment 144. The compound of embodiment 140, wherein the modified nucleosides of the region of modified nucleosides each comprise the same bicyclic sugar moiety.

Embodiment 145. The compound of embodiment 144, wherein the bicyclic sugar moiety of the modified nucleosides of the region of modified nucleosides is selected from LNA and cEt.

Embodiment 146. The compound of embodiment 140, wherein the modified nucleosides of the region of modified nucleosides each comprises a sugar surrogate.

Embodiment 147. The compound of embodiment 146, wherein the sugar surrogate of the modified nucleosides of the region of modified nucleosides is a morpholino.

Embodiment 148. The compound of embodiment 146, wherein the sugar surrogate of the modified nucleosides of the region of modified nucleosides is a modified morpholino.

Embodiment 149. The compound of any of embodiments 112-148, wherein the modified nucleotide comprises no more than 4 contiguous naturally occurring nucleosides.

Embodiment 150. The compound of any of embodiments 112-148, wherein each nucleoside of the modified oligonucleotide is a modified nucleoside.

Embodiment 151. The compound of embodiment 150 wherein each modified nucleoside comprises a modified sugar moiety.

Embodiment 152. The compound of embodiment 151, wherein the modified nucleosides of the modified oligonucleotide comprise the same modification as one another.

Embodiment 153. The compound of embodiment 152, wherein the modified nucleosides of the modified oligonucleotide each comprise the same 2'-substituted sugar moiety.

Embodiment 154. The compound of embodiment 153, wherein the 2'-substituted sugar moiety of the modified oligonucleotide is selected from 2'-F, 2'-OMe, and 2'-MOE.

Embodiment 155. The compound of embodiment 154, wherein the 2'-substituted sugar moiety of the modified oligonucleotide is 2'-MOE.

Embodiment 156. The compound of embodiment 152, wherein the modified nucleosides of the modified oligonucleotide each comprise the same bicyclic sugar moiety.

Embodiment 157. The compound of embodiment 156, wherein the bicyclic sugar moiety of the modified oligonucleotide is selected from LNA and cEt.

Embodiment 158. The compound of embodiment 152, wherein the modified nucleosides of the modified oligonucleotide each comprises a sugar surrogate.

Embodiment 159. The compound of embodiment 158, wherein the sugar surrogate of the modified oligonucleotide is a morpholino.

Embodiment 160. The compound of embodiment 158, wherein the sugar surrogate of the modified oligonucleotide is a modified morpholino.

Embodiment 161. The compound of any of embodiments 112-160, wherein the modified oligonucleotide comprises at least one modified internucleoside linkage.

Embodiment 162. The compound of embodiment 161, wherein each internucleoside linkage is a modified internucleoside linkage.

Embodiment 163. The compound of embodiment 161 or 162, comprising at least one phosphorothioate internucleoside linkage.

Embodiment 164. The compound of embodiment 162, wherein each internucleoside linkage is a modified internucleoside linkage and wherein each internucleoside linkage comprises the same modification.

Embodiment 165. The compound of embodiment 164, wherein each internucleoside linkage is a phosphorothioate internucleoside linkage.

Embodiment 166. The compound of any of embodiments 112-165 comprising at least one conjugate.

Embodiment 167. The compound of any of embodiments 112-166 consisting of the modified oligonucleotide.

Embodiment 168. The compound of any of embodiments 112-167, wherein the compound modulates splicing of the LRP8 transcript.

Embodiment 169. A pharmaceutical composition comprising a compound according to any of embodiments 112-168 and a pharmaceutically acceptable carrier or diluent.

Embodiment 170. A method of modulating splicing an LRP8 transcript in a cell comprising contacting the cell with a compound according to any of embodiments 112-169.

Embodiment 171. The method of embodiment 170, wherein the cell is in vitro.

Embodiment 172. The method of embodiment 170, wherein the cell is in an animal.

Embodiment 173. A method of increasing the inclusion of exon 19 in LRP8 mRNA, comprising contacting the cell with a compound according to any of embodiments 112-169.

Embodiment 174. The method of embodiment 173, wherein the cell is in vitro.

Embodiment 175. The method of embodiment 173, wherein the cell is in an animal.

Embodiment 176. A method of preventing, treating, ameliorating, or slowing the progression of a disease, disorder, or condition associated with neurodegeneration, comprising administering the compound of any of embodiments 1 to 89 or the composition of embodiment 90 to an subject in need thereof.

Embodiment 177. The method of embodiment 176, wherein the condition associated with neurodegeneration is Alzheimer's Disease.

Embodiment 178. The method of embodiment 176, wherein the condition associated with neurodegeneration is Down Syndrome.

Embodiment 179. A method of increasing the ratio of LRP8 mRNA having exon 19 relative to LRP8 mRNA without exon 19, comprising contacting a cell with the compound of any of embodiments 112 to 167 or the composition of embodiment 169.

Embodiment 180. The method of embodiment 179, wherein the cell is in vitro.

Embodiment 181. The method of embodiment 179, wherein the cell is in an animal.

Embodiment 182. Use of the compound of any of embodiments 112 to 168 or the composition of embodiment 169 for the preparation of a medicament for use in the treatment of Alzheimer's Disease.

Embodiment 183. Use of the compound of any of embodiments 112 to 168 or the composition of embodiment 169 for the preparation of a medicament for use in the amelioration of one or more symptoms of Alzheimer's Disease.

Embodiment 184. The compound of any of embodiments 112 to 168 or the composition of embodiment 169 for use in treating Alzheimer's Disease.

Embodiment 185. The compound of any of embodiments 112 to 168 or the composition of embodiment 169 for use in the amelioration of one or more symptoms of Alzheimer's Disease.

Embodiment 186. The method of any of embodiments 176-178, wherein the subject is a male subject.

Embodiment 187. The method of any of embodiments 176-178, wherein the subject is a female subject.

Embodiment 188. A method of increasing the inclusion of exon 19 in LRP8 protein, comprising contacting the cell with a compound according to any of embodiments 112-169.

Embodiment 189. The method of embodiment 188, wherein the cell is in vitro.

Embodiment 190. The method of embodiment 188, wherein the cell is in an animal.

In certain embodiments, including, but not limited to any of the above numbered embodiments, the LRP8 transcript is in a human having Alzheimer's Disease. In certain such embodiments, the LRP8 gene of the human comprises a mutation that decreases the amount of exon 19 included in LRP8 mRNA.

DETAILED DESCRIPTION OF THE INVENTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $^{2nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means $—OCH_2CH_2OCH_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid.

Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH($CH_3$)—O-2'bridge.

As used herein, "locked nucleic acid nucleoside" or "LNA" means a nucleoside comprising a bicyclic sugar moiety comprising a 4'-$CH_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-mRNA includes one or more intron.

As used herein, "transcript" means an RNA molecule transcribed from DNA. Transcripts include, but are not limited to mRNA, pre-mRNA, and partially processed RNA.

As used herein, "APOER2" or "LRP8" means Apolipoprotein E receptor 2.

As used herein, "APOER2 transcript", "LRP8 transcript", or "Apolipoprotein E receptor 2 transcript" means a transcript transcribed from an Apolipoprotein E receptor 2 Gene. In certain embodiments, "APOER2 transcript", "LRP8 transcript", or "Apolipoprotein E receptor 2 transcript" means the complement of GENBANK accession number NT_032977.7 truncated from nucleotides 7530205 to 7613614 (SEQ ID NO: 1). In certain embodiments, an ApoER2 transcript is at least 90% identical to the complement of GENBANK accession number NT_032977.7 truncated from nucleotides 7530205 to 7613614, set forth as SEQ ID NO 1. In certain embodiments, an ApoER2 transcript is 100% identical to the complement of GENBANK accession number NT_032977.7 truncated from nucleotides 7530205 to 7613614, set forth as SEQ ID NO: 1.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, “nucleobase modification motif” means a pattern of modifications to nucleobases along an oligonucleotide. Unless otherwise indicated, a nucleobase modification motif is independent of the nucleobase sequence.

As used herein, “sequence motif” means a pattern of nucleobases arranged along an oligonucleotide or portion thereof. Unless otherwise indicated, a sequence motif is independent of chemical modifications and thus may have any combination of chemical modifications, including no chemical modifications.

As used herein, “type of modification” in reference to a nucleoside or a nucleoside of a “type” means the chemical modification of a nucleoside and includes modified and unmodified nucleosides. Accordingly, unless otherwise indicated, a “nucleoside having a modification of a first type” may be an unmodified nucleoside.

As used herein, “differently modified” mean chemical modifications or chemical substituents that are different from one another, including absence of modifications. Thus, for example, a MOE nucleoside and an unmodified DNA nucleoside are “differently modified,” even though the DNA nucleoside is unmodified. Likewise, DNA and RNA are “differently modified,” even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, “the same type of modifications” refers to modifications that are the same as one another, including absence of modifications. Thus, for example, two unmodified DNA nucleoside have “the same type of modification,” even though the DNA nucleoside is unmodified. Such nucleosides having the same type modification may comprise different nucleobases.

As used herein, “pharmaceutically acceptable carrier or diluent” means any substance suitable for use in administering to an animal. In certain embodiments, a pharmaceutically acceptable carrier or diluent is sterile saline. In certain embodiments, such sterile saline is pharmaceutical grade saline.

As used herein, “substituent” and “substituent group,” means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, “substituent” in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($—C(O)R_{aa}$), carboxyl ($—C(O)O—R_{aa}$), aliphatic groups, alicyclic groups, alkoxy, substituted oxy ($—O—R_{aa}$), aryl, aralkyl, heterocyclic radical, heteroaryl, heteroarylalkyl, amino ($—N(R_{bb})(R_{cc})$), imino($=NR_{bb}$), amido ($—C(O)N(R_{bb})(R_{cc})$ or $—N(R_{bb})C(O)R_{aa}$), azido ($—N_3$), nitro ($—NO_2$), cyano ($—CN$), carbamido ($—OC(O)N(R_{bb})(R_{cc})$ or $—N(R_{bb})C(O)OR_{aa}$), ureido ($—N(R_{bb})C(O)N(R_{bb})(R_{cc})$), thioureido ($—N(R_{bb})C(S)N(R_{bb})—(R_{cc})$), guanidinyl ($—N(R_{bb})C(=NR_{bb})N(R_{bb})(R_{cc})$), amidinyl ($—C(=NR_{bb})N(R_{bb})(R_{cc})$ or $—N(R_{bb})C(=NR_{bb})(R_{aa})$), thiol ($—SR_{bb}$), sulfinyl ($—S(O)R_{bb}$), sulfonyl ($—S(O)_2R_{bb}$) and sulfonamidyl ($—S(O)_2N(R_{bb})(R_{cc})$ or $—N(R_{bb})S—(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, “alkyl,” as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, “alkenyl,” means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, “alkynyl,” means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, “acyl,” means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, “alicyclic” means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modifed nucleosides comprising a modifed sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, $O(CH_2)_2SCH_3$, $O(CH_2)_2$—O—N(Rm)(Rn), and O—$CH_2$—C(═O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)_2SCH_3$, O—$(CH_2)_2$—O—N($R_m$)($R_n$), $O(CH_2)_2O(CH_2)_2N(CH_3)_2$, and N-substituted acetamide (O—$CH_2$—C(═O)—N($R_m$)

($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, O—$(CH_2)_2$—O—$N(CH_3)_2$, —$O(CH_2)_2O(CH_2)_2N(CH_3)_2$, and O—$CH_2$—C(═O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —$[C(R_a)(R_b)]_n$—, —$[C(R_a)(R_b)]_n$—O—, —$C(R_aR_b)$—N(R)—O— or, —$C(R_aR_b)$—O—N(R)—; 4'-$CH_2$-2', 4'-$(CH_2)_2$-2',4'-$(CH_2)_3$-2',4'-$(CH_2)$—O-2' (LNA); 4'-$(CH_2)$—S-2; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*, 2009, 74, 118-134); and 4'-$CH_2$—C(═$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —$[C(R_a)(R_b)]_n$—, —$C(R_a)$═$C(R_b)$—, —$C(R_a)$═N—, —C(═$NR_a$)—, —C(═O)—, —C(═S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl ($S(=O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

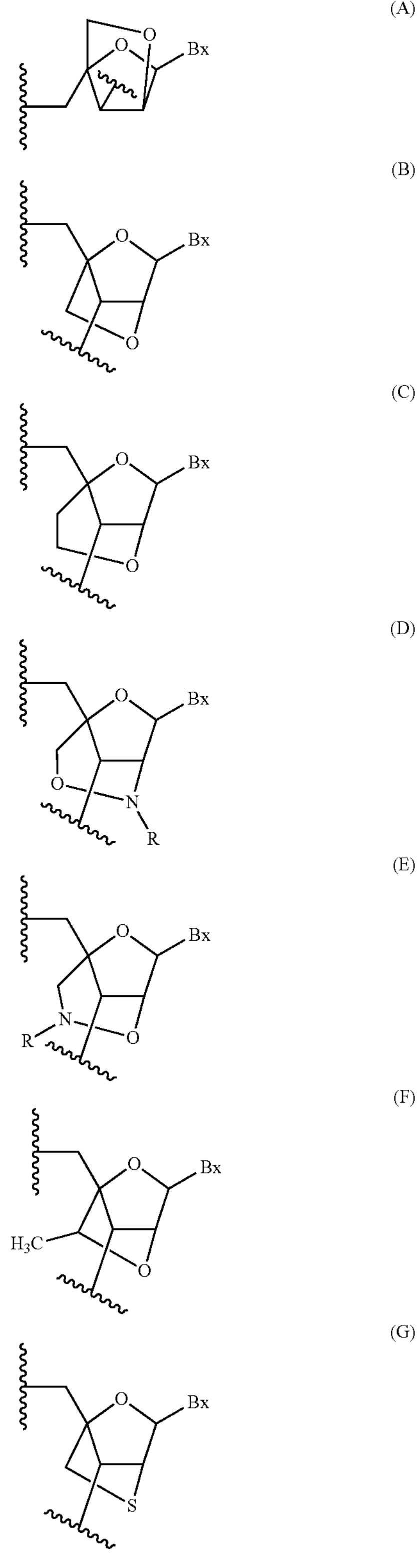

-continued (H)

(I)

(J)

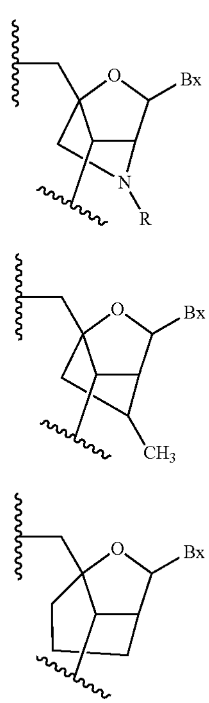

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. No. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), mannitol nucleic acid (MNA) (see Leumann, C J. *Bioorg. & Med. Chem.* (2002) 10:841-854), fluoro HNA (F-HNA), and those compounds having Formula VII:

VII

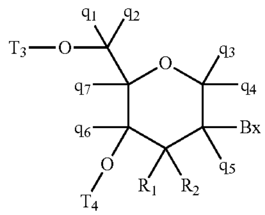

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

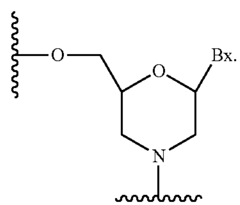

In certain embodiments, morpholinos may be modified, for example by adding or altering various substituent groups from the above morpholino structure. Such sugar surrogates are referred to herein as "modifed morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modifed nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15*, Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

Certain Target Nucleic Acids and Mechanisms

Apolipoprotein E receptor 2 (APOER2 or LRP8) is a post-synaptic transmembrane protein that mediates a signaling cascade initiated by the binding of ligands including ApoE and Reelin. LRP8 has been found to protect against loss of coricospinoneurons during normal aging. In certain embodiments, LRP8 protein isoforms that lack exon 19 act as dominant negative inhibitors and cause defects in long-term memory storage and spatial learning. In certain embodiments, a disruption in the alternative splicing of the LRP8 transcript disrupts signaling and leads to learning and memory defects similar to those seen in Alzheimer's Disease.

In certain embodiments, splicing of LRP8 exon 19 decreases and the decrease in exon 19 splicing causes LRP8 mRNA without exon 19, which in turn contributes to Alzheimer's Disease. In certain embodiments, improving the splicing of LRP8 to include exon 19 or to increase the ratio of mRNA containing exon 19 compared to mRNA without exon 19 ameliorates one or more symptoms of Alzheimer's Disease. In certain embodiments, improving the splicing of LRP8 to include exon 19 or to increase the ratio of mRNA containing exon 19 compared to mRNA without exon 19 delays the onset of one or more symptoms of Alzheimer's Disease. In certain embodiments, improving the splicing of LRP8 to include exon 19 or to increase the ratio of mRNA containing exon 19 compared to mRNA without exon 19 improves memory and/or learning. In certain embodiments, antisense oligonucleotides described herein improve exon 19 splicing and increase inclusion of exon 19 in LRP8 mRNA.

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is an LRP8 transcript. In certain embodiments, the target RNA is an LRP8 pre-mRNA.

In certain embodiments, an antisense compound is complementary to a region of an LRP8 pre-mRNA. In certain embodiments, an antisense compound is complementary within a region of an LRP8 pre-mRNA comprising exon 19 or the intronic region upstream or downstream of exon 19. In certain embodiments, an antisense compound is complementary to a region of an LRP8 pre-mRNA containing an intronic splice silencer for exon 19. In certain embodiments, the intronic splice silencer for exon 19 is located in a region of an LRP8 pre-mRNA upstream of the 5'-splice site for exon 19. In certain embodiments, the intronic splice silencer for exon 19 is located in a region of an LRP8 pre-mRNA downstream of the 3'-splice site for exon 19. In certain embodiments, an antisense compound is complementary to a region of an LRP8 pre-mRNA 6 to 59 nucleotides downstream of the 5'splice site of exon 19.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equal length of an LRP8 transcript.

In certain embodiments, an antisense oligonucleotide modulates splicing of a pre-mRNA. In certain embodiments, an antisense oligonucleotide modulates splicing of an LRP8 pre-mRNA. In certain embodiments, an antisense oligonucleotide increases the amount of spliced LRP8 mRNA that contains exon 19. In certain embodiments, an antisense oligonucleotide increases the inclusion of exon 19 LRP8 mRNA. In certain embodiments, an antisense oligonucleotide increases that amount of spliced LRP8 mRNA that contains exon 19.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one symptom associated with Alzheimer's Disease. In certain embodiments, such administration results in amelioration of at least one symptom of Alzheimer's Disease. In certain embodiments, administration of a pharmaceutical composition to an animal results in an increase LRP8 mRNA having exon 19 in a cell of the animal. In certain embodiments, an LRP8 protein having exon 19 amino acids is preferred over an LRP8 protein without exon 19 amino acids. In certain embodiments, administration of a pharmaceutical composition results in amelioration of one or more symptoms associated with Alzheimer's Disease. In certain embodiments, such amelioration is the reduction in severity of such symptoms. In certain embodiments, amelioration is the delayed onset of such symptoms. In certain embodiments, amelioration is the slowed progression of such symptoms. In certain embodiments, amelioration is the prevention of such symptoms. In certain embodiments, amelioration is the slowed progression of such symptoms. In certain embodiments, amelioration is the reversal of such symptoms.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Antisense Modulation of Human LRP8 Transcript Splicing In Vitro

Antisense oligonucleotides (ASO's) complementary to one of the introns flanking exon 19 of the human LRP8 pre-mRNA were synthesized and tested for their ability to modulate splicing of exon 19. The ASO's target the complement of GENBANK accession number NT_032977.7 truncated from nucleotides 7530205 to 7613614 (SEQ ID NO: 1). The sugar moieties of the nucleotides are uniformly 2'-MOE modified, and all internucleoside linkages are phosphorothioate linkages. The cytosine bases are 5-methylcytosine, and the ASO sequences are listed in Table 1 below. The start and stop sites associated with each oligonucleotide are the 5'- and 3'-positions, respectively, of the portion of SEQ ID NO: 1 that is complementary to the ASO.

To test the ability of the antisense oligonucleotides to increase exon 19 inclusion in LRP8 mRNA, HeLa cells were transfected with 50 nM of the ASOs listed in Table 1 using Lipofectamine 2000. Untransfected control cells (UTC) did not receive ASO treatment, and ISIS 439272 that does not target LRP8 was used as a negative control. After 48 hours, total RNA was collected from the cells and radioactive semi-quantitative RT-PCR was used to identify LRP8 transcripts with and without exon 19. The PCR products were analyzed by PAGE and quantitated by phosphorimager analysis (Typhoon 9400, GE Healthcare). The results are shown in Table 1 below as percentage of exon 19 inclusion, which was defined as 100×[(amount of transcript with exon 19 included)/(total transcript with exon 19 included and exon 19 excluded)]. As illustrated in Table 1, in certain embodiments, antisense oligonucleotides complementary to an intron flanking exon 19 of human LRP8 pre-mRNA increased the percentage of exon 19 inclusion in the mRNA transcript.

TABLE 1

Antisense modulation of human exon 19 inclusion in vitro

| ISIS No. | Start site | Stop site | Sequence | Exon 19 inclusion (%) | SEQ ID No. |
|---|---|---|---|---|---|
| UTC | n/a | n/a | n/a | 16 | n/a |
| 439272 | n/a | n/a | TTAGTTTAATCACGCTCG | 12 | 2 |
| 594167 | 78901 | 78918 | CCTGCTGTGCCACTTTGT | 15 | 3 |
| 594168 | 78906 | 78923 | TGACACCTGCTGTGCCAC | 20 | 4 |
| 594169 | 78911 | 78928 | AACAGTGACACCTGCTGT | 29 | 5 |
| 594170 | 78916 | 78933 | TGTATAACAGTGACACCT | 27 | 6 |
| 594171 | 78921 | 78938 | TGTGCTGTATAACAGTGA | 27 | 7 |
| 594172 | 78926 | 78943 | CTGACTGTGCTGTATAAC | 28 | 8 |
| 594173 | 78931 | 78948 | GCCCCCTGACTGTGCTGT | 25 | 9 |
| 594174 | 78936 | 78953 | ACTCAGCCCCCTGACTGT | 22 | 10 |
| 594175 | 78941 | 78958 | GTCACACTCAGCCCCCTG | 28 | 11 |
| 594176 | 78946 | 78963 | CTGAGGTCACACTCAGCC | 31 | 12 |
| 594177 | 78951 | 78968 | GACCTCTGAGGTCACACT | 21 | 13 |
| 586106 | 78956 | 78973 | TGGATGACCTCTGAGGTC | 16 | 14 |
| 594178 | 78961 | 78978 | CACTGTGGATGACCTCTG | 27 | 15 |
| 586108 | 79171 | 79188 | AGAGTGGCACTGCCCTAC | 5 | 16 |
| 594179 | 79176 | 79193 | GACTTAGAGTGGCACTGC | 64 | 17 |
| 594180 | 79181 | 79198 | CCTCAGACTTAGAGTGGC | 72 | 18 |
| 594181 | 79186 | 79203 | CAGCCCCTCAGACTTAGA | 58 | 19 |
| 594182 | 79191 | 79208 | CTCACCAGCCCCTCAGAC | 47 | 20 |
| 594183 | 79196 | 79213 | CCTCACTCACCAGCCCCT | 22 | 21 |
| 594184 | 79201 | 79218 | CATGCCCTCACTCACCAG | 39 | 22 |
| 594185 | 79206 | 79223 | TGGTTCATGCCCTCACTC | 47 | 23 |
| 594186 | 79211 | 79228 | TGCCTTGGTTCATGCCCT | 36 | 24 |
| 594187 | 79216 | 79233 | GCGCCTGCCTTGGTTCAT | 12 | 25 |
| 594188 | 79221 | 79238 | TGGCTGCGCCTGCCTTGG | 32 | 26 |
| 594189 | 79226 | 79243 | AGGATTGGCTGCGCCTGC | 29 | 27 |
| 594190 | 79231 | 79248 | CTTCTAGGATTGGCTGCG | 17 | 28 |
| 594191 | 79236 | 79253 | AAAGCCTTCTAGGATTGG | 29 | 29 |
| 594192 | 79241 | 79258 | ACCAGAAAGCCTTCTAGG | 17 | 30 |

Example 2

Antisense Modulation of Mouse LRP8 Transcript Splicing In Vitro

Antisense oligonucleotides (ASO's) complementary to one of the introns flanking exon 19 of the mouse LRP8 pre-mRNA were synthesized and tested for their ability to modulate splicing of exon 19. The ASO's target GENBANK accession number NT_039264.6 truncated from nucleotides 7925000 to 8001600 (SEQ ID NO: 31). The sugar moieties of the nucleotides are uniformly 2'-MOE modified, and all internucleoside linkages are phosphorothioate linkages. The cytosine bases are 5-methylcytosine, and the ASO sequences are listed in Table 2 below. The start and stop sites associated with each oligonucleotide are the 5'- and 3'-positions, respectively, of the portion of SEQ ID NO: 31 that is complementary to the ASO.

To test the ability of the antisense oligonucleotides to increase exon 19 inclusion in LRP8 mRNA, 208ee mouse cells derived from adult C57/BL6 mouse kidney were transfected with 50 nM of the ASOs listed in Table 2 using Lipofectamine 2000. Untransfected control cells (UTC) did not receive ASO treatment, and ISIS 439272 that does not target LRP8 was used as a negative control. After 48 hours, total RNA was collected and analyzed as described in Example 1. The results are shown in Table 2 below as the percentage of exon 19 inclusion, as defined in Example 1. As illustrated in Table 2, in certain embodiments, antisense oligonucleotides complementary to an intron flanking exon 19 of mouse LRP8 pre-mRNA increased the percentage of exon 19 inclusion in the mRNA transcript.

TABLE 2

Antisense modulation of mouse exon 19 inclusion in vitro

| ISIS No. | Start site | Stop site | Sequence | Exon 19 inclusion (%) | SEQ ID No. |
|---|---|---|---|---|---|
| UTC | n/a | n/a | n/a | 30 | n/a |
| 439272 | n/a | n/a | TTAGTTTAATCACGCTCG | 23 | 2 |
| 586095 | 68727 | 68744 | CCTGTTCTAACCGCTTCA | No data | 32 |
| 586096 | 68732 | 68749 | CGACACCTGTTCTAACCG | 56 | 33 |
| 586097 | 68737 | 68754 | AACAACGACACCTGTTCT | 53 | 34 |
| 586098 | 68742 | 68759 | TGTGCAACAACGACACCT | 58 | 35 |
| 586099 | 68747 | 68764 | TCTGCTGTGCAACAACGA | 75 | 36 |
| 586100 | 68752 | 68769 | CTGACTCTGCTGTGCAAC | 77 | 37 |
| 586101 | 68757 | 68774 | GCCCCCTGACTCTGCTGT | 63 | 38 |
| 586102 | 68762 | 68779 | ACTCAGCCCCCTGACTCT | 45 | 39 |
| 586103 | 68767 | 68784 | GTCATACTCAGCCCCCTG | 55 | 40 |
| 586104 | 68772 | 68789 | CTGAGGTCATACTCAGCC | 42 | 41 |
| 586105 | 68777 | 68794 | GACCTCTGAGGTCATACT | 26 | 42 |
| 586106 | 68782 | 68799 | TGGATGACCTCTGAGGTC | 37 | 14 |
| 586107 | 68787 | 68804 | TGGACTGGATGACCTCTG | 65 | 43 |
| 586108 | 68994 | 69011 | AGAGTGGCACTGCCCTAC | 8 | 16 |
| 586109 | 68999 | 69016 | GGCTCAGAGTGGCACTGC | 97 | 44 |
| 586110 | 69004 | 69021 | CCTCAGGCTCAGAGTGGC | 91 | 45 |
| 586111 | 69009 | 69026 | CAGCCCCTCAGGCTCAGA | 90 | 46 |
| 586112 | 69014 | 69031 | CTCGCCAGCCCCTCAGGC | 84 | 47 |
| 586113 | 69019 | 69036 | CCTCACTCGCCAGCCCCT | 52 | 48 |
| 586114 | 69024 | 69041 | AAGGCCCTCACTCGCCAG | 72 | 49 |
| 586115 | 69029 | 69046 | GGTTTAAGGCCCTCACTC | 89 | 50 |
| 586116 | 69034 | 69051 | GCCTAGGTTTAAGGCCCT | 65 | 51 |
| 586117 | 69039 | 69056 | TAGCTGCCTAGGTTTAAG | 41 | 52 |
| 586118 | 69044 | 69061 | TTCTATAGCTGCCTAGGT | 78 | 53 |
| 586119 | 69049 | 69066 | GGATTTTCTATAGCTGCC | 92 | 54 |

TABLE 2-continued

Antisense modulation of mouse exon 19 inclusion in vitro

| ISIS No. | Start site | Stop site | Sequence | Exon 19 inclusion (%) | SEQ ID No. |
|---|---|---|---|---|---|
| 586120 | 69054 | 69071 | TGCTAGGATTTTCTATAG | 67 | 55 |
| 586121 | 69059 | 69076 | AAGCCTGCTAGGATTTTC | 64 | 56 |
| 586122 | 69064 | 69081 | TCAGAAAGCCTGCTAGGA | 80 | 57 |

Example 3

Dose Dependent Antisense Modulation of Mouse LRP8 Transcript Splicing In Vitro ISIS 586109 (see Table 2) was selected for use in a dose response experiment. Following the procedures described in Example 2, ISIS 586109 or the control oligonucleotide ISIS 439272 was added to 208ee cells at the concentrations listed in Table 3 below. The results are shown in Table 3 as the percentage of exon 19 inclusion, as defined in Example 1. As illustrated in Table 3, ISIS 586109 increased exon 19 inclusion in mouse LRP8 mRNA in a dose dependent manner.

TABLE 3

Dose dependent antisense modulation of mouse exon 19 inclusion in vitro

| ISIS No. | Dose (nM) | Exon 19 inclusion (%) | SEQ ID No. |
|---|---|---|---|
| UTC | n/a | 34 | n/a |
| 439272 | 100.0 | 34 | 2 |
| 586109 | 0.024 | 34 | 46 |
| | 0.049 | 34 | |
| | 0.098 | 34 | |
| | 0.195 | 33 | |
| | 0.391 | 36 | |
| | 0.781 | 56 | |
| | 1.56 | 50 | |
| | 3.13 | 58 | |
| | 6.25 | 59 | |
| | 12.5 | 67 | |
| | 25.0 | 76 | |
| | 50.0 | 87 | |
| | 100.0 | 87 | |

Example 4

Antisense Modulation of Mouse LRP8 Transcript Splicing In Vivo

Adult, wild type mice received a single 500 μg intracerebroventricular injection of ISIS No. 586108, 586109, 586110, 586115, 586119 (see Table 2) or control ASO ISIS No. 439272 under isoflurane anesthesia. Each treatment group consisted of three mice. Three weeks after the single ICV injection, the mice were euthanized and RNA was isolated from the hippocampus. Radioactive RT-PCR was performed and analyzed as described in Example 1. The average results for each treatment group are presented in Table 4 below as the ratio of the amount of exon 19 included mRNA to the amount of exon 19 excluded mRNA. As indicated by the results in Table 4 below, antisense oligonucleotides that induced LRP8 exon 19 inclusion in vitro also induced LRP8 exon 19 inclusion in mice in vivo.

TABLE 4

Antisense modulation of mouse exon 19 inclusion in vivo

| ISIS No. | Exon 19 included mRNA:Exon 19 excluded mRNA | Std. Error Meas. | SEQ ID No. |
|---|---|---|---|
| 439272 | 0.62 | 0.04 | 2 |
| 586108 | 0.56 | 0.01 | 16 |
| 586109 | 1.69 | 0.12 | 46 |
| 586110 | 1.42 | 0.09 | 45 |
| 586115 | 1.79 | 0.14 | 50 |
| 586119 | 1.70 | 0.11 | 54 |

Example 5

Antisense Modulation of Mouse LRP8 Transcript Splicing in a Mouse Model of Alzheimer's Disease The transgenic mouse line TgCRND8 (see Chishti et al., *J. Biol. Chem.,* 2001, 276, 21562-21570 and Janus et al., *Nature,* 2000, 408, 979-982) is a mouse model of Alzheimer's Disease that harbors the human APP695 cDNA transgene with the Swedish (K670M, N671L) and Indiana (V717F) mutations. The TgCRND8 mice exhibit amyloid plaques in the cortex and hippocampus by three months of age, along with impaired performance on learning and memory tasks and increased locomotor activity. Neonatal wild type and TgCRND8 mice were treated one or two days after birth with 15 μg of ISIS No. 586115 (see Table 2) or control ASO ISIS No. 439272. The ASOs were administered by intracerebroventricular injection. At post-natal day 8 (P8), four months, and six months of age, LRP8 exon 19 inclusion in the hippocampus was assessed by RT-PCR, as described in Example 4. At four months of age, exon 19 inclusion in LRP8 protein in the hippocampus was also measured by western blot using an antibody specific to exon 19, and LRP8 protein levels were normalized to β-actin. Exon 19 inclusion in LRP8 mRNA in the cortex was also assessed at four months of age, by RT-PCR. To assess tolerability of the antisense oligonucleotides, the weights of the mice were measured. Two markers of inflammation, Aif1 and GFAP, were measured by RT-PCR and/or immunoblot normalized to β-actin levels. The average results for each treatment group are presented in Tables 5.1-5.7 below. As illustrated in the tables below, treatment with ISIS 586115 was well tolerated and increased exon 19 inclusion in mouse LRP8 mRNA and protein in vivo in both wild type and a mouse model of Alzheimer's Disease.

TABLE 5.1

Antisense modulation of mouse exon 19 inclusion in vivo at P8

| Isis No. | Genotype | Number of mice in group | Exon 19 included mRNA:Exon 19 excluded mRNA | Std. Error Meas. | SEQ ID No. |
|---|---|---|---|---|---|
| 439272 | TgCRND8 | 5 | 0.48 | 0.02 | 2 |
| 586115 | TgCRND8 | 4 | 1.46 | 0.24 | 50 |

TABLE 5.2

Antisense modulation of mouse exon 19 inclusion in vivo four months following a single ICV dose

| Isis No. | Genotype | Number of mice in group | Exon 19 included mRNA:Exon 19 excluded mRNA | Std. Error Meas. | SEQ ID No. |
|---|---|---|---|---|---|
| 439272 | WT | 8 | 0.86 | 0.12 | 2 |
| 586115 | WT | 17 | 1.48 | 0.17 | 50 |
| 439272 | TgCRND8 | 13 | 0.71 | 0.05 | 2 |
| 586115 | TgCRND8 | 18 | 1.49 | 0.12 | 50 |

TABLE 5.3

Mouse exon 19 inclusion in LRP8 protein in hippocampus four months following a single ICV dose

| Isis No. | Genotype | Number of mice in group | Exon 19 included protein:Exon 19 excluded protein | Std. Error Meas. |
|---|---|---|---|---|
| 439272 | TgCRND8 | 5 | 0.67 | 0.11 |
| 586115 | TgCRND8 | 4 | 1.74 | 0.23 |

TABLE 5.4

Antisense modulation of mouse exon 19 inclusion in cortex four months following a single ICV dose

| Isis No. | Genotype | Number of mice in group | Exon 19 included mRNA:Exon 19 excluded mRNA | Std. Error Meas. |
|---|---|---|---|---|
| 439272 | TgCRND8 | 3 | 0.86 | 0.11 |
| 586115 | TgCRND8 | 5 | 5.55 | 1.43 |

TABLE 5.5

Mouse exon 19 inclusion in hippocampus six months following a single ICV dose

| Isis No. | Genotype | Number of mice in group | Exon 19 included mRNA:Exon 19 excluded mRNA | Std. Error Meas. |
|---|---|---|---|---|
| 439272 | TgCRND8 | 6 | 0.75 | 0.03 |
| 586115 | Mixed group of WT & TgCRND8 | 11 | 1.23 | 0.12 |

TABLE 5.6

Mouse body weights three months following a single ICV dose

| Genotype | Isis No. | Sex | Number of mice in group | Weight (g) | Std. Error Meas. |
|---|---|---|---|---|---|
| WT | None | Male | 12 | 32.23 | 1.31 |
| | | Female | 14 | 24.78 | 0.86 |
| WT | 439272 | Male | 11 | 29.43 | 0.58 |
| | | Female | 16 | 23.75 | 1.03 |
| WT | 586115 | Male | 10 | 30.04 | 0.92 |
| | | Female | 11 | 24.81 | 0.64 |
| TgCRND8 | None | Male | 10 | 23.44 | 0.83 |
| | | Female | 10 | 18.36 | 1.11 |
| TgCRND8 | 439272 | Male | 8 | 23.73 | 0.56 |
| | | Female | 16 | 18.61 | 0.41 |
| TgCRND8 | 586115 | Male | 10 | 23.55 | 0.83 |
| | | Female | 9 | 19.23 | 0.62 |

TABLE 5.7

Inflammation markers in hippocampus four months following a single ICV dose

| Isis No. | Genotype | Number of mice in group | GFAP | Std. Error Meas. | Aif1 | Std. Error Meas. |
|---|---|---|---|---|---|---|
| 439272 | TgCRND8 | 3 | 1.09 | 0.05 | 0.95 | 0.06 |
| 586115 | TgCRND8 | 3 | 1.02 | 0.06 | 0.92 | 0.08 |

Example 6

Phenotypic Effect of Antisense Oligonucleotides in a Mouse Model of Alzheimer's Disease In order to test whether ASOs that induce LRP8 exon 19 inclusion ameliorate the learning and memory deficits of TgCRND8 mice, the mice were assessed in the Morris water maze at 11 to 12 weeks of age. Wild type and TgCRND8 mice that had received ICV ASO injections as neonates (see Example 5) as well as untreated control mice were placed individually in a circular pool, 48 inches in diameter, filled to a depth of 26 inches with 23° C. water. The pool walls were made opaque with white paint and placed in a room with prominent extra-maze cues at least 16 inches from the pool edge. Four unique, proximal cues were affixed to the 8 cm high interior pool wall above water level at 0, 90, 180, and 270 degrees. Mice were placed in one of four starting quadrants facing the pool wall and allowed to swim until coming to rest atop a 4 inch square plexiglass platform submerged in 0.5 cm of water, or until a maximum of 60 seconds. Upon finding the platform, mice were left there for 20 seconds before reentry at the next start point or removal from the cage. Mice that did not find the platform within 60 seconds were guided to it by the experimenter. Trials were performed once at each starting quadrant point per session. Mice were tested for four consecutive days with two sessions of four trials each per day, and their movement was tracked using HSVimage automated video tracking software. The total distance each mouse traveled to reach the platform was measured. The average results for each treatment group for all eight daily trials are shown in Table 6 below, illustrating that treatment with an antisense oligonucleotide that induces an increase in LRP8 exon 19 inclusion improved the learning and memory of TgCRND8 mice.

TABLE 6

Effect of an antisense oligonucleotide that mediates exon 19 inclusion on learning and memory

| Isis No. | Genotype | Number of mice in group | Trial day | Distance traveled (cm) | Std. Error Meas. | SEQ ID No. |
|---|---|---|---|---|---|---|
| 439272 | WT | 24 | 1 | 684 | 29 | 2 |
| | | | 2 | 404 | 27 | |
| | | | 3 | 360 | 36 | |
| | | | 4 | 334 | 38 | |
| 586115 | WT | 20 | 1 | 694 | 47 | 50 |
| | | | 2 | 449 | 43 | |
| | | | 3 | 435 | 51 | |
| | | | 4 | 354 | 44 | |
| 439272 | TgCRND8 | 24 | 1 | 749 | 48 | 2 |
| | | | 2 | 730 | 49 | |
| | | | 3 | 690 | 58 | |
| | | | 4 | 594 | 39 | |
| 586115 | TgCRND8 | 16 | 1 | 809 | 48 | 50 |
| | | | 2 | 676 | 52 | |
| | | | 3 | 526 | 52 | |
| | | | 4 | 547 | 72 | |

Example 7

Phenotypic Effect of Antisense Oligonucleotides in a Mouse Model of Alzheimer's Disease Groups of male, 11 to 12 week old mice were tested in the Morris water maze, as described in Example 6. The experimenter was blind to the genotype of the mice. Latency to reach the platform, distance traveled to reach the platform, swim speed, time spent in each of 4 quadrants, and time spent along the walls, were obtained using automated video tracking software (HSVimage). One week after the Morris water maze test, all mice were tested in six trials (two blocks of three trials followed with a two hour rest period in between) for their ability to find a cued platform. Only those that had an average latency to reach the cued platform of less than 60 seconds were used in the analysis of the results. The results are shown in the table below as the integrated distance (area under the curve, AUC) traveled.

TABLE 7

Effect of an antisense oligonucleotide that mediates exon 19 inclusion on learning and memory

| Isis No. | Genotype | Number of mice in group | Distance (AUC) | Std. Error Meas. | SEQ ID No. |
|---|---|---|---|---|---|
| 439272 | WT | 12 | 1395 | 128.5 | 2 |
| 586115 | WT | 12 | 1523 | 148.4 | 50 |
| 439272 | TgCRND8 | 12 | 2893 | 138.3 | 2 |
| 586115 | TgCRND8 | 12 | 2184 | 144.9 | 50 |

The invention claimed is:

1. A compound comprising a modified oligonucleotide consisting of 8 to 30 linked nucleosides complementary to a target region of an LRP8 transcript, wherein the modified oligonucleotide has a nucleobase sequence comprising at least 8 contiguous nucleobases of any of the nucleobase sequences of SEQ ID NOs: 3-30.

2. The compound of claim 1, wherein the modified oligonucleotide is 100% complementary to a target region of an LRP8 transcript, wherein the target region is within nucleobases 78901 to 79258 of SEQ ID NO.: 1.

3. The compound of claim 1, wherein the modified oligonucleotide has a nucleobase sequence comprising at least 14 contiguous nucleobases that are complementary to a target region of an LRP8 transcript, wherein the target region is within nucleobases 78901 to 79258 of SEQ ID NO.: 1.

4. The compound of claim 1, wherein the modified oligonucleotide has a nucleobase sequence comprising at least 15 contiguous nucleobases that are complementary to a target region of an LRP8 transcript, wherein the target region is within nucleobases 78901 to 79258 of SEQ ID NO.: 1.

5. The compound of claim 1, wherein the modified oligonucleotide has a nucleobase sequence comprising at least 16 contiguous nucleobases that are complementary to a target region of an LRP8 transcript, wherein the target region is within nucleobases 78901 to 79258 of SEQ ID NO.: 1.

6. The compound of claim 1, wherein the modified oligonucleotide has a nucleobase sequence comprising at least 17 contiguous nucleobases that are complementary to a target region of an LRP8 transcript, wherein the target region is within nucleobases 78901 to 79258 of SEQ ID NO.: 1.

7. The compound of claim 1, wherein the modified oligonucleotide has a nucleobase sequence comprising at least 18 contiguous nucleobases that are complementary to a target region of an LRP8 transcript, wherein the target region is within nucleobases 78901 to 79258 of SEQ ID NO.: 1.

8. The compound of claim 1, wherein the modified oligonucleotide has a nucleobase sequence comprising at least 10 contiguous nucleobases of any of the nucleobase sequences of SEQ ID NOs: 3-30.

9. The compound of claim 1, wherein the modified oligonucleotide has a nucleobase sequence comprising at least 12 contiguous nucleobases of any of the nucleobase sequences of SEQ ID NOs: 3-30.

10. The compound of claim 1, wherein the modified oligonucleotide has a nucleobase sequence comprising at least 14 contiguous nucleobases of any of the nucleobase sequences of SEQ ID NOs: 3-30.

11. The compound of claim 1, wherein the modified ntisense oligonucleotide has a nucleobase sequence comprising at least an 8 nucleobase portion of any one of SEQ ID NOs: 17, 18, 19, or 20.

12. The compound of claim 1, wherein the modified oligonucleotide comprises at least one modified nucleoside.

13. The compound of claim 12, wherein at least one modified nucleoside comprises a modified sugar moiety.

14. The compound of claim 13, wherein at least one modified sugar moiety is a 2'-substituted sugar moiety.

15. The compound of claim 14, wherein the 2'-substituten of at least one 2'-substituted sugar moiety is selected from among: 2'-OMe, 2'-F, and 2'-MOE.

16. A method of modulating splicing an LRP8 transcript in a cell comprising contacting the cell with a compound according to claim 1.

17. A method of increasing the inclusion of exon 19 in LRP8 mRNA, comprising contacting the cell with a compound according to claim 1.

18. A method of preventing, treating, ameliorating, or slowing the progression of a disease, disorder, or condition associated with neurodegeneration, comprising administering the compound of claim 1.

19. A method of increasing the ratio of LRP8 mRNA having exon 19 relative to LRP8 mRNA without exon 19, comprising contacting a cell with the compound of claim 1.

* * * * *